(12) United States Patent
Yashiro et al.

(10) Patent No.: US 10,820,786 B2
(45) Date of Patent: Nov. 3, 2020

(54) ENDOSCOPE SYSTEM AND METHOD OF DRIVING ENDOSCOPE SYSTEM

(71) Applicant: FUJIFILM Corporation, Tokyo (JP)

(72) Inventors: Takashi Yashiro, Kanagawa (JP); Masahiro Kubo, Kanagawa (JP); Masaya Inoue, Kanagawa (JP); Takeichi Tatsuta, Kanagawa (JP); Issei Suzuki, Kanagawa (JP); Makoto Sugizaki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 273 days.

(21) Appl. No.: 15/725,285

(22) Filed: Oct. 5, 2017

(65) Prior Publication Data

US 2018/0092515 A1    Apr. 5, 2018

(30) Foreign Application Priority Data

Oct. 5, 2016 (JP) .................. 2016-197542

(51) Int. Cl.
   *A61B 1/00* (2006.01)
   *H04N 5/232* (2006.01)
   *G02B 23/24* (2006.01)

(52) U.S. Cl.
   CPC ...... *A61B 1/00174* (2013.01); *A61B 1/00009* (2013.01); *A61B 1/00045* (2013.01);
   (Continued)

(58) Field of Classification Search
   CPC .............................................. A61B 1/00174
   See application file for complete search history.

(56) References Cited

U.S. PATENT DOCUMENTS 9,526,402 B2   12/2016   Honda
9,554,097 B2   1/2017    Sasaki et al.
                         (Continued)

FOREIGN PATENT DOCUMENTS

EP    2762059       8/2014
JP    2012-245157   12/2012
                    (Continued)

OTHER PUBLICATIONS

"Search Report of European Counterpart Application," dated Mar. 1, 2018, pp. 1-8.
(Continued)

*Primary Examiner* — John P Leubecker
*Assistant Examiner* — Minqiao Huang
(74) *Attorney, Agent, or Firm* — JCIPRNET

(57) ABSTRACT

An endoscope system includes: an endoscope including a side-viewing observation unit that includes a field of view in a lateral direction of an insertion part to be inserted into an object to be observed and a second protruding portion that protrudes from the insertion part and forms a blind spot in the field of view of the side-viewing observation unit; an image acquisition unit that acquires a side-viewing observation image by using the side-viewing observation unit; a monitor that displays the side-viewing observation image; and a display control section that allows at least a part of the blind spot of the side-viewing observation image in which the second protruding portion is shown up not to be displayed, and displays the side-viewing observation image on the monitor.

18 Claims, 41 Drawing Sheets

(52) U.S. Cl.
CPC ...... *A61B 1/00096* (2013.01); *A61B 1/00177* (2013.01); *A61B 1/00179* (2013.01); *A61B 1/00181* (2013.01); *A61B 1/00183* (2013.01); *G02B 23/2423* (2013.01); *G02B 23/2484* (2013.01); *H04N 5/23238* (2013.01); *H04N 5/23296* (2013.01); *A61B 1/00165* (2013.01)

(56) References Cited

U.S. PATENT DOCUMENTS

| | | | |
|---|---|---|---|
| 2005/0038317 A1* | 2/2005 | Ratnakar | A61B 1/00105 600/101 |
| 2005/0073578 A1* | 4/2005 | Odlivak | G16H 10/40 348/65 |
| 2008/0234866 A1* | 9/2008 | Kishi | A61B 34/30 700/259 |
| 2011/0282148 A1* | 11/2011 | Kase | A61B 1/00177 600/113 |
| 2012/0088969 A1* | 4/2012 | Takahira | A61B 1/05 600/109 |
| 2012/0188351 A1* | 7/2012 | Kaku | G06T 7/0016 348/65 |
| 2013/0076879 A1 | 3/2013 | On | |
| 2014/0046131 A1* | 2/2014 | Morita | A61B 1/00179 600/109 |
| 2014/0204187 A1* | 7/2014 | Sasaki | A61B 1/00009 348/65 |
| 2015/0187119 A1* | 7/2015 | Masumoto | G06T 11/00 345/424 |
| 2015/0272423 A1* | 10/2015 | Ito | A61B 1/00009 600/476 |
| 2015/0282691 A1* | 10/2015 | Amling | A61B 1/045 600/103 |
| 2016/0338575 A1 | 11/2016 | Honda et al. | |
| 2017/0085762 A1 | 3/2017 | Obara et al. | |

FOREIGN PATENT DOCUMENTS

| | | |
|---|---|---|
| JP | 2013066646 | 4/2013 |
| JP | 2016-007745 | 1/2016 |
| WO | 2011055641 | 5/2011 |
| WO | 2014088076 | 6/2014 |
| WO | 2015122355 | 8/2015 |
| WO | 2015146836 | 10/2015 |
| WO | 2016072237 | 5/2016 |

OTHER PUBLICATIONS

"Office Action of Japan Counterpart Application", dated Apr. 28, 2020, with English translation thereof, p. 1-p. 4.

"Office Action of Japan Counterpart Application," with English translation thereof, dated Dec. 24, 2019, p. 1-p. 6.

* cited by examiner

ENDOSCOPE SYSTEM AND METHOD OF DRIVING ENDOSCOPE SYSTEM

CROSS-REFERENCE TO RELATED APPLICATION

This application claims priority under 35 USC 119 from Japanese Patent Application No. 2016-197542, filed 5 Oct. 2016, the disclosure of which is incorporated by reference herein.

BACKGROUND OF THE INVENTION

1. Field of the Invention

The present invention relates to an endoscope system that can perform direct-viewing observation and side-viewing observation and a method of driving the endoscope system.

2. Description of the Related Art

Diagnosis, which is performed using an endoscope system including a light source device, an endoscope, and a processor device, has become common in the field of medicine. In the endoscope system, the light source device generates illumination light. The endoscope includes a flexible insertion part, and the insertion part is inserted into a subject to pick up an image of an object to be observed by, for example, an image sensor that is mounted on a tip portion (hereinafter, referred to as a tip part) of the insertion part. Further, the processor device generates the image of the object to be observed, and displays the image on a monitor.

A direct-viewing observation type endoscope that picks up an image of an object to be observed present in a tip direction of a tip part (that is, the direction of the front along an insertion direction of an insertion part) and a side-viewing observation type endoscope that picks up an image of an object to be observed present in a lateral direction of a tip part (that is, the circumferential direction of an insertion part) are known as an endoscope used in an endoscope system in the related art. Further, endoscopes that can observe objects in both the tip direction and the lateral direction of a tip part have been known in recent years (WO2011/055641A (corresponding to US2011/282148A), JP2016-007745A, and JP2012-245157A (corresponding to US2014/046131A)).

SUMMARY OF THE INVENTION

A direct-viewing observation image that is obtained from the image pick-up of an object to be observed present in the tip direction of the tip part and a side-viewing observation image that is obtained from the image pick-up of an object to be observed present in the lateral direction of the tip part are obtained in the endoscope that can perform direct-viewing observation and side-viewing observation. For this reason, an observable range in a case in which the direct-viewing observation image and the side-viewing observation image are displayed is wider than an observable range in a case in which only one of the direct-viewing observation image and the side-viewing observation image is displayed. However, it may not be said that the endoscope is necessarily easy to use in observation, diagnosis, or the like in a case in which the direct-viewing observation image and the side-viewing observation image are merely displayed.

An object of the invention is to provide an endoscope system that is easy to use in observation, diagnosis, or the like since a method of displaying a direct-viewing observation image and a side-viewing observation image is improved in a case in which an endoscope capable of performing direct-viewing observation and side-viewing observation is used, and a method of driving the endoscope system.

An endoscope system of the invention comprises: an endoscope including a side-viewing observation unit that includes a field of view in a lateral direction of an insertion part to be inserted into an object to be observed and a protruding portion that protrudes from the insertion part and forms a blind spot in the field of view of the side-viewing observation unit; an image acquisition unit that acquires a side-viewing observation image by using the side-viewing observation unit; a display unit that displays the side-viewing observation image; and a display control section that allows at least a part of the blind spot of the side-viewing observation image in which the protruding portion is shown up not to be displayed, and displays the side-viewing observation image on the display unit.

It is preferable that the display control section allows at least a part of the blind spot not to be displayed by offsetting a display position of the side-viewing observation image with respect to a display region on the display unit.

It is preferable that the display control section allows at least a part of the blind spot not to be displayed by enlarging the side-viewing observation image with respect to the display region on the display unit.

It is preferable that the display control section includes a blind spot-non-display mode as a display mode for the side-viewing observation image and allows at least a part of the blind spot not to be displayed and displays the side-viewing observation image on the display unit in a case in which the display mode is set to the blind spot-non-display mode.

It is preferable that the display control section allows the entire blind spot not to be displayed.

It is preferable that the display control section changes a ratio of a portion, which is not to be displayed, of the blind spot.

It is preferable that the display control section changes the ratio of the portion, which is not to be displayed, of the blind spot in accordance with the movement of the insertion part.

It is preferable that the display control section changes the ratio of the portion, which is not to be displayed, of the blind spot in a case in which the insertion part is to be inserted into the object to be observed and a case in which the insertion part is to be extracted from the object to be observed.

It is preferable that the endoscope includes a direct-viewing observation unit including a field of view in a tip direction of the insertion part, the image acquisition unit acquires a direct-viewing observation image by using the direct-viewing observation unit, and the display control section adjusts display ratios of the side-viewing observation image and the direct-viewing observation image and changes the ratio of the portion, which is not to be displayed, of the blind spot in accordance with the display ratios of the side-viewing observation image and the direct-viewing observation image.

It is preferable that the endoscope system further includes a nozzle that ejects a washing substance to the side-viewing observation unit to wash the side-viewing observation unit and is provided in a non-display region not to be displayed in a case in which the display control section displays the side-viewing observation image on the display unit.

The invention provides a method of driving an endoscope system. the endoscope system includes an endoscope including a side-viewing observation unit that includes a field of view in a lateral direction of an insertion part to be inserted into an object to be observed and a protruding portion that protrudes from the insertion part and forms a blind spot in the field of view of the side-viewing observation unit, an image acquisition unit that acquires a side-viewing observation image by using the side-viewing observation unit, and a display unit that displays the side-viewing observation image. The method comprises: a step of allowing at least a part of the blind spot of the side-viewing observation image in which the protruding portion is shown up not to be displayed, and displaying the side-viewing observation image on the display unit by the display control section.

The invention can provide an endoscope system that is easy to use in observation, diagnosis, or the like since a method of displaying a direct-viewing observation image and a side-viewing observation image is improved in a case in which an endoscope capable of performing direct-viewing observation and side-viewing observation is used, and a method of driving the endoscope system.

DESCRIPTION OF THE PREFERRED EMBODIMENTS

First Embodiment

Figure 1:
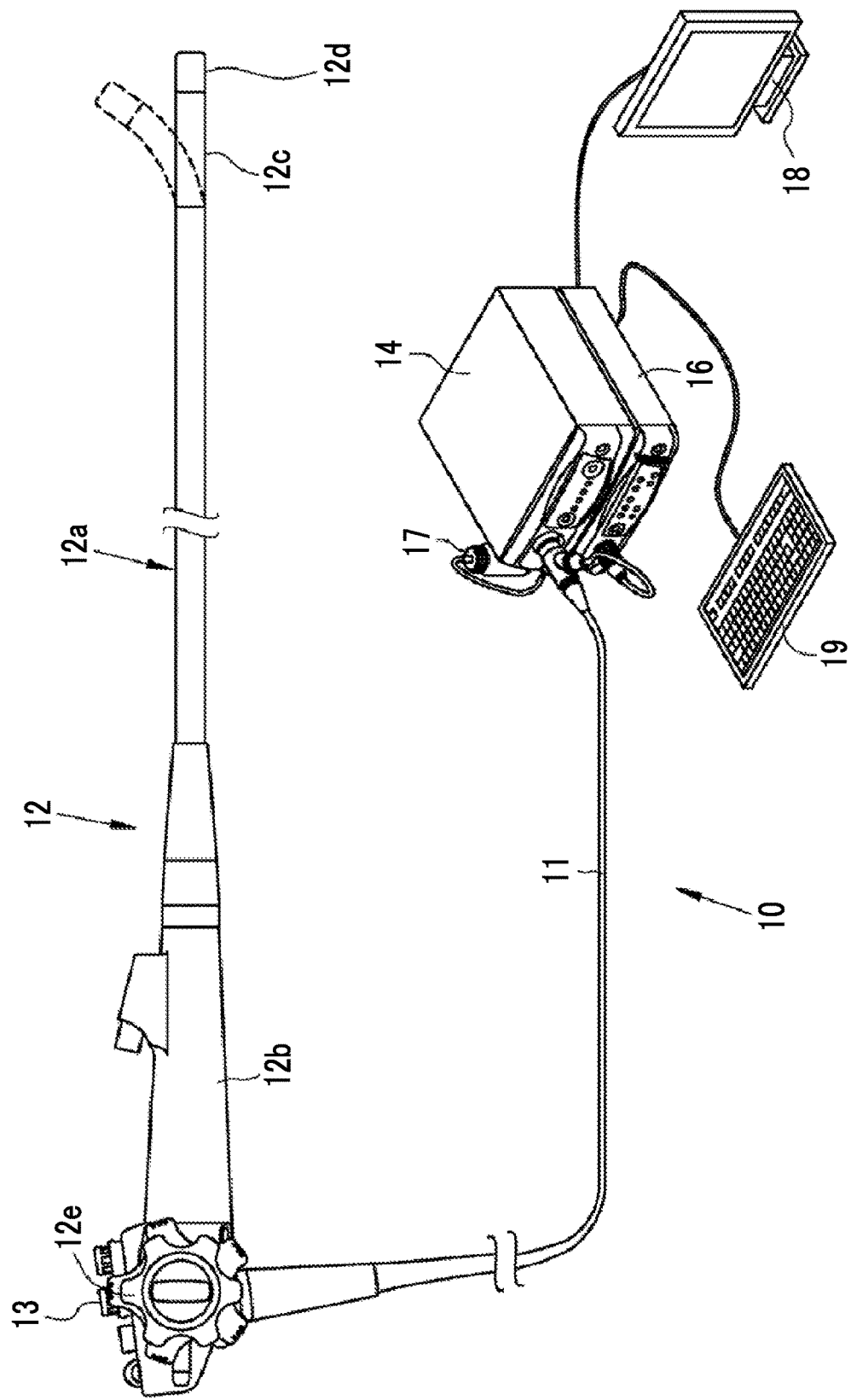
FIG. 1 is a diagram showing the appearance of an endoscope system.

As shown in FIG. 1, an endoscope system 10 includes an endoscope 12 that picks up an image of an object to be observed, a light source device 14 that generates illumination light, a processor device 16 that generates an image for observation (hereinafter, referred to as an observation image) by using an image (hereinafter, referred to as a picked-up image) obtained from the image pick-up of the object to be observed, a monitor 18 that is a display unit displaying the observation image, and a console 19 that is one of user interfaces. The endoscope 12 is optically connected to the light source device 14 via a universal cord 11 and is electrically connected to the processor device 16. Further, the endoscope 12 is connected to a tank 17, which stores washing liquid (for example, water) or the like, via the universal cord 11. A mechanism, such as a pump, for sending the washing liquid or the like of the tank 17 is provided in, for example, the light source device 14.

The endoscope 12 includes an insertion part 12a that is to be inserted into a subject, an operation unit 12b that is provided at a base end portion of the insertion part 12a, a bendable part 12c that is provided on the tip side of the insertion part 12a, and a tip part 12d. In a case in which an angle knob 12e provided on the operation unit 12b is operated, the bendable part 12c is bent. As a result of the bend of the bendable part 12c, the tip part 12d faces a desired direction.

Further, the operation unit 12b includes, for example, a washing switch 13, which is used to eject washing liquid from nozzles provided in the tip part 12d, in addition to the angle knob 12e. In a case in which the washing switch 13 is pressed in a state in which dirt adheres to the tip part 12d due to contact between the object to be observed and the tip part 12d or the like, the washing liquid is ejected toward at least a part of the tip part 12d from the nozzles provided in the tip part 12d. As a result, a portion of the tip part 12d to which the washing liquid is ejected can be washed. In the endoscope system 10, the washing liquid is liquid, such as water or liquid medicine. Further, for convenience sake, washing "liquid" is described in this specification. However, gas, such as air, solid, a mixture of materials having different phases, and the like, which are to be ejected from the nozzles, are also included in the "washing liquid", as long as they are used for washing.

Figure 2:
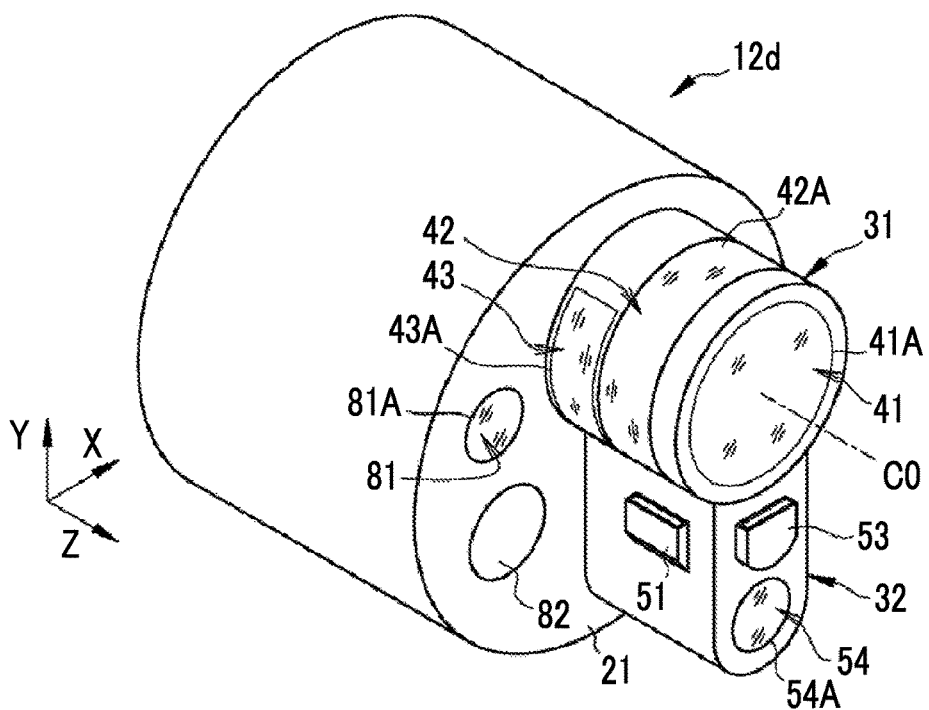
FIG. 2 is a perspective view showing the appearance of a tip part.
Figure 3:
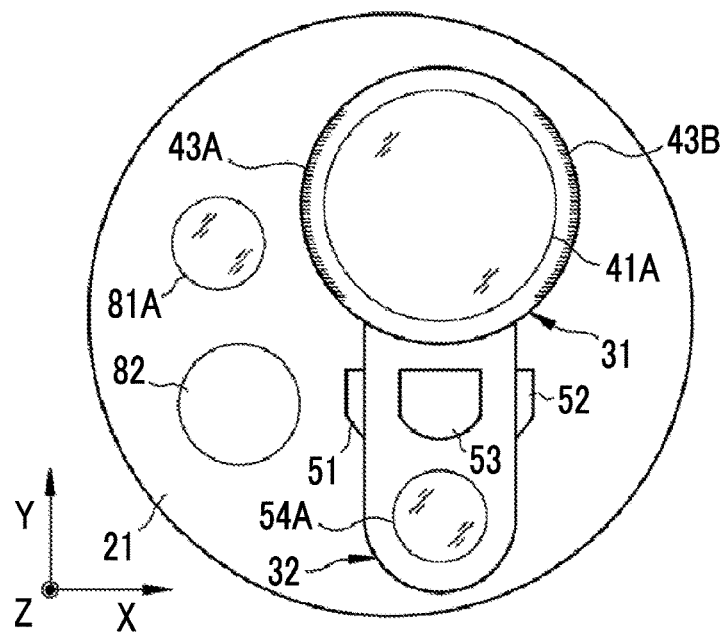
FIG. 3 is a front view of the tip part.

As shown in FIGS. 2 and 3, the tip part 12d of the insertion part 12a to be inserted into an object to be observed includes two protruding portions, that is, a first protruding portion 31 and a second protruding portion 32. The first and second protruding portions 31 and 32 further protrude from a tip surface 21 of the tip part 12d in a Z direction that is a tip direction of the insertion part 12a. The second protruding portion 32 is adjacent to the first protruding portion 31, and protrudes from the tip surface 21 in the tip direction of the insertion part 12a (the Z direction). Hereinafter, a direction toward the first protruding portion 31 from the second protruding portion 32 is referred to as a Y direction, and a direction perpendicular to the Z direction and the Y direction is referred to as an X direction. Further, the positive side of the insertion part 12a, the tip part 12d, the first protruding portion 31, or the second protruding portion 32 in the X direction is referred to as "left"; the negative side thereof in the X direction is referred to as "right"; the positive side thereof in the Y direction is referred to as "up"; and the negative side thereof in the Y direction is referred to as "down". The positive side of the insertion part 12a, the tip part 12d, the first protruding portion 31, or the second protruding portion 32 in the Z direction is referred to as "front" or "tip (the tip direction)", and the negative side thereof in the Z direction is referred to as "base end (a base end direction)".

The first protruding portion 31 has a substantially cylindrical shape as a whole, and includes a direct-viewing observation window 41A that is provided at the tip thereof and is an observation window for a direct-viewing observation unit 41 and a side-viewing observation window 42A that is provided on the side thereof and is an observation window for a side-viewing observation unit 42. The direct-viewing observation unit 41 has the field of view in the tip direction of the insertion part 12a, and picks up an image of an object to be observed that is present in the tip direction of the insertion part 12a. The direct-viewing observation unit 41 includes, for example, an image pickup lens, an image sensor, and the like. An optical member, such as the image pickup lens of the direct-viewing observation unit 41, or a transparent protective member that protects the optical member, such as the image pickup lens, is exposed to the tip (the surface facing the Z direction) of the first protruding portion 31. A portion, which is exposed to the tip of the first protruding portion 31, is the direct-viewing observation window 41A that takes in light incident from the object to be observed present in the tip direction of the insertion part 12a.

The side-viewing observation unit 42 has the field of view in a lateral direction of the insertion part 12a, and picks up an image of an object to be observed that is present in the lateral direction of the insertion part 12a. The side-viewing observation unit 42 includes, for example, an image pickup lens, an image sensor, and the like as in the case of the direct-viewing observation unit 41. An optical member, such as the image pickup lens of the side-viewing observation unit 42, or a transparent protective member that protects the optical member, such as the image pickup lens, is exposed to the side surface of the first protruding portion 31 (the surface forming the outer periphery of the first protruding portion 31). A portion, which is exposed to the side surface of the first protruding portion 31, is the side-viewing observation window 42A that takes in light incident from the object to be observed present in the lateral direction of the insertion part 12a. In the endoscope 12 of this embodiment, the side-viewing observation unit 42 is exposed over the circumference of the first protruding portion 31, which excludes a joint portion between the first protruding portion 31 and the second protruding portion 32, in the circumferential direction of the first protruding portion 31 and forms the belt-like side-viewing observation window 42A.

Further, the first protruding portion 31 includes a first side-viewing illumination window 43A, which is an illumination window for a side-viewing illumination unit 43, in addition to the direct-viewing observation window 41A and the side-viewing observation window 42A. The side-viewing illumination unit 43 emits illumination light toward the field of view of the side-viewing observation unit 42 from the first side-viewing illumination window 43A. The side-viewing illumination unit 43 includes, for example, a light guide that guides the illumination light emitted from the light source device 14, and an optical member, such as a lens or a mirror, that diffuses and emits the illumination light guided to the tip part 12d by the light guide toward the field of view of the side-viewing observation unit 42. The optical member, such as the mirror of the side-viewing illumination unit 43, or a transparent protective member that protects the optical member, such as the mirror, is exposed to the side surface of the first protruding portion 31. A portion, which is exposed to the side surface of the first protruding portion 31, is the first side-viewing illumination window 43A that emits illumination light in the lateral direction of the insertion part 12a. In the endoscope 12 of this embodiment, a part of the outer periphery of the first protruding portion 31, which excludes the joint portion between the first protruding portion 31 and the second protruding portion 32, forms side-viewing illumination windows. Further, the first side-viewing illumination window 43A is provided on the right side surface of the first protruding portion 31 in FIG. 2, and a second side-viewing illumination window 43B, which emits illumination light to the field of view of the side-viewing observation unit 42, is also provided on the left side surface of the first protruding portion 31 (see FIG. 3). The positions and sizes of the first and second side-viewing illumination windows 43A and 43B are symmetrical to each other.

Figure 4:
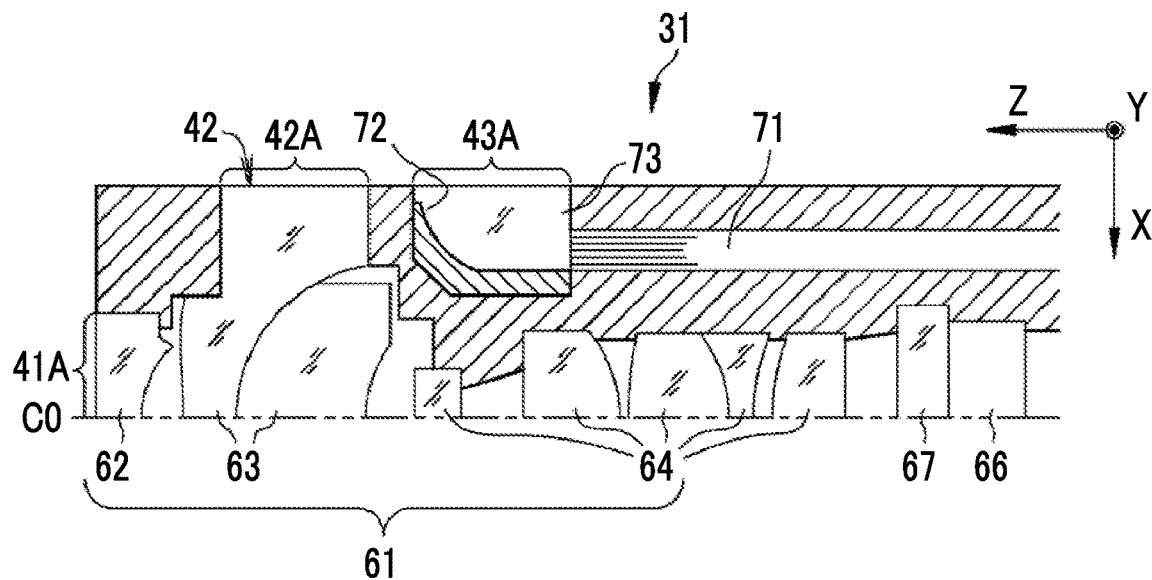
FIG. 4 is a cross-sectional view of a part of a first protruding portion.

In this embodiment, the direct-viewing observation unit 41 and the side-viewing observation unit 42 includes a common image pickup lens 61 and a common image sensor 66 as shown in FIG. 4. The image pickup lens 61 includes a front group lens 62, a mirror lens 63 that is formed of two lenses joined to each other, and a rear group lens 64. The front surface of the front group lens 62 is exposed to the tip of the first protruding portion 31. That is, the front surface of the front group lens 62 forms the direct-viewing observation window 41A of the direct-viewing observation unit 41. Further, the side surface of the mirror lens 63 is exposed to the side surface of the first protruding portion 31. For this reason, the side surface of the mirror lens 63 forms the side-viewing observation window 42A of the side-viewing observation unit 42.

The mirror lens 63 guides light, which is incident through the front group lens 62 from an object to be observed present in the tip direction of the insertion part 12a, to the rear group lens 64. Then, the light forms an image on the image pickup surface of the image sensor 66 through a cover glass 67. Accordingly, the image pickup lens 61 and the image sensor 66 serving as the direct-viewing observation unit 41 pick up an image of the object to be observed that is present in the tip direction of the insertion part 12a.

On the other hand, the mirror lens 63 sequentially reflects light, which is incident from an object to be observed present in the lateral direction of the insertion part 12a through the side surface of the mirror lens 63, by a joint surface between the two lenses of the mirror lens 63 and the front surface of the mirror lens 63, and guides the light to the rear group lens 64. Then, the light forms an image on the image pickup surface of the image sensor 66 through the cover glass 67. Accordingly, the image pickup lens 61 and the image sensor 66 serving as the side-viewing observation unit 42 pick up an image of the object to be observed that is present in the lateral direction of the insertion part 12a.

Further, the side-viewing illumination unit 43 includes a light guide 71, a reflective member 72, and a filling member 73. The light guide 71 is optically connected to the light source device 14, and guides illumination light that is emitted from the light source device 14. Then, the illumination light is emitted to the reflective member 72 from the end face of the light guide 71 through the filling member 73. The reflective member 72 diffuses the illumination light, which is incident from the light guide 71, in the lateral direction of the insertion part 12a, and emits the illumination light to a range that includes the field of view of at least the side-viewing observation unit 42. The filling member 73 is a protective member that protects the emission end face of the light guide 71 and the reflective member 72, and is transparent. Furthermore, the filling member 73 smoothly fills a groove portion, which is formed between the light guide 71 and the reflective member 72, along the side surface of the first protruding portion 31. For this reason, the filling member 73 forms the first side-viewing illumination window 43A. The second side-viewing illumination window 43B is also the same as described above.

In the endoscope 12 of this embodiment, the side-viewing observation window 42A is provided on the side surface of the first protruding portion 31 so as to be close to the tip of the first protruding portion 31, and the first side-viewing illumination window 43A and the second side-viewing illumination window 43B are provided on the side surface of the first protruding portion 31 so as to be close to the base end of the first protruding portion 31. However, the positions and the order of the side-viewing observation window 42A, the first side-viewing illumination window 43A, and the second side-viewing illumination window 43B are arbitrary. Since vignetting or the like caused by the tip surface 21 or the like is prevented and the field of view of the side-viewing illumination unit 43 is easily ensured in a case in which the side-viewing observation window 42A is provided on the side surface of the first protruding portion 31 so as to be close to the tip of the first protruding portion 31, it is good that the side-viewing observation window 42A is provided on the side surface of the first protruding portion 31 so as to be close to the tip of the first protruding portion 31 as much as possible.

The second protruding portion 32 includes nozzles that eject washing liquid to wash the tip part 12d. More specifically, the second protruding portion 32 includes a nozzle 51 and a nozzle 52 (see FIG. 3) that eject washing liquid toward the side-viewing observation window 42A. The nozzle 51 is provided on the right side surface of the second protruding portion 32, and the nozzle 52 is provided on the left side surface of the second protruding portion 32. The nozzles 51 and 52 have the same properties in terms of being provided on the second protruding portion 32 and washing the side-viewing observation window 42A by ejecting washing liquid toward the side-viewing observation window 42A.

The second protruding portion 32 further includes a nozzle 53 at the tip of the second protruding portion 32. The nozzle 53 washes the direct-viewing observation window 41A by ejecting washing liquid toward the direct-viewing observation window 41A that is an exposed portion of the direct-viewing observation unit 41.

Figure 5:
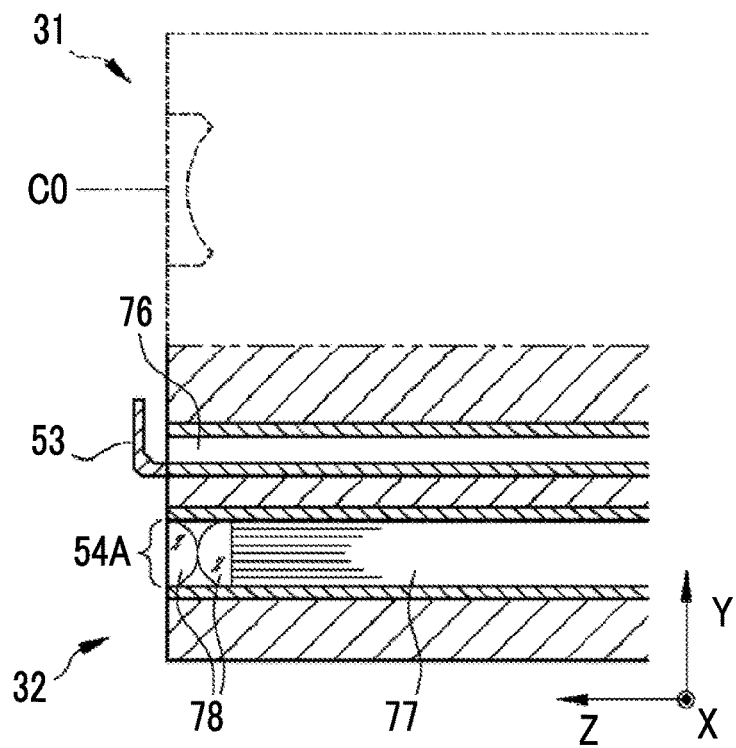
FIG. 5 is a cross-sectional view of a second protruding portion.

As shown in FIG. 5, the nozzle 53 is an outlet of an air/liquid supply channel 76. For this reason, in a case in which washing liquid or the like stored in the tank 17 is sent out through the air/liquid supply channel 76, the washing liquid or the like is ejected from the nozzle 53. The air/liquid supply channel 76 communicates with the second protruding portion 32, the tip part 12d, the insertion part 12a, the universal cord 11, and the like. In this embodiment, the air/liquid supply channel 76 is branched at the second protruding portion 32, the tip part 12d, the insertion part 12a, or the universal cord 11 also communicates with other nozzles, such as the nozzles 51 and 52 in common. For this reason, for example, in a case in which the washing switch 13 is pressed to send washing liquid into the air/liquid supply channel 76, washing liquid is simultaneously ejected not only from the nozzle 53 but also the nozzles 51 and 52. Accordingly, the endoscope 12 can simultaneously wash the direct-viewing observation window 41A and the side-viewing observation window 42A by a simple operation.

The second protruding portion 32 includes a direct-viewing illumination window 54A, which is an illumination window for a direct-viewing illumination unit 54 for emitting illumination light toward the field of view of the direct-viewing observation unit 41, in addition to the nozzles 51, 52, and 53. The direct-viewing illumination unit 54 includes, for example, a light guide 77 that guides illumination light emitted from the light source device 14, and an illumination lens 78 and the like that diffuse and emit the illumination light, which is guided to the tip part 12d by the light guide 77, toward the field of view of the direct-viewing observation unit 41 (see FIG. 4). The illumination lens of the direct-viewing illumination unit 54, or a transparent protective member, which protects the illumination lens, is exposed to the tip of the second protruding portion 32. A portion, which is exposed to the tip of the second protruding portion 32, is the direct-viewing illumination window 54A. In this embodiment, the front surface of the illumination lens 78 is exposed to the tip of the second protruding portion 32. For this reason, the front surface of the illumination lens 78 forms the direct-viewing illumination window 54A.

The tip surface 21 of the tip part 12d includes a direct-viewing illumination window 81A, which is an illumination window for a direct-viewing illumination unit 81, and a forceps port 82 in addition to the first and second protruding portions 31 and 32.

The direct-viewing illumination unit 81 emits illumination light toward the field of view of the direct-viewing observation unit 41 as in the case of the direct-viewing illumination unit 54 that is provided in the second protruding portion 32. Further, the direct-viewing illumination unit 81 includes, for example, a light guide 84 (see FIG. 6) that guides illumination light emitted from the light source device 14, and an illumination lens and the like (not shown) that diffuse and emit the illumination light, which is guided to the tip part 12d by the light guide 84, toward the field of view of the direct-viewing observation unit 41. In this embodiment, the light guide of the direct-viewing illumination unit 81 is connected to the light guide 77 of the direct-viewing illumination unit 54. For this reason, the light guide of the direct-viewing illumination unit 81 is substantially common to the light guide 77 of the direct-viewing illumination unit 54. Accordingly, the direct-viewing illumination units 54 and 81 simultaneously emit the same illumination light from the respective illumination windows thereof. However, there is a case where the amount of light emitted from the light guide 77 of the direct-viewing illumination unit 54 and the amount of light emitted from the light guide of the direct-viewing illumination unit 81 are different from each other due to a difference in thickness between the light guide 77 and the light guide 84. The illumination lens of the direct-viewing illumination unit 81 or a transparent protective member, which protects the illumination lens, is exposed to the tip surface 21. A portion, which is exposed to the tip surface 21, is the direct-viewing illumination window 81A.

The forceps port 82 is an outlet for a treatment tool, such as forceps. In a case in which a treatment tool, such as forceps, is inserted from an inlet port (not shown) that is provided at the base end portion of the endoscope 12, the treatment tool reaches the forceps port 82 through a forceps channel and the tip of the treatment tool can protrude from the forceps port 82. The forceps channel communicates with the tip part 12d, the insertion part 12a, and the operation unit 12b.

Since the side-viewing observation window 42A is provided on the side surface of the first protruding portion 31 and the second protruding portion 32 is adjacent to the first protruding portion 31 and protrudes from the tip surface 21 in the tip direction of the insertion part 12a (the Z direction), the second protruding portion 32 is a protruding portion that forms the blind spot of the field of view of the side-viewing observation unit 42. That is, since the second protruding portion 32 is within a part of the field of view of the side-viewing observation unit 42 due to the disposition of the respective units, an image of an object to be observed cannot be picked up in a part of an angular range.

Figure 6:
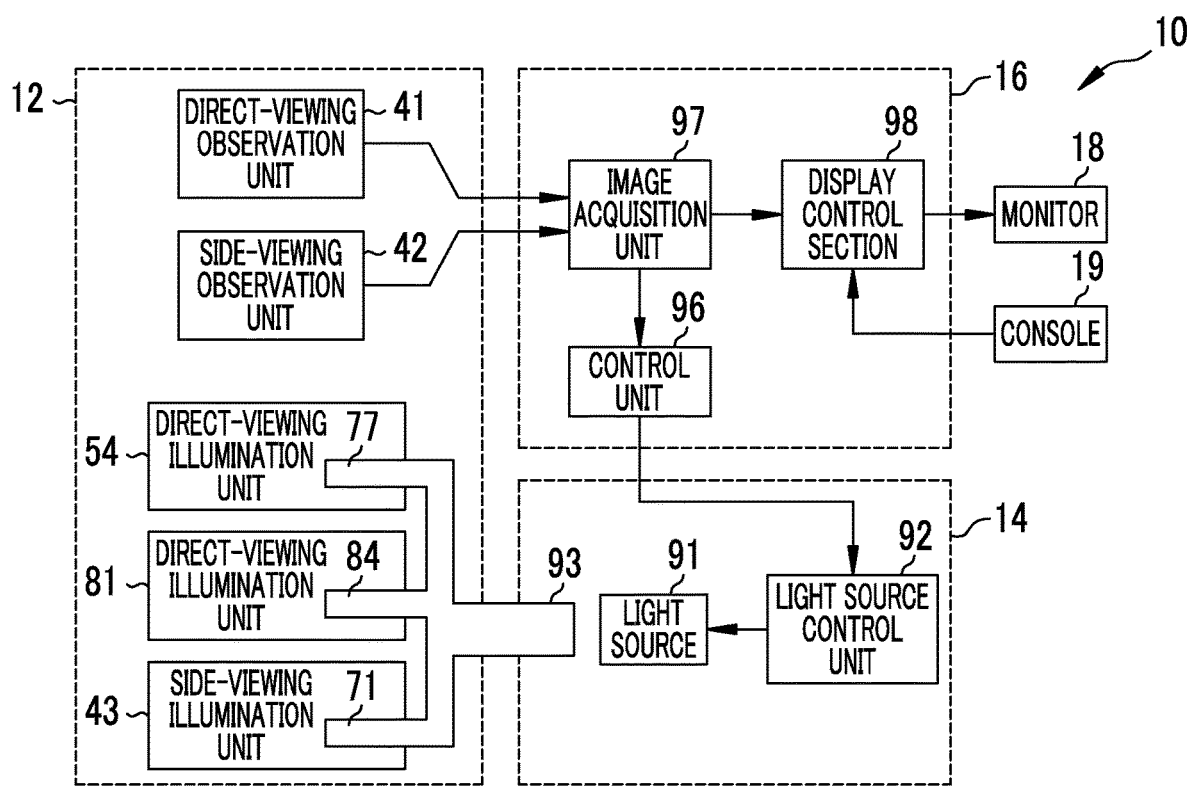
FIG. 6 is a block diagram of the endoscope system.

As shown in FIG. 6, the light source device 14 includes a light source 91 that generates illumination light, and a light source control unit 92 that controls the light source 91. The light source 91 includes, for example, a plurality of light emitting diodes (LEDs) that can be independently controlled and emit light having different wavelengths or different wavelength ranges. Other semiconductor light sources, which include laser diodes (LD) or the like instead of LEDs, may be used as the light source 91. A combination of a semiconductor light source, a fluorescent substance, which uses light emitted from the semiconductor light source as excitation light to emit light having other colors, and the like may be used as the light source device. A lamp light source, such as a xenon lamp, may also be used as the light source 91. Further, the light source 91 may be formed of a semiconductor light source, a combination of a semiconductor light source and a fluorescent substance, or a combination of a lamp light source and an optical filter that adjusts a wavelength band or a spectrum. For example, plural kinds of illumination light can be emitted with the use of a combination of a white LED and an optical filter.

The light source control unit 92 controls each of the turn-on, the turn-off, and the amount of light of the LEDs or the like of the light source 91 in accordance with a drive timing of the image sensor 66. Particularly, in a case in which one observation image is generated using a plurality of picked-up images (that is, a multi-frame observation mode), the light source control unit 92 can change the wavelength band or a spectrum of the illumination light for every image pickup frame where a plurality of picked-up images to be used for the generation of an observation image is obtained, as a result of the control of the LEDs. The turn-on means that the amount of light allowing the image sensor 66 to pick up an image of an object to be observed (the amount of light for allowing an image of an object to be observed to be visually recognized in an observation image) is emitted. The turn-on includes a case in which light is reduced to the amount of light not allowing the image sensor 66 to pick up an image of an object to be observed in addition to a case in which light emission is completely stopped. Further, in a case in which each of the light sources of the light source 91 is a semiconductor light source, the light source control unit 92 controls the turn-on, the turn-off, and the amount of light of each light source by pulse modulation control.

Illumination light, which is emitted from the light source 91, is incident on a light guide 93. Since the light guide 93 is inserted into the endoscope 12 and the universal cord from the light source device 14, the light guide 93 transmits illumination light up to the tip part 12d of the endoscope 12. The light guide 93 is branched to at least the light guide 77 of the direct-viewing illumination unit 54, the light guide 84 of the direct-viewing illumination unit 81, and the light guide 71 of the side-viewing illumination unit 43, and transmits illumination light to each of these illumination units. A multimode fiber can be used as the light guide 93 and each branched light guide, such as the light guide 71. For example, a thin fiber cable of which a total diameter of a core diameter of 105 μm, a cladding diameter of 125 μm, and a protective layer forming a covering is in the range of φ 0.3 to 0.5 mm can be used.

The processor device 16 includes a control unit 96, an image acquisition unit 97, and a display control section 98. The control unit 96 is a central processing unit (CPU) that generally controls the endoscope system 10. Each of other processing units (such as the image acquisition unit and the display control section) is configured by the CPU executing corresponding program or by a dedicated processing circuitry. The control unit 96 performs, for example, synchronization control for allowing an image pickup timing of the image sensor 66 to correspond to an image pickup timing of each LED of the light source 91. The control of the image pickup timing of each LED of the light source 91 is performed through the light source control unit 92. Further, the control unit 96 performs automatic exposure control (AE control) for automatically controlling exposure. In this embodiment, the control unit 96 performs AE control by driving the image sensor 66 at a fixed timing and adjusting the amount of light (that is, the amount of illumination light) emitted from each LED or the like of the light source 91. During AE control, the control unit 96 acquires a direct-viewing observation image 111 (see FIG. 8) and a side-viewing observation image 112 (see FIG. 8) or any one of the direct-viewing observation image 111 and the side-viewing observation image 112 from the image acquisition unit 97, and determines the amount of light emitted from each LED of the light source 91 by using the acquired image.

The image acquisition unit 97 acquires the direct-viewing observation image 111 by the direct-viewing observation unit 41, and acquires the side-viewing observation image 112 by the side-viewing observation unit 42. In this embodiment, the direct-viewing observation unit 41 and the side-viewing observation unit 42 share the image pickup lens 61 and the image sensor 66. Accordingly, the image acquisition unit 97 acquires an image that is picked up by the image sensor 66 (hereinafter, referred to as a picked-up image), and obtains a picked-up image, which includes the direct-viewing observation image 111 and the side-viewing observation image 112, by various kinds of image processing and the like on the acquired picked-up image. That is, a part of the picked-up image, which is obtained from the image sensor 66, is the direct-viewing observation image 111, and the other part of the picked-up image, which is obtained from the image sensor 66, is the side-viewing observation image 112.

The image acquisition unit 97 functions as, for example, a digital signal processor (DSP) and a noise reduction unit.

The image acquisition unit 97 performs various kinds of processing, such as defect correction processing, offset processing, gain correction processing, linear matrix processing, gamma conversion processing, demosaic processing, and YC conversion processing, on the acquired picked-up image as necessary. This is the function of the image acquisition unit 97 as the DSP. The defect correction processing is processing for correcting the pixel value of a pixel corresponding to a defective pixel of the image sensor 66. The offset processing is processing for reducing a dark current component from the picked-up image having been subjected to the defect correction processing and setting an accurate zero level. The gain correction processing is processing for adjusting the signal level of each picked-up image by multiplying the picked-up image, which has been subjected to the offset processing, by a gain. The linear matrix processing is processing for improving the color reproducibility of the picked-up image subjected to the offset processing, and the gamma conversion processing is processing for adjusting the brightness or chroma of the picked-up image having been subjected to the linear matrix processing. The demosaic processing (also referred to as equalization processing or synchronization processing) is processing for interpolating the pixel value of a missing pixel, and is performed on the picked-up image having been subjected to the gamma conversion processing. The missing pixel is a pixel that does not have a pixel value since pixels having other colors are disposed in the image sensor 66 due to the arrangement of color filters. For example, since a B image is a picked-up image that is obtained from the image pick-up of the object to be observed at a B pixel, pixels of the B image, which are present at positions corresponding to a G pixel and an R pixel of the image sensor 66, does not have a pixel value. In the demosaic processing, the pixel values of pixels of a B image, which are present at positions corresponding to a G pixel and an R pixel of the image sensor 66, are generated through the interpolation of the B image. The YC conversion processing is processing for converting an image, which has been subjected to the demosaic processing, into a luminance channel Y, a color-difference channel Cb, and a color-difference channel Cr.

The image acquisition unit 97 performs noise-reduction processing on the luminance channel Y, the color-difference channel Cb, and the color-difference channel Cr by using, for example, a moving-average method, a median filter method, or the like. A conversion unit 59 converts the luminance channel Y, the color-difference channel Cb, and the color-difference channel Cr, which have been subjected to the noise-reduction processing, into a picked-up image having the respective colors of BGR again. This is the function of the image acquisition unit 97 as the noise reduction unit.

The display control section 98 acquires the direct-viewing observation image 111 and the side-viewing observation image 112 from the image acquisition unit 97. Then, the display control section 98 generates an image for display (hereinafter, referred to as a display image) (see FIG. 8) by using the direct-viewing observation image 111 and the side-viewing observation image 112 or any one of the direct-viewing observation image 111 and the side-viewing observation image 112. The display control section 98 displays the generated display image on the monitor 18. In this embodiment, the display control section 98 generates and displays a display image by using both the direct-viewing observation image 111 and the side-viewing observation image 112 unless specifically mentioned.

Figure 7:
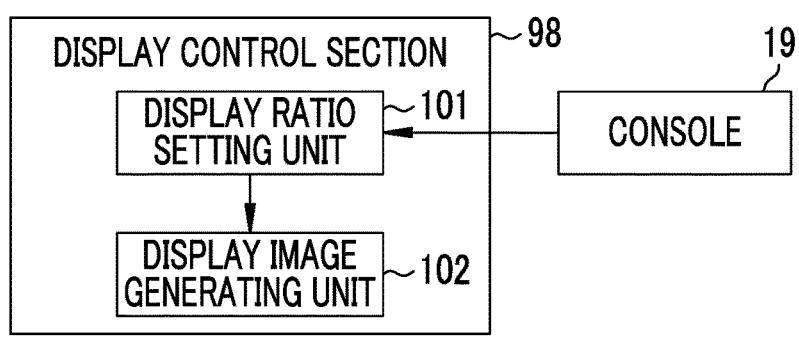
FIG. 7 is a block diagram of a display control section.

Further, the display control section 98 masks a portion of the side-viewing observation image 112 corresponding to a blind spot, and adjusts a relative display ratio of the direct-viewing observation image 111 and the side-viewing observation image 112 on the monitor 18 serving as the display unit. For this reason, as shown in FIG. 7, the display control section 98 includes a display ratio setting unit 101 and a display image generating unit 102. The display ratio setting unit 101 adjusts a relative display ratio of the direct-viewing observation image 111 and the side-viewing observation image 112 on the monitor 18 serving as the display unit.

The display ratio setting unit 101 includes a plurality of display modes as the setting of the relative display ratio in advance. Specifically, the display ratio setting unit 101 includes three kinds of display modes, that is, a standard mode, a direct-viewing enlargement mode, and a side-viewing enlargement mode.

The standard mode is a display mode in which both the direct-viewing observation image 111 and the side-viewing observation image 112 are substantially not enlarged or reduced and a relative display ratio of the direct-viewing observation image 111 and the side-viewing observation image 112 is set to a display ratio originally obtained when an image is picked up. That is, in the standard mode, a relative display ratio of the direct-viewing observation image 111 and the side-viewing observation image 112 becomes substantially a display ratio that is obtained when an image is picked up. "Substantially not enlarged or reduced" means the exclusion of the enlargement or reduction of the direct-viewing observation image 111 or the side-viewing observation image 112 that is inevitable for the connection between the direct-viewing observation image 111 and the side-viewing observation image 112. Accordingly, even in the standard mode, there is a case where any one or both of the direct-viewing observation image 111 and the side-viewing observation image 112 is enlarged or reduced for connection. Hereinafter, for simplification, it is regarded in the standard mode that the display area of the direct-viewing observation image 111 on the monitor 18 serving as the display unit and the display area of the side-viewing observation image 112 on the monitor 18 are substantially equal to each other.

The direct-viewing enlargement mode is a display mode in which the display area of the direct-viewing observation image 111 on the monitor 18 serving as the display unit is enlarged in comparison with the case of the standard mode. That is, in the case of the direct-viewing enlargement mode, the display ratio setting unit 101 relatively increases the display ratio of the direct-viewing observation image 111 to the side-viewing observation image 112. Further, the direct-viewing enlargement mode includes a case in which only the direct-viewing observation image 111 of the direct-viewing observation image 111 and the side-viewing observation image 112 is substantially displayed.

The side-viewing enlargement mode is a display mode in which the display area of the side-viewing observation image 112 on the monitor 18 serving as the display unit is enlarged in comparison with the case of the standard mode. That is, in the case of the side-viewing enlargement mode, the display ratio setting unit 101 relatively increases the display ratio of the side-viewing observation image 112 to the direct-viewing observation image 111. Further, the side-viewing enlargement mode includes a case in which only the side-viewing observation image 112 of the direct-viewing observation image 111 and the side-viewing observation image 112 is substantially displayed.

A doctor or the like who is a user of the endoscope system 10 can arbitrarily set a specific display ratio of the direct-viewing observation image 111 in the direct-viewing enlargement mode and the side-viewing observation image 112 in the side-viewing enlargement mode by using, for example, the console 19, the switch of the operation unit 12b, or an input device (hereinafter, referred to as the console 19), such as a foot switch. The specific display ratio of the direct-viewing observation image 111 and the side-viewing observation image 112 can be arbitrarily changed even during observation. The side-viewing enlargement mode is automatically made in a case in which a doctor or the like sets a numerical value or the like for allowing the display area of the direct-viewing observation image 111 in the direct-viewing enlargement mode to be smaller than that in the standard mode; and vice versa. Further, the standard mode, the direct-viewing enlargement mode, and the side-viewing enlargement mode can also be arbitrarily switched by the console 19 or the like, likewise.

The display image generating unit 102 generates a display image by enlarging or reducing the direct-viewing observation image 111 and the side-viewing observation image 112 or any one of the direct-viewing observation image 111 and the side-viewing observation image 112 as necessary in accordance with the display ratio that is set by the display ratio setting unit 101, connecting the direct-viewing observation image 111 to the side-viewing observation image 112, and masking a portion of the side-viewing observation image 112 corresponding to a blind spot.

"Mask" means that data of the side-viewing observation image 112 is modulated or replaced with other images or the like. A portion of the side-viewing observation image 112 corresponding to a blind spot is a portion at which an image of an object to be observed cannot be picked up due to the presence of the second protruding portion 32. Hereinafter, in the display image, a portion of the side-viewing observation image 112, which corresponds to a blind spot caused by the presence of the second protruding portion 32, is referred to as a first blind spot portion. The display image generating unit 102 masks at least the first blind spot portion in the display image. In addition, in this embodiment, the display image generating unit 102 also masks a portion (hereinafter, referred to as a second blind spot portion) of the side-viewing observation image 112, which is positioned outside the field of view of the side-viewing observation unit 42 and at which an image of an object to be observed cannot be picked up from the beginning, in the display image. The display control section 98 displays a display image, which is generated by the display image generating unit 102, on the monitor 18.

In the endoscope system 10, a display image of which a relative display ratio of the direct-viewing observation image 111 and the side-viewing observation image 112 is adjusted is displayed on the monitor 18. For example, in a case in which a display mode is set to the standard mode, the display control section 98 generates a display image 113 shown in FIG. 8 and displays the display image 113 on the monitor 18. The display control section 98 connects the outer periphery of the direct-viewing observation image 111 to the inner periphery of the side-viewing observation image 112 with a size, which is originally obtained when an image is picked up, by the display image generating unit 102 to generate the display image 113 in the standard mode. According to the display image 113 in the standard mode, an object to be observed in a wider range can be observed in comparison with a case in which only the direct-viewing observation image 111 or only the side-viewing observation image 112 is displayed.

Figure 8:
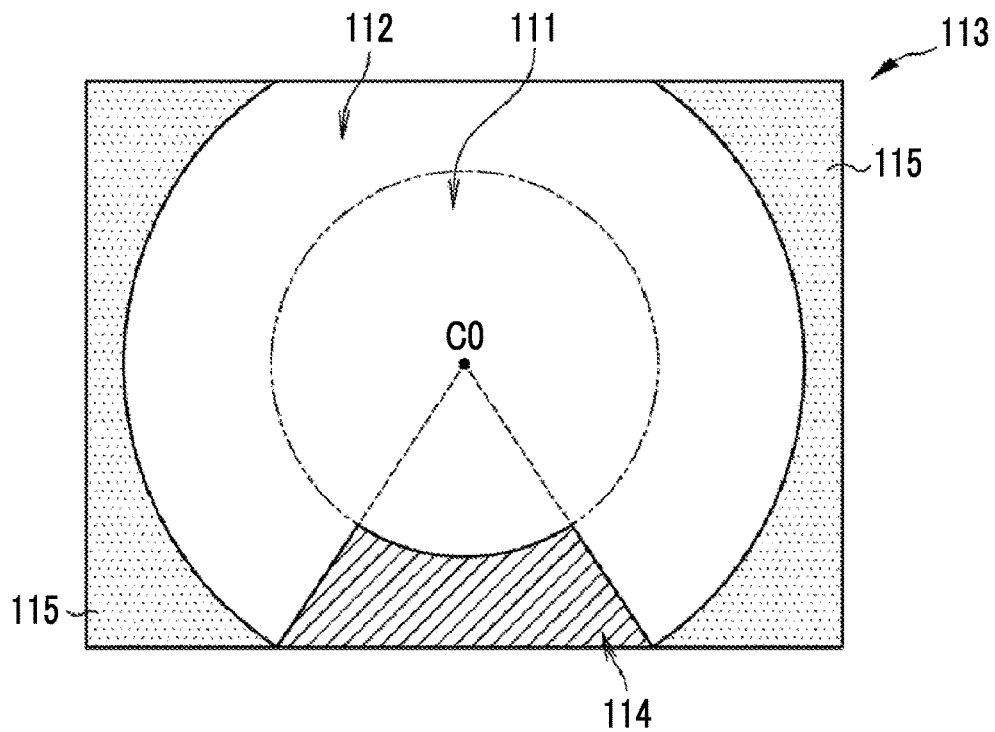
FIG. 8 shows a display image in a standard mode.

Actually, there is no clear boundary between the direct-viewing observation image 111 and the side-viewing observation image 112, but a boundary is shown in FIG. 8 by a two-dot chain line for description (the same hereinafter). Further, a portion of the side-viewing observation image 112 at which an object to be observed is shown up has a substantially annular shape, but a first blind spot portion 114 caused by the second protruding portion 32 is formed from the center C0 in a constant angular range. For this reason, the display control section 98 masks the first blind spot portion 114 in a case in which the display control section 98 is to generate the display image 113 by the display image generating unit 102. Furthermore, a portion outside the side-viewing observation image 112 is a second blind spot portion 115 at which an image of an object to be observed cannot be originally picked up. For this reason, the display control section 98 masks the second blind spot portion 115 in a case in which the display control section 98 is to generate the display image 113 by the display image generating unit 102. Accordingly, the first and second blind spot portions 114 and 115 at which an object to be observed is not shown up, are clearly distinguished from the other portion of the side-viewing observation image 112 at which an object to be observed is shown up.

Figure 9:
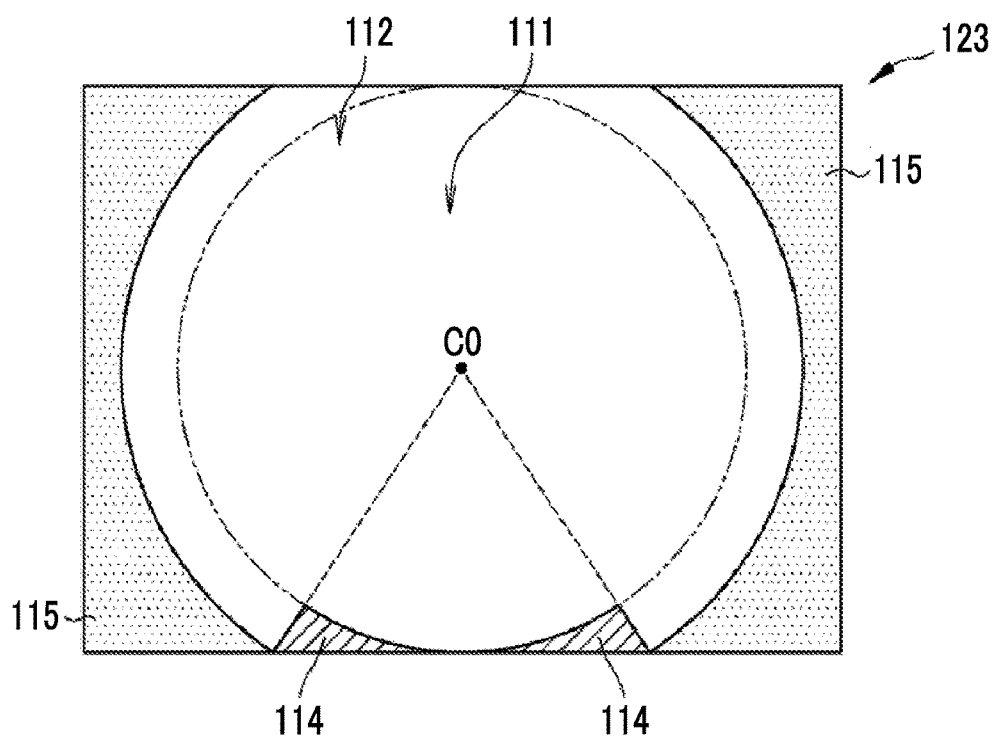
FIG. 9 shows a display image in a direct-viewing enlargement mode.

In a case in which a display mode is set to the direct-viewing enlargement mode, the display control section 98 generates a display image 123 shown in FIG. 9 and displays the display image 123 on the monitor 18. Specifically, in a case in which the display control section 98 generates the display image 123 in the direct-viewing enlargement mode, the display control section 98 enlarges the direct-viewing observation image 111 by the display image generating unit 102 and compresses the side-viewing observation image 112 in a radial direction while maintaining the size of the outer periphery of the side-viewing observation image 112. Then, the display control section 98 generates the display image 123 by connecting the outer periphery of the direct-viewing observation image 111 to the inner periphery of the side-viewing observation image 112 and masking the first and second blind spot portions 114 and 115.

Accordingly, a display range (the range of an object to be observed, which can be displayed on the monitor 18, with respect to the entire object to be observed) and a display area (the area of a portion of the monitor 18 displaying the object to be observed) of the object to be observed in the display image 123 in the direct-viewing enlargement mode are the same as those in the display image 113 in the standard mode, but the display image 123 in the direct-viewing enlargement mode has a relatively large display ratio of the direct-viewing observation image 111 to the side-viewing observation image 112 in the display range and the display area of the object to be observed. For this reason, in a case in which a display mode is set to the direct-viewing enlargement mode, a doctor or the like can observe an object to be observed in a wide range by the direct-viewing observation image 111 and the side-viewing observation image 112 and particularly easily observes the object to be observed shown up in the direct-viewing observation image 111. For example, if a display mode is set to the direct-viewing enlargement mode in a case in which a portion to be noted, such as a portion suspected as a lesion, is discovered in the tip direction of the insertion part 12a, a doctor or the like can observe the portion to be noted in more detail.

Figure 10:
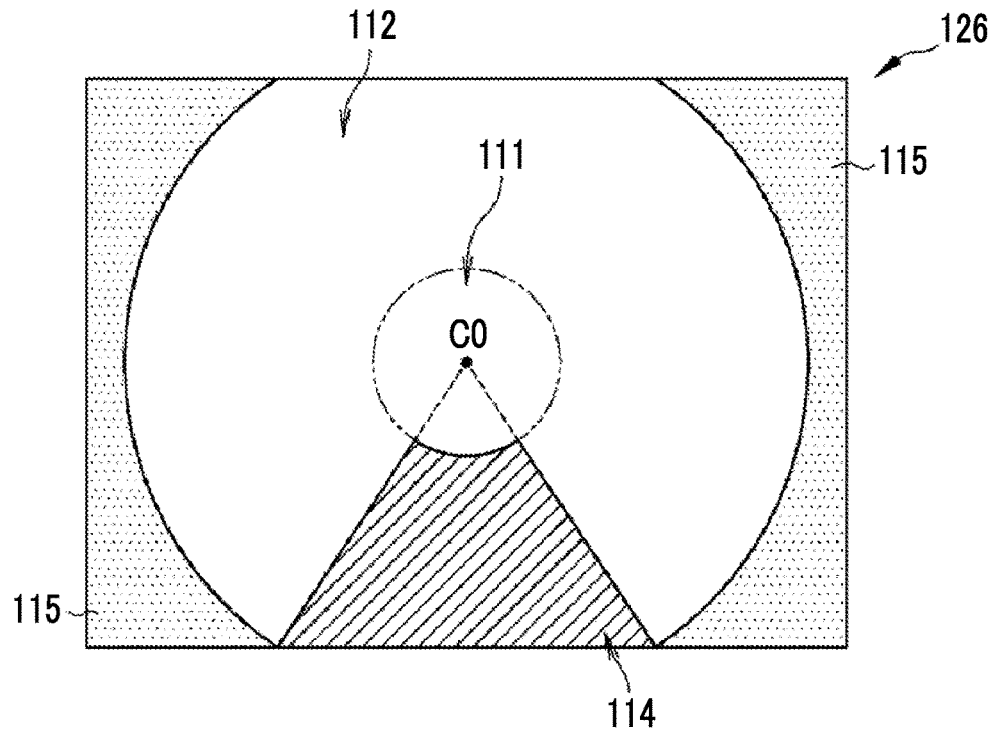
FIG. 10 shows a display image in a side-viewing enlargement mode.

Further, in a case in which a display mode is set to the side-viewing enlargement mode, the display control section 98 generates a display image 126 shown in FIG. 10 and displays the display image 126 on the monitor 18. Specifically, in a case in which the display control section 98 generates the display image 126 in the side-viewing enlargement mode, the display control section 98 enlarges the side-viewing observation image 112 in the radial direction by the display image generating unit 102. Specifically, the display control section 98 extends the side-viewing observation image 112 toward the inside (the side of the center C0) while maintaining the size of the outer periphery of the side-viewing observation image 112, and reduces the direct-viewing observation image 111 to a size corresponding to the inner periphery of the enlarged side-viewing observation image 112. Then, the display control section 98 generates the display image 126 by connecting the inner periphery of the enlarged side-viewing observation image 112 to the outer periphery of the reduced direct-viewing observation image 111 and masking the first and second blind spot portions 114 and 115.

Accordingly, a display range and a display area of the object to be observed in the display image 126 in the side-viewing enlargement mode are the same as those in the display image 113 in the standard mode, but the display image 126 in the side-viewing enlargement mode has a large display ratio of the side-viewing observation image 112 to the direct-viewing observation image 111 in the display range and the display area of the object to be observed. For this reason, in a case in which a display mode is set to the side-viewing enlargement mode, a doctor or the like can observe an object to be observed in a wide range by the direct-viewing observation image 111 and the side-viewing observation image 112 and particularly easily observes the object to be observed shown up in the side-viewing observation image 112. For example, if a display mode is set to the side-viewing enlargement mode in a case in which a portion to be noted, such as a portion suspected as a lesion, is discovered in the lateral direction of the insertion part 12a, a doctor or the like can observe the portion to be noted in more detail.

As described above, the endoscope system 10 has the direct-viewing enlargement mode and the side-viewing enlargement mode in which a relative display ratio of the direct-viewing observation image 111 and the side-viewing observation image 112 on the monitor 18 is adjusted. Further, in a case in which a display mode is switched to the direct-viewing enlargement mode or the side-viewing enlargement mode, an object to be observed, which is shown up in the direct-viewing observation image 111 or the side-viewing observation image 112, can be enlarged while the display range and the display area of an object to be observed are maintained. For this reason, the endoscope system 10 is more easily used for observation, diagnosis, or the like than in the related art.

Figure 11:
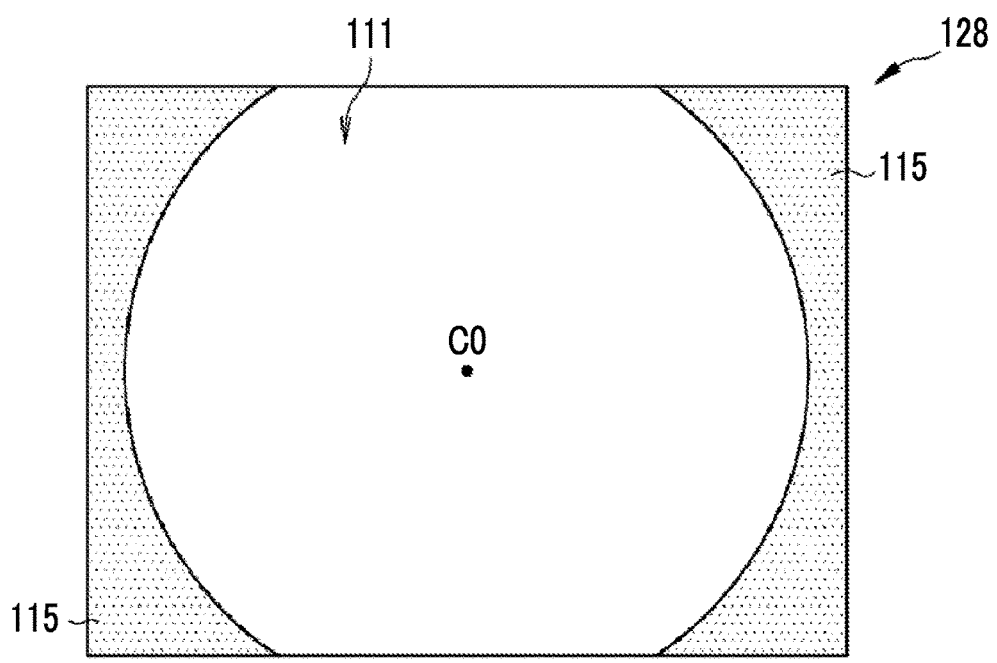
FIG. 11 shows a display image in a direct-viewing enlargement mode in which substantially only a direct-viewing observation image is displayed.

In the direct-viewing enlargement mode, for example, the display ratio of the direct-viewing observation image 111 can be set to 100% and the display ratio of the side-viewing observation image 112 can be set to 0%. In this case, a display image 128 in which substantially only the direct-viewing observation image 111 is displayed as shown in FIG. 11 can be generated and be displayed on the monitor 18. Accordingly, the endoscope system 10 can arbitrarily switch the display image 123 in the standard mode in which the direct-viewing observation image 111 and the side-viewing observation image 112 are displayed and the display image 128 in which substantially only the direct-viewing observation image 111 is displayed, as necessary; and can display the images on the monitor 18. The endoscope system 10 generates the display image 128 by fully enlarging the direct-viewing observation image 111 in a display range (the range from the center C0 to the outer periphery of the side-viewing observation image 112 of the display image 113 in the standard mode) and masking the second blind spot portion 115.

Figure 12:
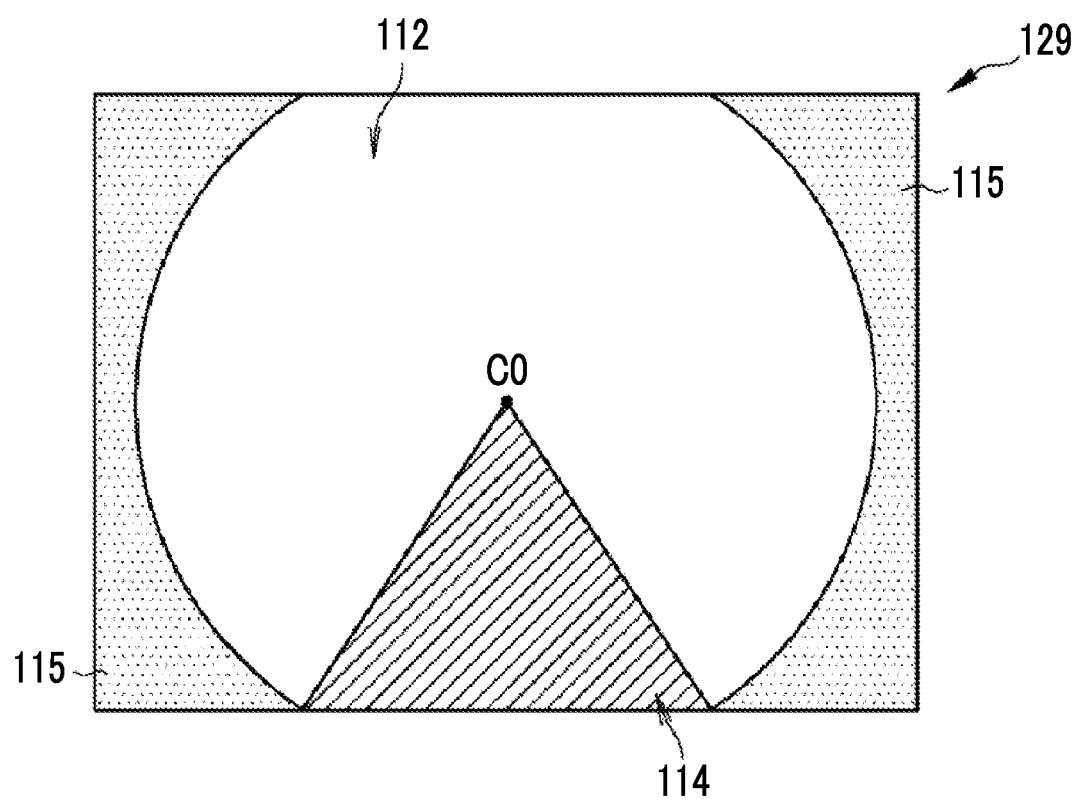
FIG. 12 shows a display image in a side-viewing enlargement mode in which substantially only a side-viewing observation image is displayed.

Further, in the side-viewing enlargement mode, for example, the display ratio of the side-viewing observation image 112 can be set to 100% and the display ratio of the direct-viewing observation image 111 can be set to 0%. In this case, a display image 129 in which substantially only the side-viewing observation image 112 is displayed as shown in FIG. 12 can be generated and be displayed on the monitor 18. Accordingly, the endoscope system 10 can arbitrarily switch the display image 123 in the standard mode in which the direct-viewing observation image 111 and the side-viewing observation image 112 are displayed and the display image 129 in which substantially only the side-viewing observation image 112 is displayed, as necessary; and can display the images on the monitor 18. The endoscope system 10 generates the display image 129 by extending the inner periphery of the side-viewing observation image 112 in the radial direction (a direction toward the center C0) while maintaining the size of the outer periphery of the side-viewing observation image 112 and masking the first and second blind spot portions 114 and 115.

Second Embodiment

Figure 13:
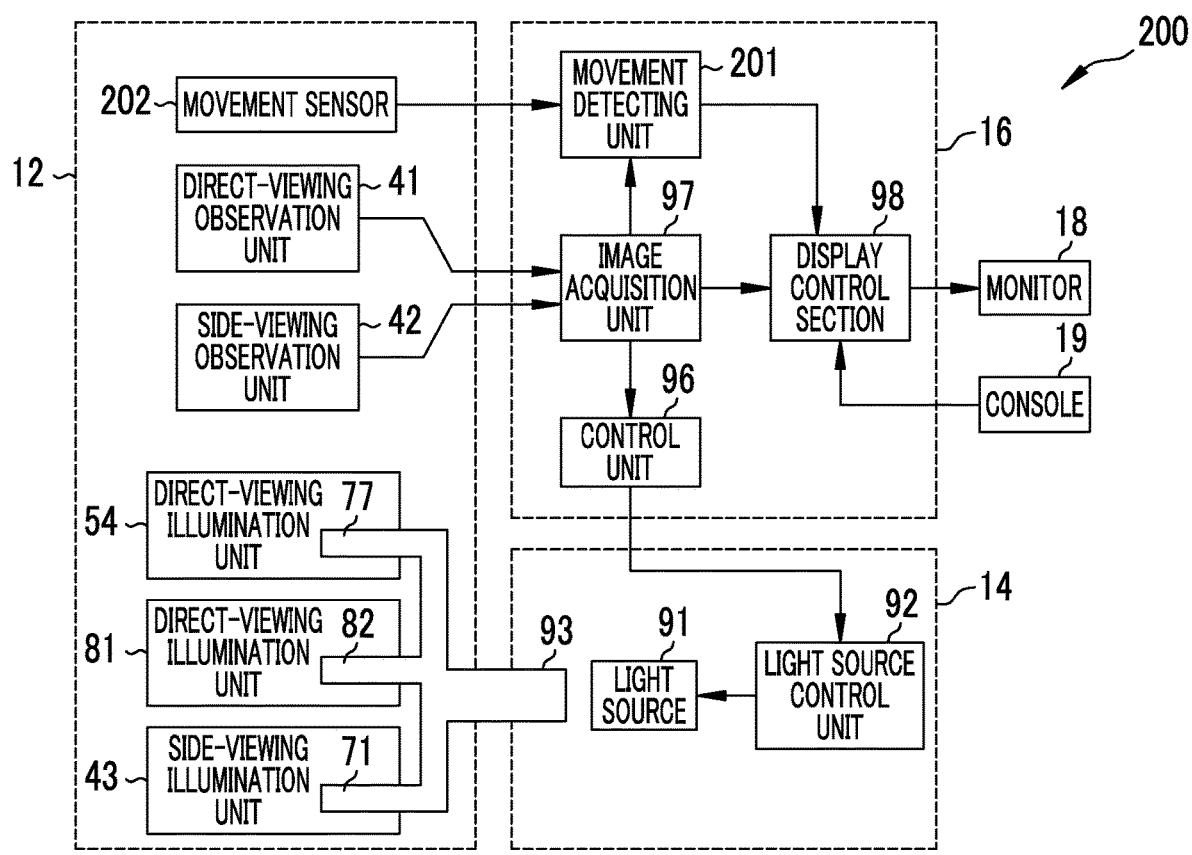
FIG. 13 is a block diagram of an endoscope system of a second embodiment.

In the first embodiment, a doctor or the like who is a user of the endoscope system 10 sets a relative display ratio of the direct-viewing observation image 111 in the direct-viewing enlargement mode and the side-viewing observation image 112 in the side-viewing enlargement mode. However, a relative display ratio of the direct-viewing observation image 111 in the direct-viewing enlargement mode and the side-viewing observation image 112 in the side-viewing enlargement mode can be automatically set. In this case, the processor device 16 is provided with a movement detecting unit 201 as in an endoscope system 200 shown in FIG. 13. Further, the endoscope 12 is provided with a movement sensor 202 as necessary.

The movement detecting unit 201 detects the movement of the tip part 12d of the insertion part 12a. The movement of the tip part 12d is the moving direction of the tip part 12d along an object to be observed, a change in the position (velocity, speed, or acceleration) of the tip part 12d in the moving direction of the tip part 12d along an object to be observed, the orientation of the tip part 12d caused by a bend of the bendable part 12c, the deflection angle of the tip part 12d caused by a bend of the bendable part 12c, a change in the orientation (angular speed or angular acceleration) of the tip part 12d caused by a bend of the bendable part 12c, or the like. The movement sensor 202 is a sensor for detecting the movement of the tip part 12d, and is, for example, a speed sensor, an acceleration sensor, an angular speed sensor, an angular acceleration sensor, a sensor or a mechanism for measuring the length of a portion of the insertion part 12a inserted into an object to be observed, a sensor or a mechanism for measuring the degree of a bend of the bendable part 12c, or the like.

For example, the movement detecting unit 201 acquires a plurality of direct-viewing observation images 111 and a plurality of side-viewing observation images 112 or any one of the plurality of direct-viewing observation images 111 and the plurality of side-viewing observation images 112 from an image acquisition unit 97 with time, and detects the movement of the tip part 12d by using the acquired direct-viewing observation images 111 or the acquired side-viewing observation images 112. Further, in a case in which the endoscope 12 is provided with the movement sensor 202, the movement of an object to be observed is detected using an output signal of the movement sensor 202 instead of the direct-viewing observation images 111 or the side-viewing observation images 112 or in addition to the direct-viewing observation images 111 or the side-viewing observation images 112.

Further, in a case in which the processor device 16 includes the movement detecting unit 201, the display control section 98 adjusts a relative display ratio of the direct-viewing observation image 111 and the side-viewing observation image 112 with reference to the movement of the tip part 12d detected by the movement detecting unit 201. That is, the display control section 98 automatically selects a display mode due to the movement of the tip part 12d, which is detected by the movement detecting unit 201, in the display ratio setting unit 101. Furthermore, in a case in which the automatically selected display mode is the direct-viewing enlargement mode or the side-viewing enlargement mode, the display control section 98 also automatically determines a relative display ratio of the direct-viewing observation image 111 and the side-viewing observation image due to the movement of the tip part 12d that is detected by the movement detecting unit 201.

Figure 14:
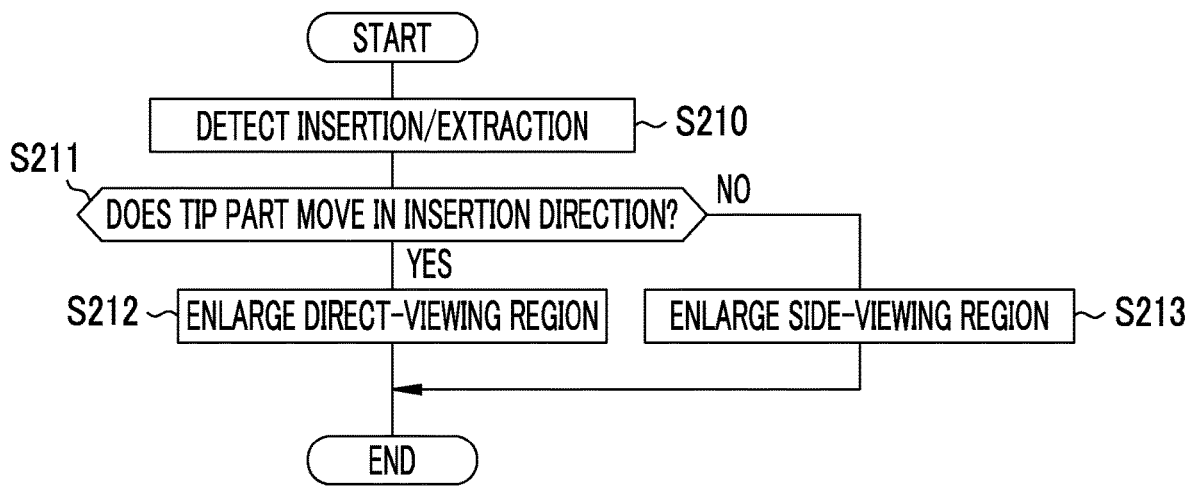
FIG. 14 is a flow chart illustrating the action of the second embodiment.
Figure 15:
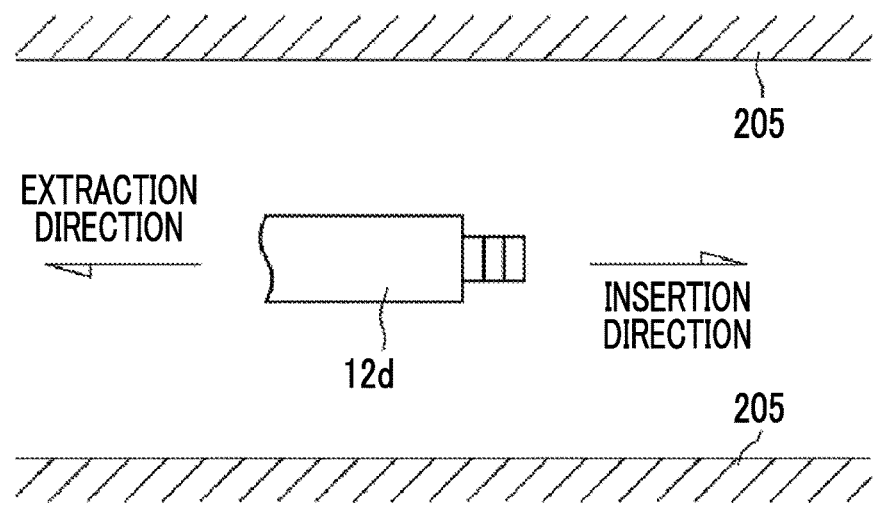
FIG. 15 is a diagram illustrating an insertion direction and an extraction direction.

In the endoscope system 200, for example, the display control section 98 can adjust a relative display ratio of the direct-viewing observation image 111 and the side-viewing observation image 112 in accordance with the insertion/extraction of the insertion part 12a. In this case, as shown in FIG. 14, the movement detecting unit 201 detects the insertion/extraction of the insertion part 12a, that is, whether the moving direction of the tip part 12*d* is an insertion direction or an extraction direction (S210). The insertion direction is the moving direction of the insertion part 12*a* or the like in a case in which the insertion part 12*a* is inserted into an object 205 to be observed as shown in FIG. 15, and is a direction in which the tip part 12*d* is moved to the back of the object 205 to be observed. The extraction direction is a direction opposite to the insertion direction, is the moving direction of the insertion part 12*a* or the like in a case in which the insertion part 12*a* is extracted from the object 205 to be observed along the object 205 to be observed, and is a direction in which the tip part 12*d* is moved to the front.

If the moving direction of the tip part 12*d* is the insertion direction (YES in S211), the display control section 98 automatically sets a display mode to the direct-viewing enlargement mode in the display ratio setting unit 101 (S212) and displays the display image 123 in the direct-viewing enlargement mode on the monitor 18. On the other hand, if the moving direction of the tip part 12*d* is the extraction direction (NO in S211), the display control section 98 automatically sets a display mode to the side-viewing enlargement mode in the display ratio setting unit 101 (S213) and displays the display image 126 in the side-viewing enlargement mode on the monitor 18.

In the endoscope system 200, as described above, a display mode is set to the direct-viewing enlargement mode in a case in which the insertion part 12*a* is to be inserted, and a display mode is set to the side-viewing enlargement mode in a case in which the insertion part 12*a* is to be extracted. Accordingly, the display ratio of an image, which is likely to be noted by a doctor or the like in a case in which the insertion part 12*a* is to be inserted or extracted, of the direct-viewing observation image 111 and the side-viewing observation image 112 on the monitor 18 is automatically increased. For this reason, the insertion part 12*a* of the endoscope system 200 is more easily inserted/extracted than an insertion part of the endoscope system in the related art that displays the direct-viewing observation image 111 and the side-viewing observation image 112.

Figure 16:
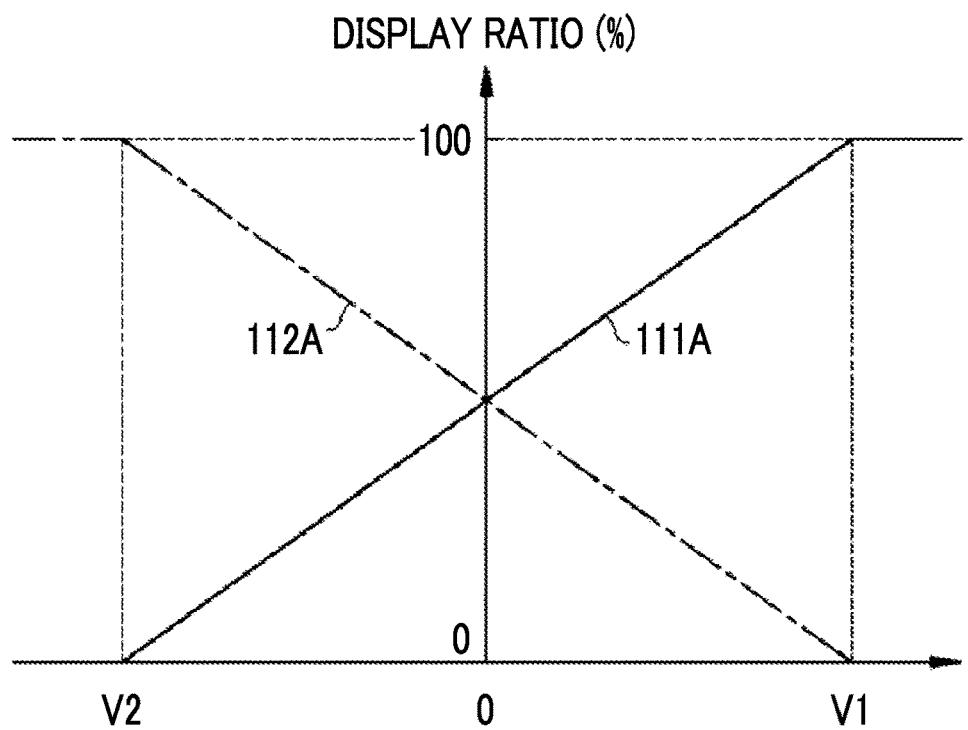
FIG. 16 is a graph showing a relative display ratio of a direct-viewing observation image and a side-viewing observation image.

In the second embodiment, the direct-viewing enlargement mode and the side-viewing enlargement mode are selected in accordance with the insertion/extraction of the insertion part 12*a*. However, in a case in which the movement detecting unit 201 detects the movement speed of the insertion part 12*a* (the tip part 12*d*) or the acceleration of movement of the insertion part 12*a* (the tip part 12*d*), a relative display ratio of the direct-viewing observation image 111 in the direct-viewing enlargement mode and the side-viewing observation image 112 in the side-viewing enlargement mode can be automatically set by additionally using the movement speed or acceleration of the insertion part 12*a* (the tip part 12*d*). For example, as shown in FIG. 16 by a graph 111A (solid line) representing the display ratio of the direct-viewing observation image 111 and a graph 112A (one-dot chain line) representing the display ratio of the side-viewing observation image 112, the display ratio of the direct-viewing observation image 111 is increased and the display ratio of the side-viewing observation image 112 is reduced according to the movement speed of the insertion part 12*a* in a case in which the movement speed of the insertion part 12*a* is positive and the insertion part 12*a* is moved in the insertion direction. That is, in a case in which the movement speed of the insertion part 12*a* is positive, a display mode is the direct-viewing enlargement mode and the display control section 98 generates the display image 123 in which the direct-viewing observation image 111 is enlarged so as to have a display ratio corresponding to the movement speed and displays the display image 123 on the monitor 18. In the range equal to or larger than a movement speed V1 (V1>0) at which the display ratio of the direct-viewing observation image 111 reaches 100%, the display control section 98 generates the display image 128 in which substantially only the direct-viewing observation image 111 is displayed and displays the display image 128 on the monitor 18.

On the other hand, in a case in which the movement speed of the insertion part 12*a* is negative and the insertion part 12*a* is moved in the extraction direction, the display ratio of the direct-viewing observation image 111 is reduced and the display ratio of the side-viewing observation image 112 is increased according to the movement speed of the insertion part 12*a*. That is, in a case in which the movement speed of the insertion part 12*a* is negative, a display mode is the side-viewing enlargement mode and the display control section 98 generates the display image 126 in which the side-viewing observation image is enlarged so as to have a display ratio corresponding to the movement speed and displays the display image 126 on the monitor 18. In the range equal to or smaller than a movement speed V2 (V2<0) at which the display ratio of the side-viewing observation image 112 reaches 100%, the display control section 98 generates the display image 129 in which substantially only the side-viewing observation image 112 is displayed and displays the display image 129 on the monitor 18.

In a case in which the insertion part 12*a* is not inserted and extracted, and the movement speed of the insertion part 12*a* is "0", a display mode is automatically set to the standard mode. For this reason, in a case in which the movement speed of the insertion part 12*a* is "0", the display control section 98 generates the display image 113 in the standard mode and displays the display image 113 on the monitor 18.

Considering not only the insertion/extraction of the insertion part 12*a* but also the movement speed (or acceleration) of the insertion part 12*a* during the insertion/extraction of the insertion part 12*a* as described above, the direct-viewing observation image 111 or the side-viewing observation image 112 can be appropriately enlarged and displayed in accordance with the more minute movement of the insertion part 12*a*. For this reason, even in a case in which the tip part 12*d* is moved by the movement of the insertion part 12*a* to more easily observe a portion to be noted during observation for diagnosis or the like in addition to an operation, which is to be performed before and after diagnosis or the like, such as the insertion or extraction of the insertion part 12*a*, the direct-viewing observation image 111 or the side-viewing observation image 112 can be enlarged and displayed in accordance with the movement of the tip part 12*d*.

The reason why the tip part 12*d* is moved in the insertion direction is that a portion to be noted is present in the tip direction, and the reason why the tip part 12*d* is moved in the extraction direction is that a portion to be noted is present in the lateral direction. Accordingly, in a case in which the direct-viewing enlargement mode or the side-viewing enlargement mode is automatically set as described above, an image, which includes a portion to be noted, of the direct-viewing observation image 111 and the side-viewing observation image 112 can be automatically enlarged and displayed. Further, in a case in which the insertion part 12*a* is quickly moved since a portion to be noted is present at a position distant from the current position of the tip part 12*d*, the direct-viewing observation image 111 or the side-viewing observation image 112 is enlarged so as to have a larger size. Accordingly, there is also an advantage that it is difficult to lose sight of a portion to be noted even though the insertion part 12a is quickly moved.

Figure 17:
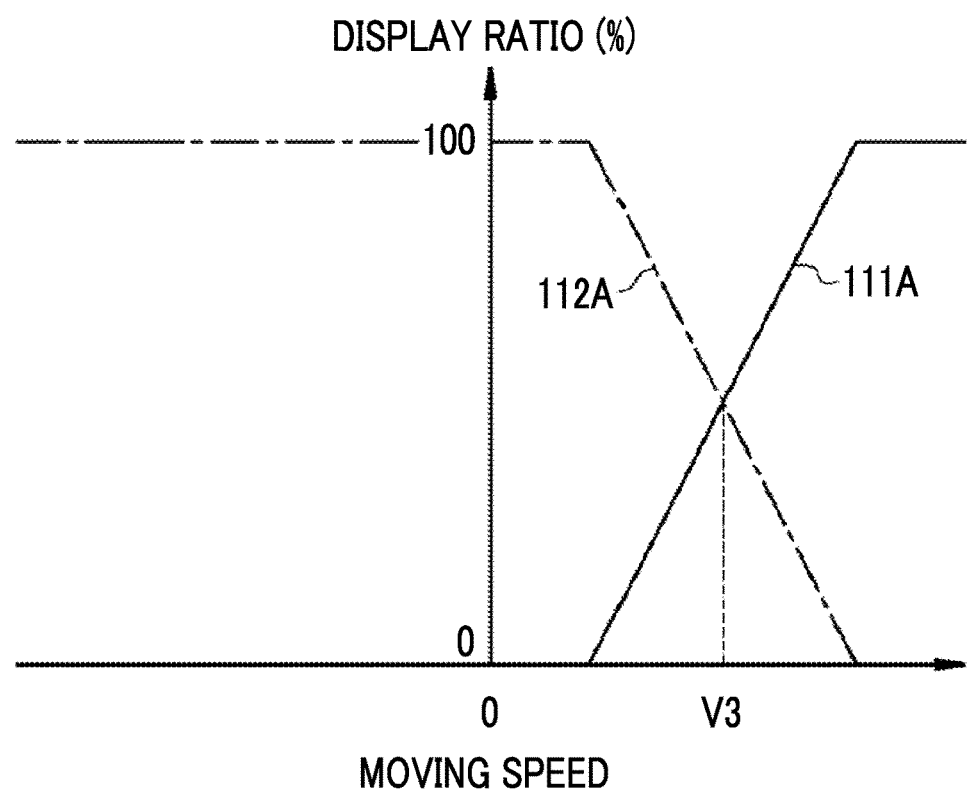
FIG. 17 is a graph showing a relative display ratio of the direct-viewing observation image and the side-viewing observation image.

In the modification example, a display mode is switched to the direct-viewing enlargement mode and the side-viewing enlargement mode due to the insertion/extraction of the insertion part 12a and the movement speed of the insertion part 12a is additionally used to switch a display mode. However, a display mode may be switched due to the movement speed of the insertion part 12a regardless of the moving direction of the insertion part 12a. For example, as shown in FIG. 17 by a graph 111A representing the display ratio of the direct-viewing observation image 111 and a graph 112A representing the display ratio of the side-viewing observation image 112, the direct-viewing enlargement mode and the side-viewing enlargement mode may be switched at a certain movement speed V3 (V3>0) as a boundary. Of course, likewise, the direct-viewing enlargement mode and the side-viewing enlargement mode may be switched at a negative movement speed as a boundary.

Figure 18:
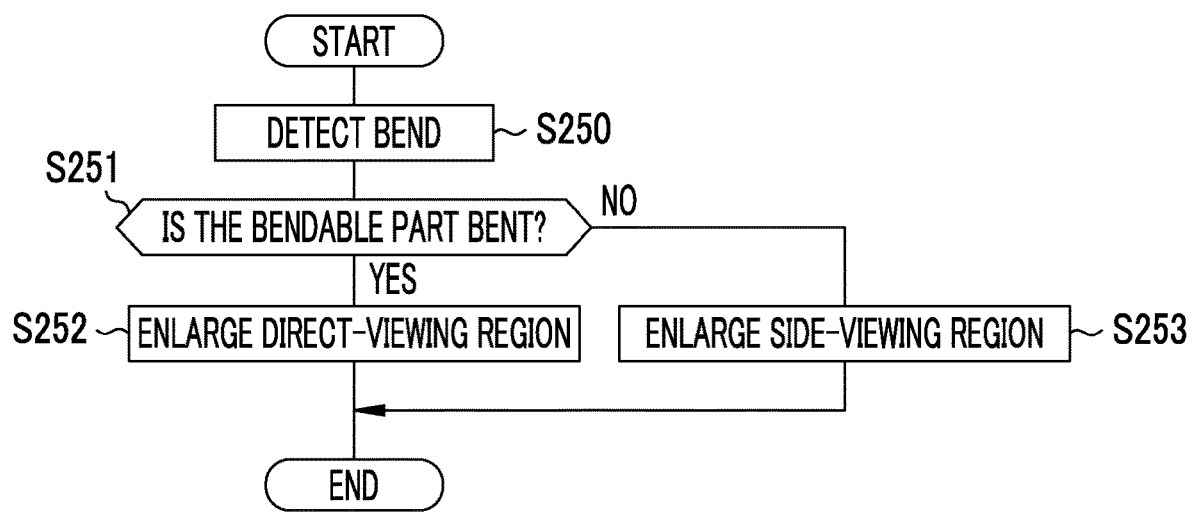
FIG. 18 is a flow chart of a modification example that detects a bend.
Figure 19:
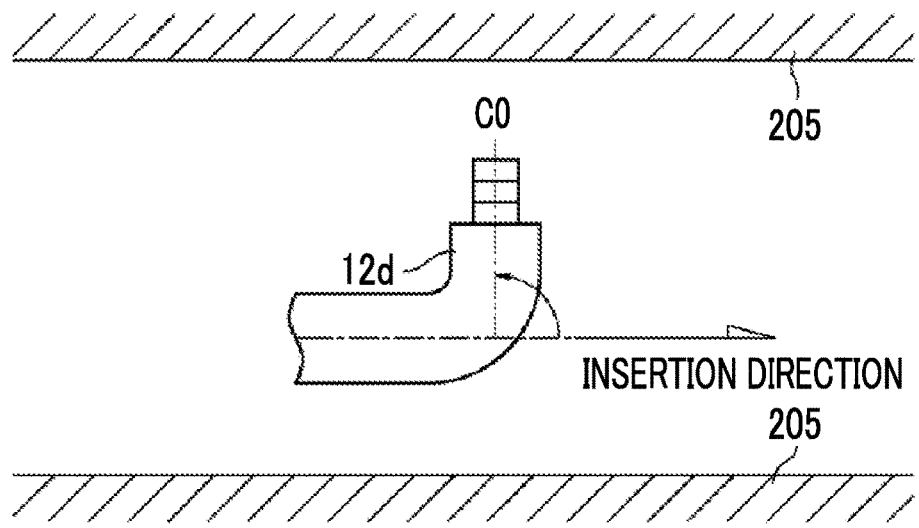
FIG. 19 is a diagram illustrating a case in which the orientation of the tip part is changed.
Figure 20:
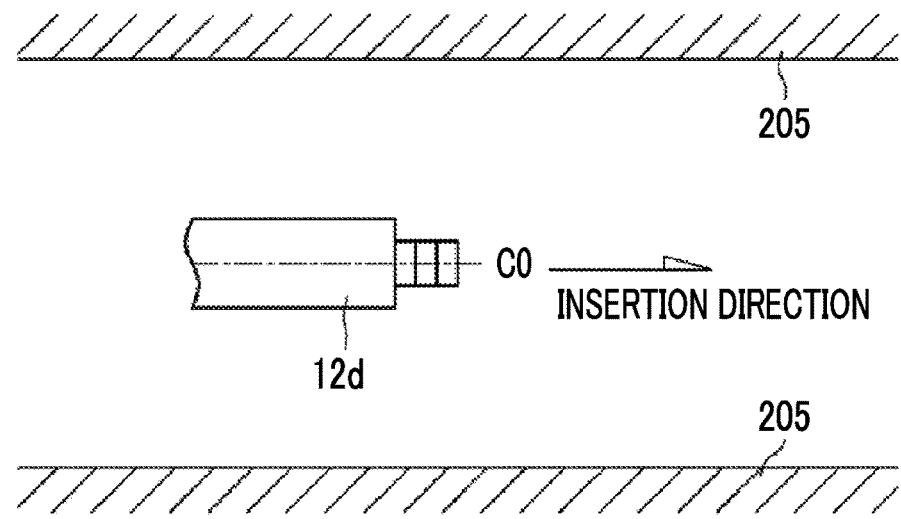
FIG. 20 is a diagram illustrating a case in which the tip part faces the insertion direction.

In the second embodiment, the direct-viewing enlargement mode and the side-viewing enlargement mode are selected in accordance with the insertion/extraction of the insertion part 12a. However, in a case in which the movement detecting unit 201 detects the orientation of the tip part 12d caused by a bend of the bendable part 12c, the display control section 98 can automatically select the direct-viewing enlargement mode and the side-viewing enlargement mode in accordance with the orientation of the tip part 12d caused by a bend of the bendable part 12c. Specifically, for example, as shown in FIG. 18, the movement detecting unit 201 detects the presence/absence of a bend of the bendable part 12c to detect the orientation of the tip part 12d (S250). If a bend of the bendable part 12c is detected (YES in S251), the display control section 98 automatically sets a display mode to the direct-viewing enlargement mode and enlarges and displays the direct-viewing observation image 111 (S252). In a case in which the bendable part 12c is bent and the orientation of the tip part 12d is changed as shown in FIG. 19, a portion to be noted is normally present in the tip direction of the tip part 12d. On the other hand, in a case in which the bendable part 12c is not bent and the tip part 12d faces the insertion direction, the display control section 98 automatically sets a display mode to the side-viewing enlargement mode and enlarges and displays the side-viewing observation image 112 (S253). In a case in which the bendable part 12c is not bent and the tip part 12d faces the insertion direction as shown in FIG. 20, there are many cases where a doctor or the like screens the presence/absence of a portion to be noted by using the side-viewing observation image 112.

In the above description, a display mode is automatically set to the side-viewing enlargement mode in a case in which the bendable part 12c is not bent and the tip part 12d faces the insertion direction, but a display mode may be automatically set to the standard mode in a case in which the bendable part 12c is not bent and the tip part 12d faces the insertion direction.

Figure 21:
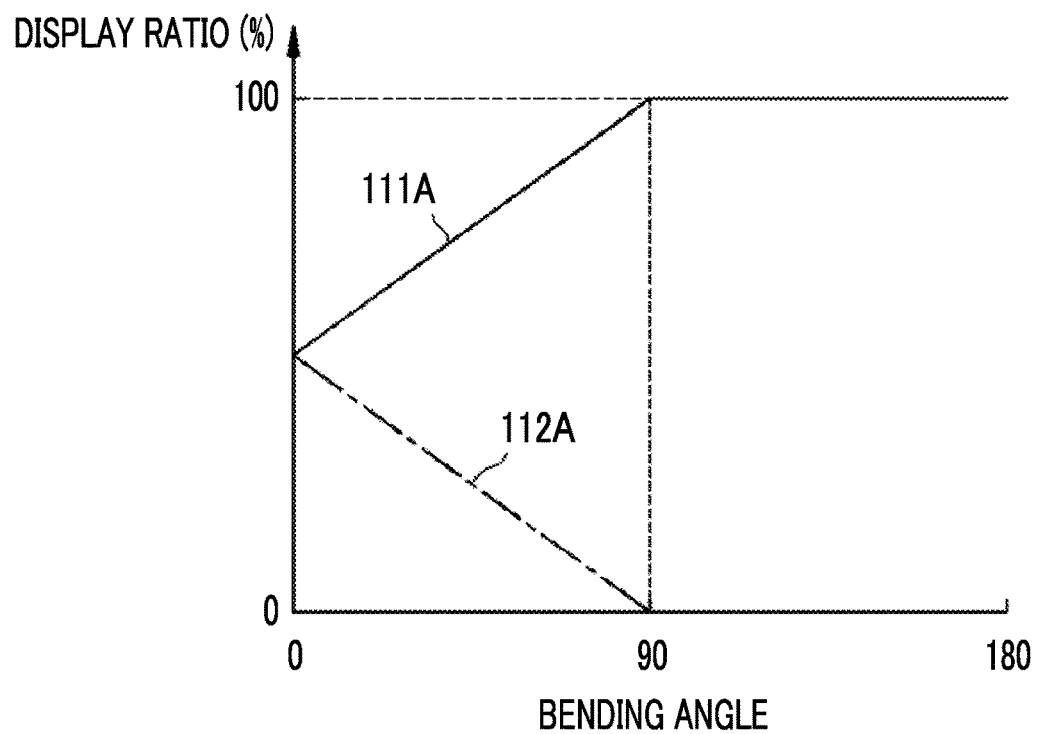
FIG. 21 is a graph showing a relative display ratio of the direct-viewing observation image and the side-viewing observation image.

Further, in a case in which the direct-viewing enlargement mode, the standard mode, or the side-viewing enlargement mode is switched in accordance with the orientation of the tip part 12d and the movement detecting unit 201 detects the bending angle, the bending speed, or the acceleration of the bendable part 12c, a relative display ratio of the direct-viewing observation image 111 in the direct-viewing enlargement mode and the side-viewing observation image 112 in the side-viewing enlargement mode can be automatically set by using the bending angle, the bending speed, or the acceleration of the bendable part 12c. For example, as shown in FIG. 21 by a graph 111A representing the display ratio of the direct-viewing observation image 111 and a graph 112A representing the display ratio of the side-viewing observation image 112, a display mode is automatically set to the standard mode in a case in which the bending angle is 0° and a display mode is automatically set to the direct-viewing enlargement mode in a case in which the bending angle is larger than 0°. Further, in a case in which the bending angle is larger than 0° and is 90° or less, the display control section 98 sets a relative display ratio of the direct-viewing observation image 111 and the side-viewing observation image 112 in accordance with the bending angle. In this case, the direct-viewing observation image 111 can be enlarged to an appropriate size according to a more minute change in the orientation of the tip part 12d, and can be displayed.

In a case in which the bending angle is larger than 90°, the tip part 12d faces the rear side. In this case, since a portion to be noted in diagnosis or the like is likely to be present at a portion where the tip part 12d faces, it is good for the display control section 98 to generate the display image 128 in which substantially only the direct-viewing observation image 111 is displayed and to display the display image 128 on the monitor 18 (see FIG. 21). However, in a case in which the bending angle is larger than 90°, the display ratio of the direct-viewing observation image 111 may be reduced according to the bending angle and the display ratio of the side-viewing observation image 112 may be increased as shown in FIG. 22.

Figure 22:
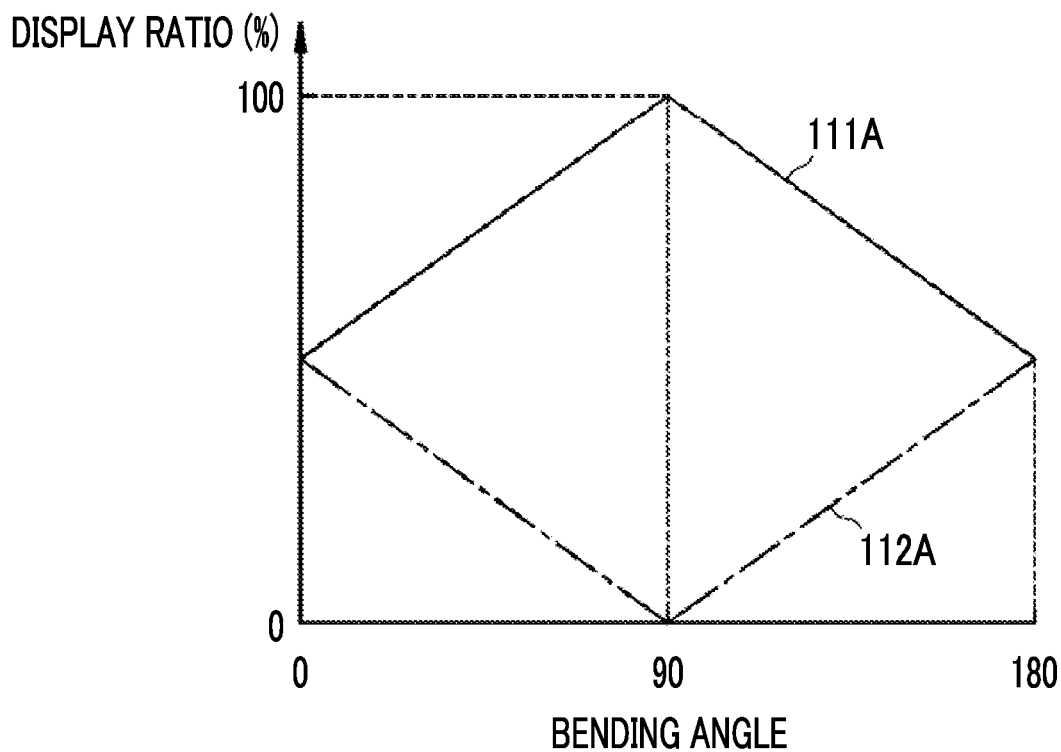
FIG. 22 is a graph showing a relative display ratio of the direct-viewing observation image and the side-viewing observation image.

Furthermore, FIGS. 21 and 22 show examples in which the display ratio of the side-viewing observation image 112 does not exceed the display ratio of the direct-viewing observation image 111 and the direct-viewing enlargement mode and the standard mode are switched. However, if the graph 111A and the graph 112A cross each other so that a portion at which the display ratio of the side-viewing observation image 112 exceeds the display ratio of the direct-viewing observation image 111 is formed, a display mode can be switched to the direct-viewing enlargement mode and the side-viewing enlargement mode.

Third Embodiment

In the first and second embodiments, the first blind spot portion 114 is masked and the first blind spot portion 114 is also reduced or enlarged in a case in which the side-viewing observation image 112 is reduced or enlarged in the direct-viewing enlargement mode or the side-viewing enlargement mode. For this reason, in the first and second embodiments, a portion of the side-viewing observation image 112 at which an object to be observed is shown up (a portion of the side-viewing observation image 112 except for the first and second blind spot portions 114 and 115) and the first blind spot portion 114 keep a relatively constant relationship between the sizes thereof before and after the reduction or enlargement. However, the first blind spot portion 114 and the portion of the side-viewing observation image 112 at which an object to be observed is shown up may not keep a constant relationship between the sizes thereof.

Figure 23:
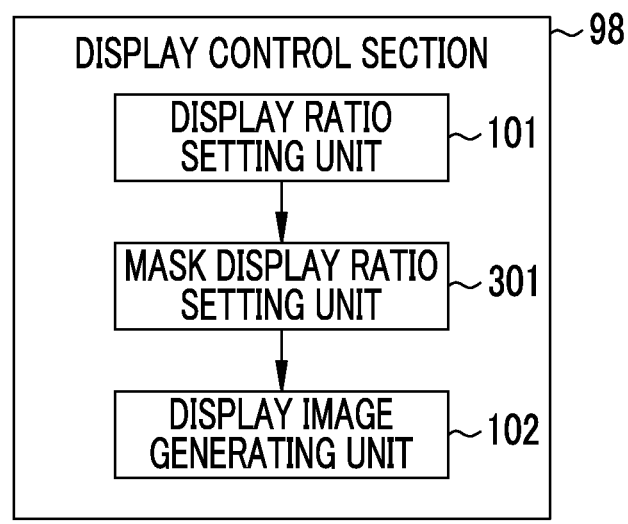
FIG. 23 is a block diagram of a display control section of a third embodiment.

For example, the first blind spot portion 114 can be reduced as necessary, so that the display area of the first blind spot portion 114 can be reduced. In this case, as shown in FIG. 23, the display control section 98 is provided with a mask display ratio setting unit 301 in addition to the display ratio setting unit 101 and the display image generating unit 102. The mask display ratio setting unit 301 changes a relative display ratio of the side-viewing observation image 112 and a mask, which covers the first blind spot portion 114, in accordance with a relative display ratio of the direct-viewing observation image 111 and the side-viewing observation image 112 that is set by the display ratio setting unit 101.

Figure 24:
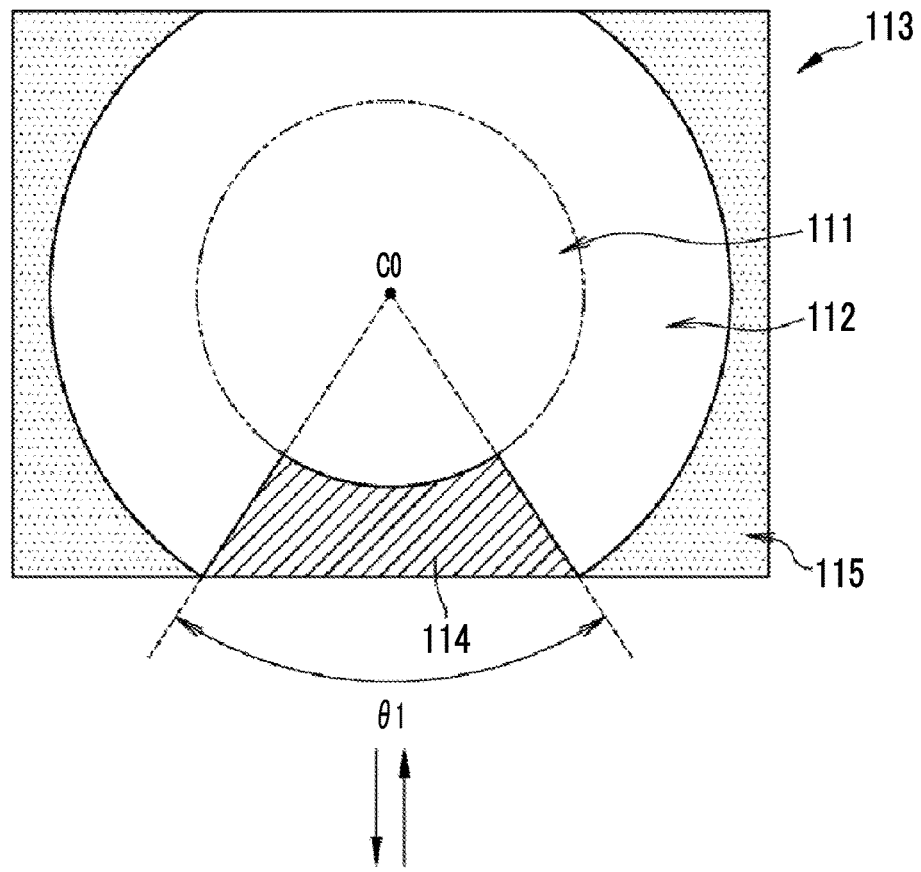
FIG. 24 is a diagram illustrating the reduction of a first blind spot portion.
Figure 24:
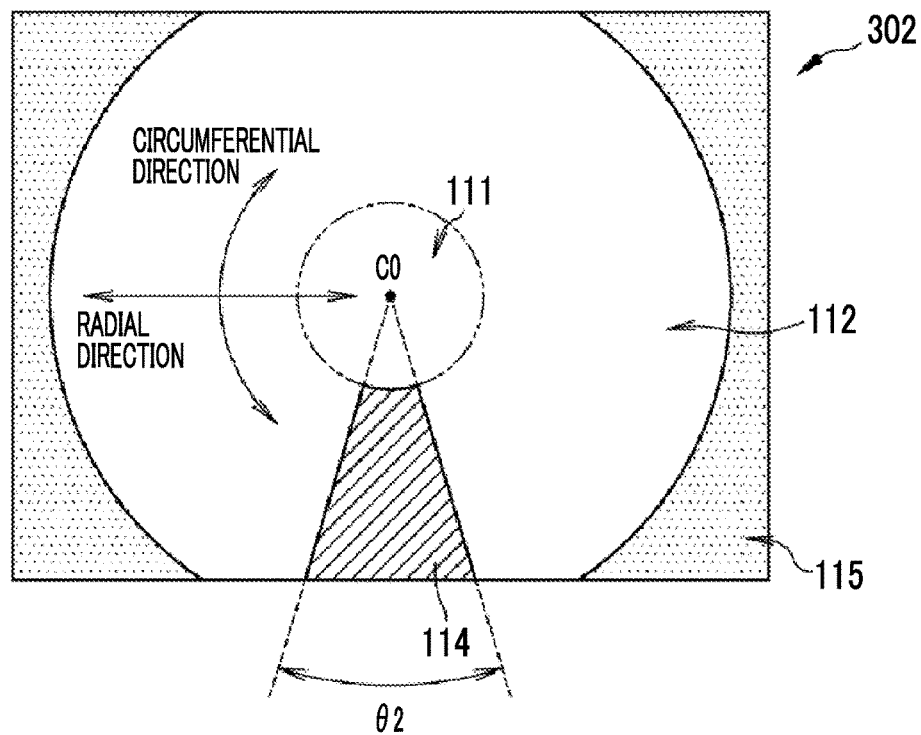

Specifically, for example, the first blind spot portion 114 of the display image 113 in the standard mode is a range that has a center C0 and an angle θ1 as shown in FIG. 24. Further, the display ratio setting unit 101 sets a display ratio in the side-viewing enlargement mode. Accordingly, first, the display image generating unit 102 reduces or enlarges the direct-viewing observation image 111 and the side-viewing observation image 112 in the radial direction around the center C0 to adjust a relative display ratio of the direct-viewing observation image 111 and the side-viewing observation image 112 to a display ratio that is set by the display ratio setting unit 101. This is the same as those in the first embodiment and the like.

In this embodiment, the mask display ratio setting unit 301 sets the range of the first blind spot portion 114, which has a center C0, to an angle θ2, which is smaller than at least the angle θ1, in the side-viewing enlargement mode. In a case in which the mask display ratio setting unit 301 sets the range of the first blind spot portion 114 to the angle θ2 in this way, the display image generating unit 102 further extends or compresses the direct-viewing observation image 111 and the side-viewing observation image 112 in a circumferential direction after reducing or enlarging the direct-viewing observation image 111 and the side-viewing observation image 112 in the radial direction as described above. Specifically, the display image generating unit 102 compresses a range, which has the angle θ1 and in which the first blind spot portion 114 is present, of the direct-viewing observation image 111 and the side-viewing observation image 112 in the circumferential direction and extends other portions thereof in the circumferential direction. Accordingly, the display image generating unit 102 allows the first blind spot portion 114 to be within the angle θ2. As a result, the display image generating unit 102 generates a display image 302 in which a relative display ratio of the mask covering the first blind spot portion 114 is reduced with respect to the side-viewing observation image 112, and displays the display image 302 on the monitor 18.

For example, in comparison with the display image 126 (see FIG. 10) in the side-viewing enlargement mode of the first embodiment, the display area of the first blind spot portion 114 and the display area of the mask, which covers the first blind spot portion 114, of the display image 302 are small and the display area of the other portion of the display image 302 in which an object to be observed is shown up is large. Therefore, according to the display image 302, an object to be observed can be displayed so as to be more easily observed.

In a case in which the display image 302 is to be generated, the reason why portions, which are present within the angle θ1, of not only the side-viewing observation image 112 but also the direct-viewing observation image 111 are compressed in the circumferential direction and portions thereof, which are present outside the angle θ1, are extended in the circumferential direction is to prevent deviation from being generated in the image of an object to be observed at a boundary between the direct-viewing observation image 111 and the side-viewing observation image 112. Further, the reason why the display area of the first blind spot portion 114 is reduced by the compression of the image and the display area of the other portion at which an object to be observed is shown up is increased by the enlargement of the image in the side-viewing enlargement mode is that, in the side-viewing enlargement mode, the display area of the first blind spot portion 114 is likely to be increased on the monitor 18 and an object to be observed is likely to be not easily observed since the first blind spot portion 114 not contributing to diagnosis or the like is likely to stand out even though being masked.

In the third embodiment, as an example, the first blind spot portion 114 is reduced and the other portion at which an object to be observed is shown is enlarged in the side-viewing enlargement mode. However, in the direct-viewing enlargement mode or the standard mode, the first blind spot portion 114 may be reduced and the other portion at which an object to be observed is shown up may be enlarged. In addition, in the side-viewing enlargement mode, the direct-viewing enlargement mode, or the standard mode, the first blind spot portion 114 may be enlarged and the other portion at which an object to be observed is shown up may be reduced.

Figure 25:
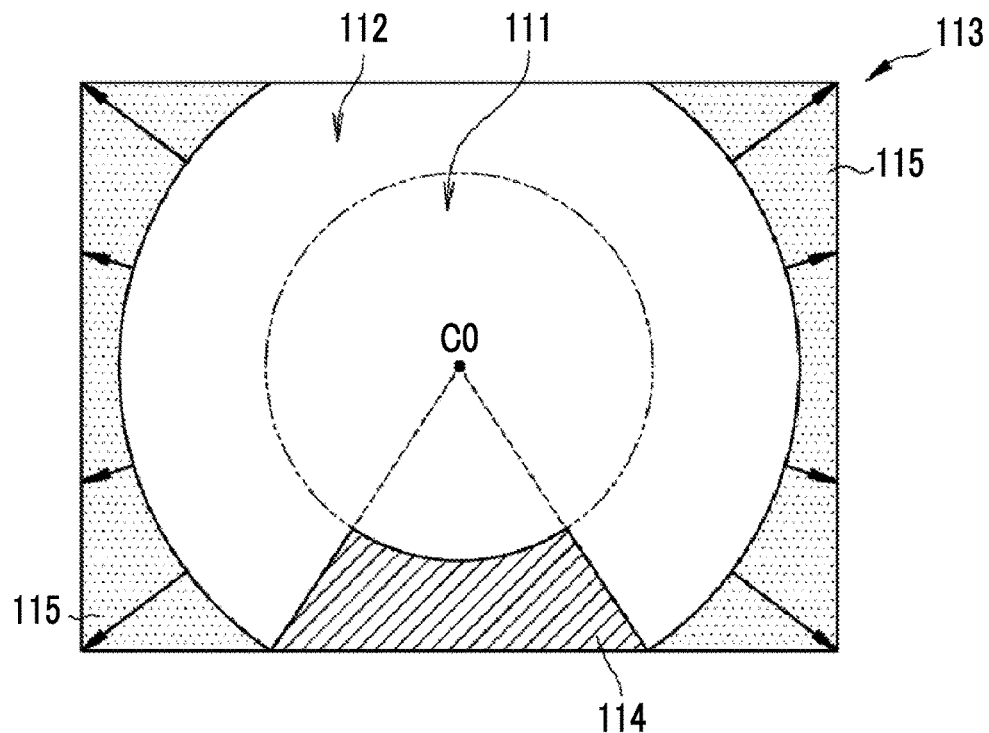
FIG. 25 is a diagram illustrating the reduction of a second blind spot portion.
Figure 26:
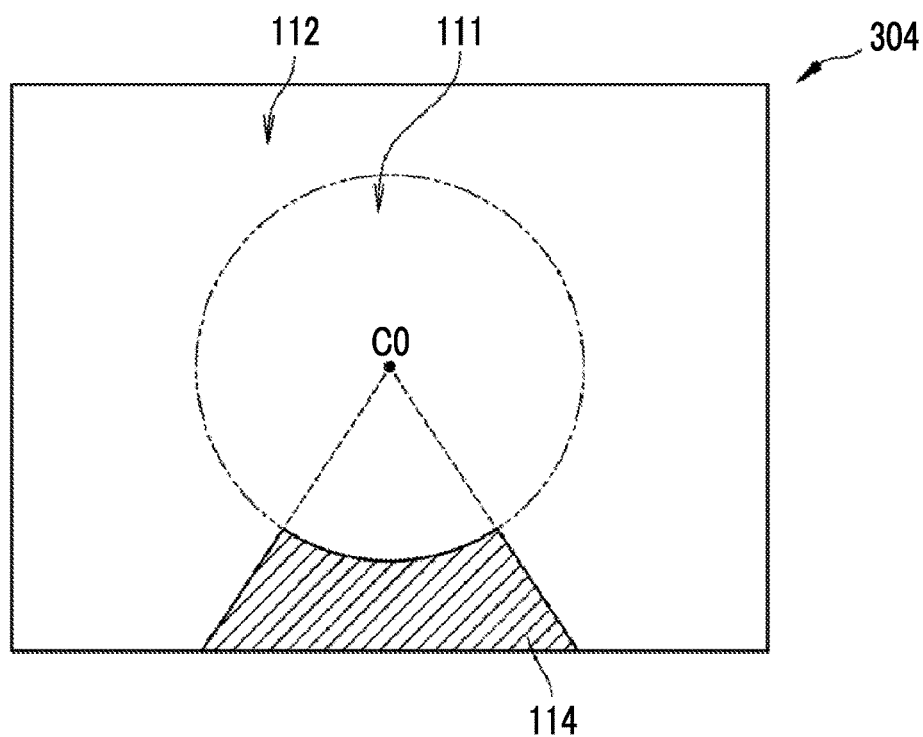
FIG. 26 shows a display image in which the second blind spot portion is reduced not to be displayed.

In the third embodiment, the first blind spot portion 114 is reduced but the second blind spot portion 115 can be reduced. In this case, the mask display ratio setting unit 301 sets whether to enlarge the outer periphery of the side-viewing observation image 112 in the radial direction. For example, as shown in FIG. 25 by arrows extending from the outer periphery of the side-viewing observation image 112, the mask display ratio setting unit 301 performs setting for enlarging the outer periphery of the side-viewing observation image 112 in the radial direction. In this case, the display image generating unit 102 enlarges or reduces the direct-viewing observation image 111 and the side-viewing observation image 112 in accordance with the display ratio that is set by the display ratio setting unit 101. In addition, the display image generating unit 102 increases the display area of the side-viewing observation image 112 by extending the side-viewing observation image 112 in the radial direction. As a result, the display image generating unit 102 generates a display image 304 in which the second blind spot portion 115 is not present as shown in, for example, FIG. 26, and displays the display image 304 on the monitor 18. Since an object to be observed can be displayed over the entire display range on the monitor 18 in a case in which the display image 304 in which the second blind spot portion 115 is not present is generated and displayed as described above, the object to be observed is more easily observed.

The non-display of the second blind spot portion 115 of the modification example can be performed in all the cases of the direct-viewing enlargement mode, the side-viewing enlargement mode, and the standard mode. Accordingly, the non-display of the second blind spot portion 115 of the modification example can be performed in one or two or more display modes selected from the direct-viewing enlargement mode, the side-viewing enlargement mode, and the standard mode. Further, the non-display of the second blind spot portion 115 of the modification example can be performed instead of the reduction or enlargement of the first blind spot portion 114 of the third embodiment or in addition to the reduction or enlargement of the first blind spot portion 114 of the third embodiment.

In addition, the second blind spot portion 115 is not displayed at all in the modification example, but the mask display ratio setting unit 301 can allow a part of the second blind spot portion 115 to remain in the display image 304 while reducing the display area of the second blind spot portion 115 by setting the display ratio of the second blind spot portion 115. In this case, as in the case of the reduction of the first blind spot portion 114 of the third embodiment, it is good that the reduction ratio of the display area of the second blind spot portion 115 is set in accordance with a relative display ratio of the direct-viewing observation image 111 and the side-viewing observation image 112. For example, in the side-viewing enlargement mode, the display area of the second blind spot portion 115 can be reduced in inverse proportion to the display ratio of the side-viewing observation image 112.

The angle θ1 corresponding to a range in which the first blind spot portion 114 is present is stored in the display control section 98 in advance, but it is preferable that the data of the angle θ1 is updatable. In calibration or the like, the value of the angle θ1 is adjusted on the basis of, for example, the visibility or the like of the nozzles 51 and 52 from the side-viewing observation unit 42. As a result, it is preferable that the size of a region masking as the first blind spot portion 114 can be adjusted. This applies to the first embodiment and the like.

Fourth Embodiment

Figure 27:
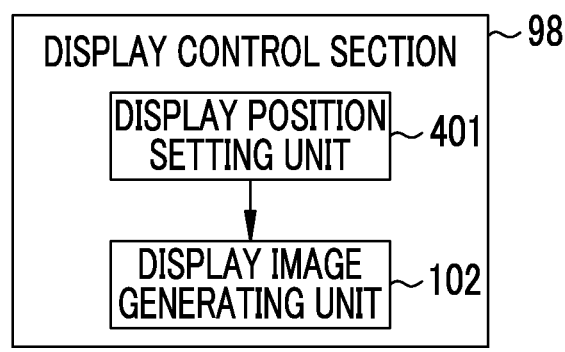
FIG. 27 is a block diagram of a display control section of a fourth embodiment.

In the first, second, and third embodiments, the direct-viewing observation image 111 and the side-viewing observation image 112 are displayed at the center of the display image (the display image 113 and the like). However, the display positions of the direct-viewing observation image 111 and the side-viewing observation image in each display image can be adjusted. In a case in which the display positions of the direct-viewing observation image 111 and the side-viewing observation image are to be adjusted, the display control section 98 is provided with a display position setting unit 401 as shown in FIG. 27. The display position setting unit 401 sets the display positions of the direct-viewing observation image 111 and the side-viewing observation image 112 in the display image. The display image generating unit 102 adjusts a display image to a position, which is set by the display position setting unit 401, and generates the display image.

Particularly, in a case in which the processor device 16 is provided with the movement detecting unit 201 of the second embodiment, the display position setting unit 401 can adjust the display position of the direct-viewing observation image 111 or the side-viewing observation image 112 in accordance with the movement detected by the movement detecting unit 201. Specifically, in a case in which the tip part 12d faces the insertion direction in the standard mode as shown in FIG. 28A, the display position setting unit 401 sets the display positions of the direct-viewing observation image 111 and the side-viewing observation image 112 to the center of a display image to be generated and displayed. For this reason, the display image generating unit 102 generates the display image 113 and displays the display image 113 on the monitor 18.

Figure 28B:
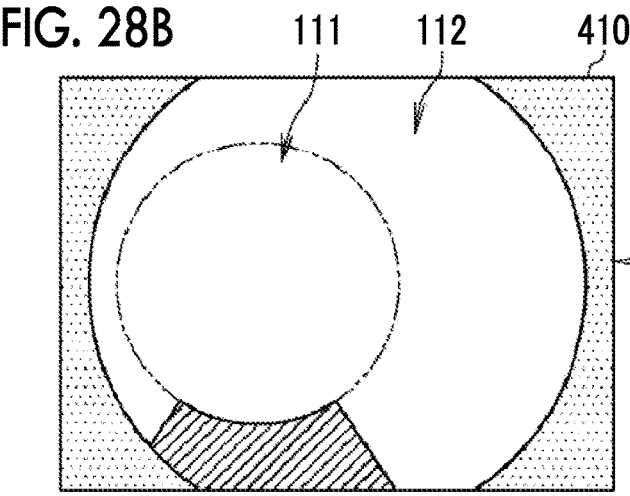
FIGS. 28A, 28B, and 28C are diagrams illustrating cases in which the display position of a direct-viewing observation image is adjusted in accordance with the orientation of the tip part.
Figure 28B:
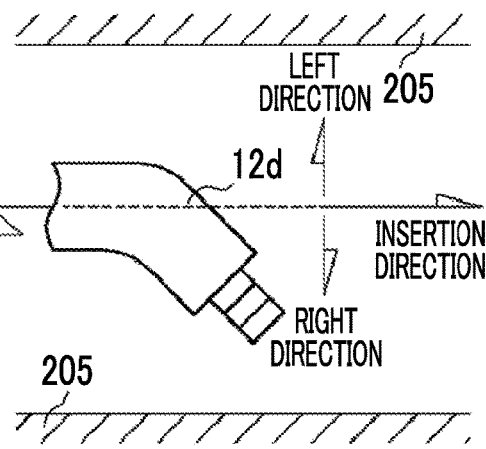
Figure 28A:
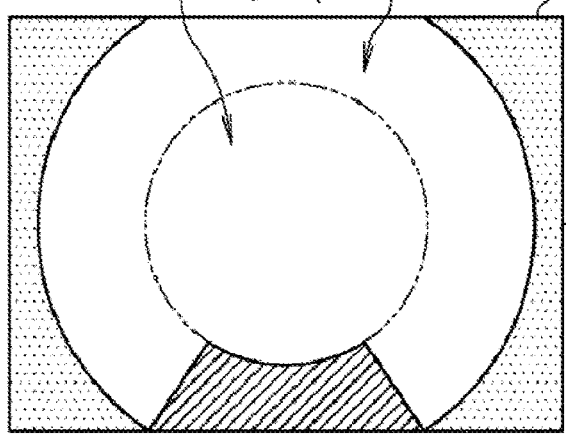
Figure 28A:
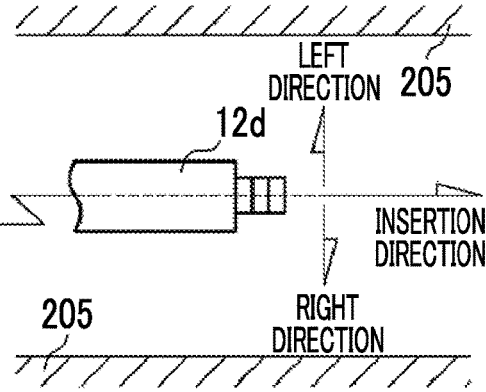

In a case in which the tip part 12d faces the right in the standard mode as shown in FIG. 28B, the display position setting unit 401 shifts the display position of the direct-viewing observation image 111 to the left in accordance with the orientation (angle) of the tip part 12d or the velocity, the speed, or the acceleration of the tip part 12d moving to the right. As a result, the display image generating unit 102 connects the direct-viewing observation image 111, which is displayed at the set position, to the side-viewing observation image 112, which is displayed at the set position, by extending or compressing the inner periphery of the side-viewing observation image 112 in accordance with the display position of the direct-viewing observation image 111. As a result, the display image generating unit 102 generates a display image 410 in which the display position of the direct-viewing observation image 111 is deviated to the left, and displays the display image 410 on the monitor 18. In a case in which the tip part 12d is made to face the right, a portion to be noted in diagnosis or the like is normally present on the right of the tip part 12d. Accordingly, in a case in which the display position of the direct-viewing observation image 111 is shifted to the left as described above and the right portion of the side-viewing observation image 112 is enlarged, the portion to be noted is easily observed.

Figure 28C:
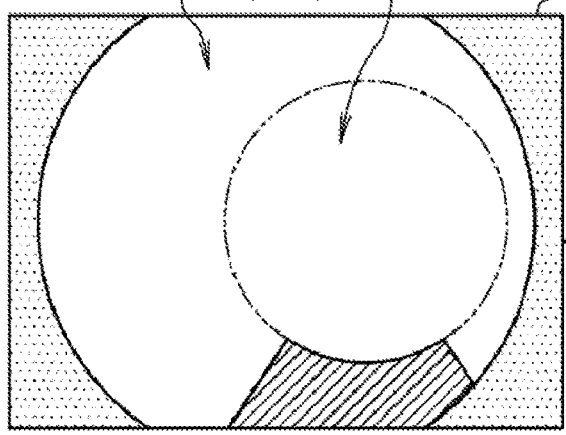
Figure 28C:
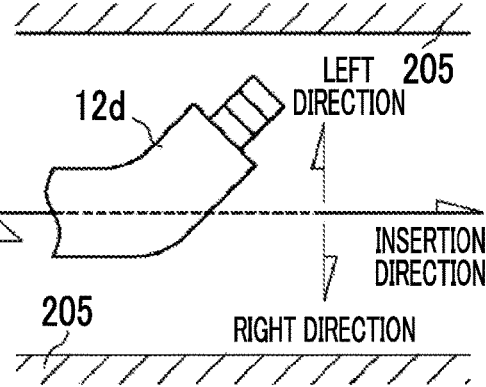

Further, in a case in which the tip part 12d faces the left in the standard mode as shown in FIG. 28C, the display position setting unit 401 shifts the display position of the direct-viewing observation image 111 to the right in accordance with the orientation (angle) of the tip part 12d or the velocity, the speed, or the acceleration of the tip part 12d moving to the left. Accordingly, in the same manner as described above, the display image generating unit 102 generates a display image 411 in which the display position of the direct-viewing observation image 111 is deviated to the right, and displays the display image 411 on the monitor 18. In a case in which the tip part 12d is made to face the left, a portion to be noted in diagnosis or the like is normally present on the left of the tip part 12d. Accordingly, in a case in which the direct-viewing observation image 111 is shifted to the right as described above and the left portion of the side-viewing observation image 112 is enlarged, the portion to be noted is easily observed. The same applies to a case in which the tip part is made to face the other side, such as the upper side or the lower side.

Figure 29B:
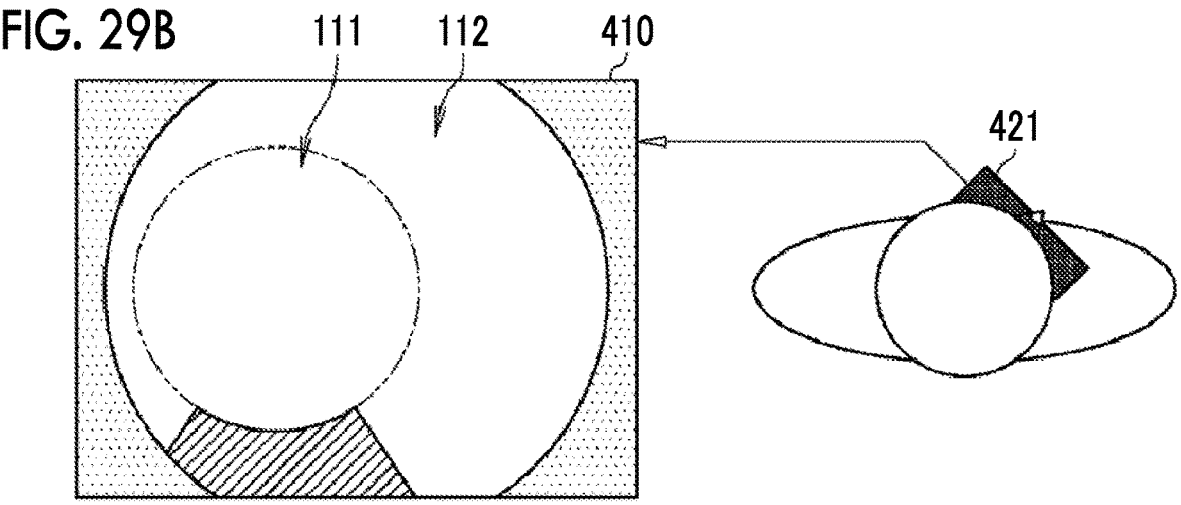
FIGS. 29A, 29B, and 29C are diagrams illustrating cases in which the display position of the direct-viewing observation image is adjusted in accordance with the orientation of a doctor or the like wearing a head mount display.
Figure 29A:
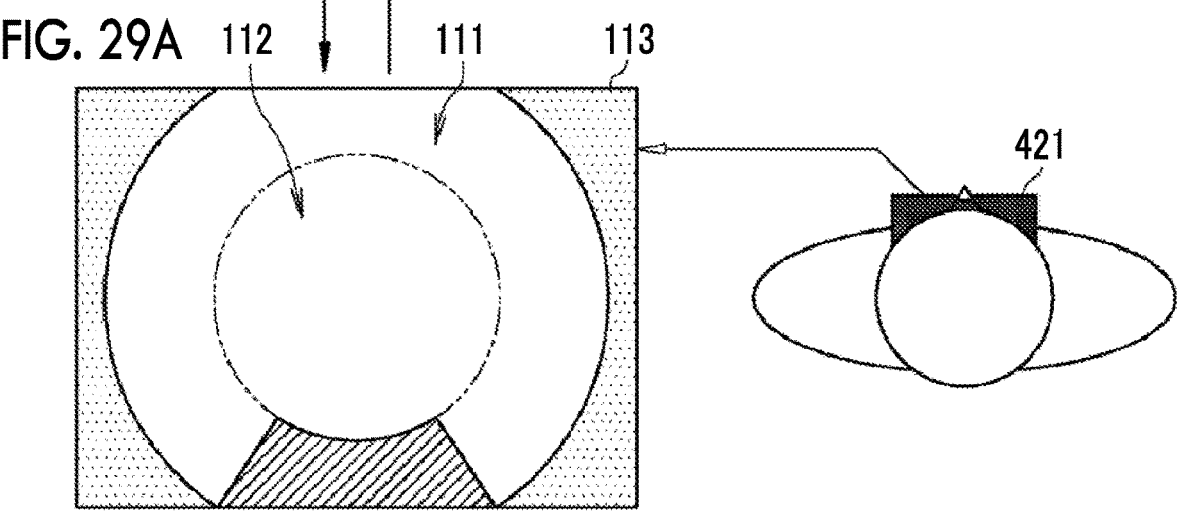
Figure 29C:
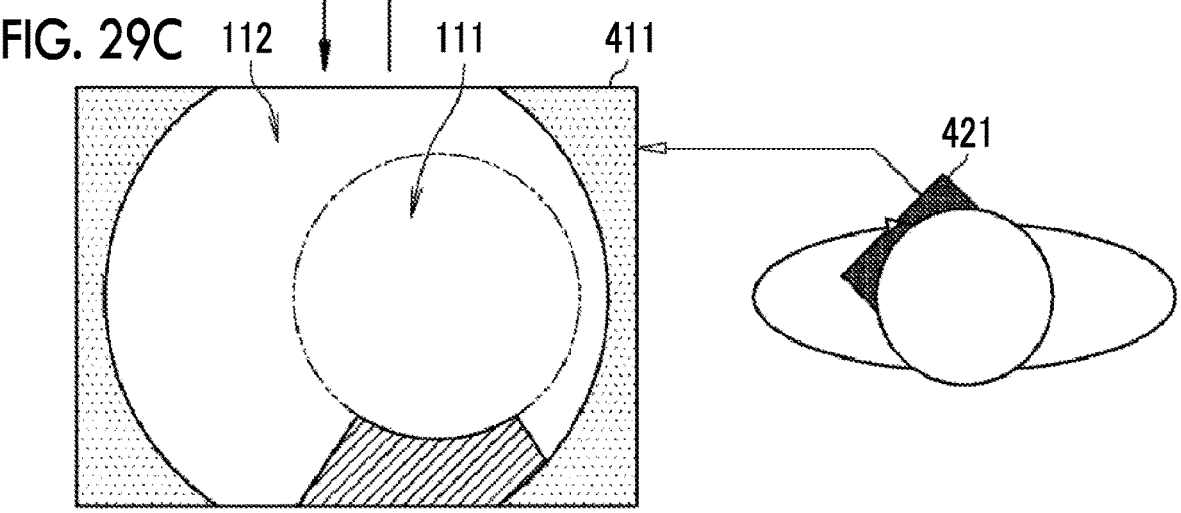

In the fourth embodiment, the display position of the direct-viewing observation image 111 is adjusted in accordance with the movement of the tip part 12d detected by the movement detecting unit 201. However, in a case in which the monitor 18 is a head mount display 421 as shown in FIGS. 29A, 29B, and 29C, the display position of the direct-viewing observation image 111 of the like can be adjusted in accordance with the movement of the head of a doctor or the like on which the head mount display 421 is worn. In this case, the movement detecting unit 201 detects the movement of the head mount display 421.

Further, in a case in which a doctor or the like wearing the head mount display 421 faces the front (the front of a wearer, such as a doctor, set by the calibration of the head mount display 421) in the standard mode, the display image 113 displayed at the center of the direct-viewing observation image 111 is displayed on the head mount display 421 (see FIG. 29A). In a case in which a doctor or the like wearing the head mount display 421 faces the right (the right of a wearer, such as a doctor, set by the calibration of the head mount display 421), the display image 410 in which the display position of the direct-viewing observation image 111 is deviated to the left is generated and is displayed on the head mount display 421 as in a case in which the tip part 12d faces the right in the fourth embodiment (see FIG. 29B). Furthermore, in a case in which a doctor or the like wearing the head mount display 421 faces the left (the left of a wearer, such as a doctor, set by the calibration of the head mount display 421), the display image 411 in which the display position of the direct-viewing observation image 111 is deviated to the right is generated and is displayed on the head mount display 421 as in a case in which the tip part 12d faces the left in the fourth embodiment (see FIG. 29C).

In the fourth embodiment, for simplification, a case in which a display mode is the standard mode has been described by way of example. However, the display position of the direct-viewing observation image 111 or the side-viewing observation image 112 can be adjusted even in the direct-viewing enlargement mode or the side-viewing enlargement mode. That is, the fourth embodiment can be arbitrarily combined with any one or more of the first, second, and third embodiments.

Fifth Embodiment

Figure 30:
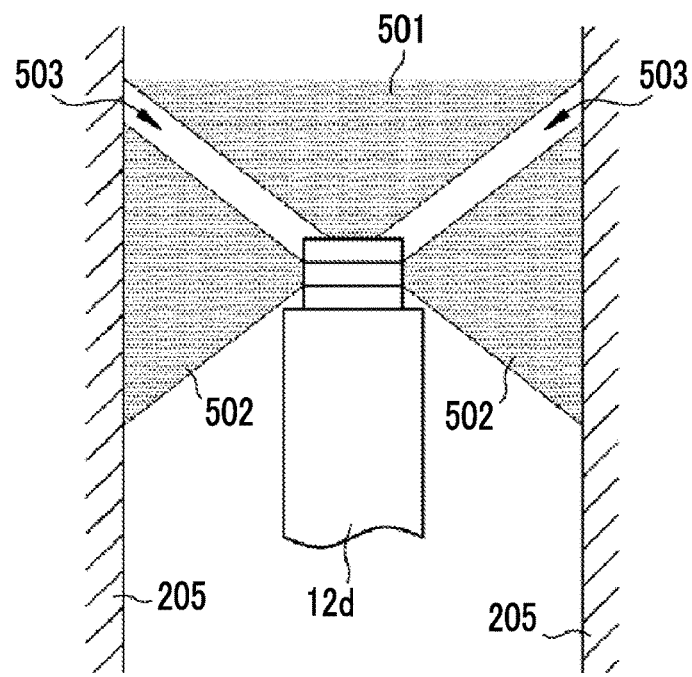
FIG. 30 is a diagram illustrating a blind spot between a direct-viewing observation unit and a side-viewing observation unit.

There is a case where other blind spots are present in the endoscopes 12 of each embodiment, such as the first embodiment, and the modification example thereof (hereinafter, referred to as the first embodiment and the like) in addition to a blind spot caused by the presence of the second protruding portion 32 and a blind spot formed outside the field of view of the side-viewing observation unit 42. Specifically, there is a case where a field 501 of view of the direct-viewing observation unit 41 and fields 502 of view of the side-viewing observation unit 42 do not overlap each other due to the performance of the image pickup lens 61 as shown in FIG. 30. In this case, blind spots 503, which are not included in both the field 501 of view of the direct-viewing observation unit 41 and the fields 502 of view of the side-viewing observation unit 42, may be present between the field 501 of view of the direct-viewing observation unit 41 and the fields 502 of view of the side-viewing observation unit 42. However, since the direct-viewing observation image 111 and the side-viewing observation image 112 are displayed so as to be connected to each other in the first embodiment and the like, a doctor or the like cannot visually recognize the presence of a portion to be noted on the monitor 18 in a case in which the portion to be noted is present in the blind spots 503 between the field 501 of view of the direct-viewing observation unit 41 and the fields 502 of view of the side-viewing observation unit 42. Accordingly, there is a possibility that the doctor or the like overlooks the portion to be noted. For this reason, it is preferable that the display control section 98 displays the presence of the blind spots 503 on the monitor 18 and informs a doctor or the like as a user of the presence of the blind spots 503.

Figure 31:
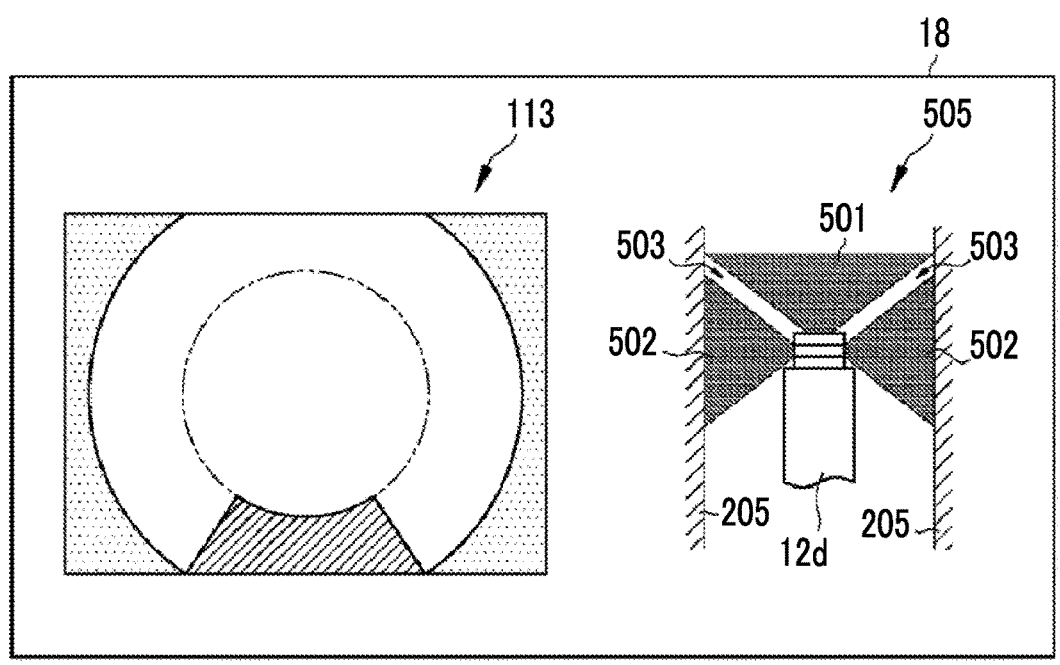
FIG. 31 shows a display screen of a monitor that displays a blind spot between the direct-viewing observation unit and the side-viewing observation unit.

For example, as shown in FIG. 31, the display control section 98 displays a schematic diagram 505 showing the presence of the blind spots 503 in addition to the display image of the first embodiment and the like, such as the display image 113. The schematic diagram 505 shows at least the field 501 of view of the direct-viewing observation unit 41, the fields 502 of view of the side-viewing observation unit 42, and the blind spots 503 between the field 501 of view of the direct-viewing observation unit 41 and the fields 502 of view of the side-viewing observation unit 42. In a case in which the display control section 98 displays the display image, such as the display image 113, and the schematic diagram 505 side by side (or so that the display image and the schematic diagram 505 are superimposed) on the monitor 18 as described above, a doctor or the like can perform diagnosis or the like with attention to the presence of the blind spots 503 displayed on the monitor 18 even though a display image, such as the display image 113 in which the direct-viewing observation image 111 and the side-viewing observation image 112 are connected to each other, is displayed on the monitor 18.

Figure 32:
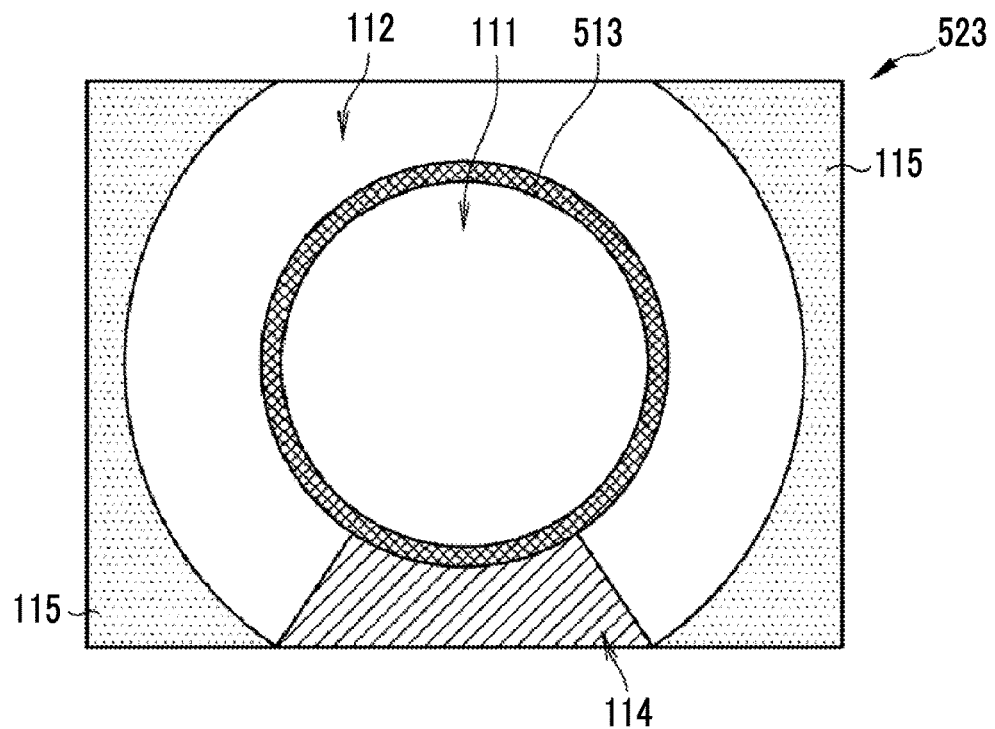
FIG. 32 shows a display image that displays a blind spot between the direct-viewing observation unit and the side-viewing observation unit.

The display control section 98 may display a message, which indicates the presence/absence of the blind spots 503, on the monitor 18 instead of the schematic diagram 505. Further, in a case in which the blind spots 503 are present between the field 501 of view of the direct-viewing observation unit 41 and the fields 502 of view of the side-viewing observation unit 42, the display control section 98 may generate a display image 523 in which the direct-viewing observation image 111 and the side-viewing observation image 112 are not connected to each other and a portion (hereinafter, referred to as a third blind spot portion) 513 corresponding to the blind spots 503 is masked as shown in FIG. 32 and may display the display image 523 on the monitor 18. It is preferable that the display image 523 in which the third blind spot portion 513 is masked and a display image, such as the display image 113 in which the third blind spot portion 513 is not masked, are switched with each other at an arbitrary timing. The display of the fifth embodiment can be arbitrarily combined with the first embodiment and the like.

Sixth Embodiment

Figure 33:
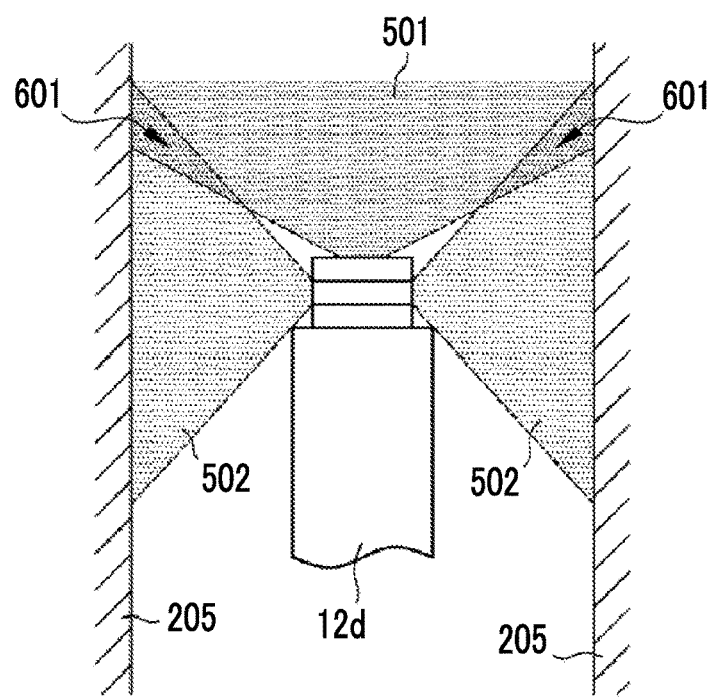
FIG. 33 is a diagram illustrating the overlap between the field of view of the direct-viewing observation unit and the field of view of the side-viewing observation unit.
Figure 34:
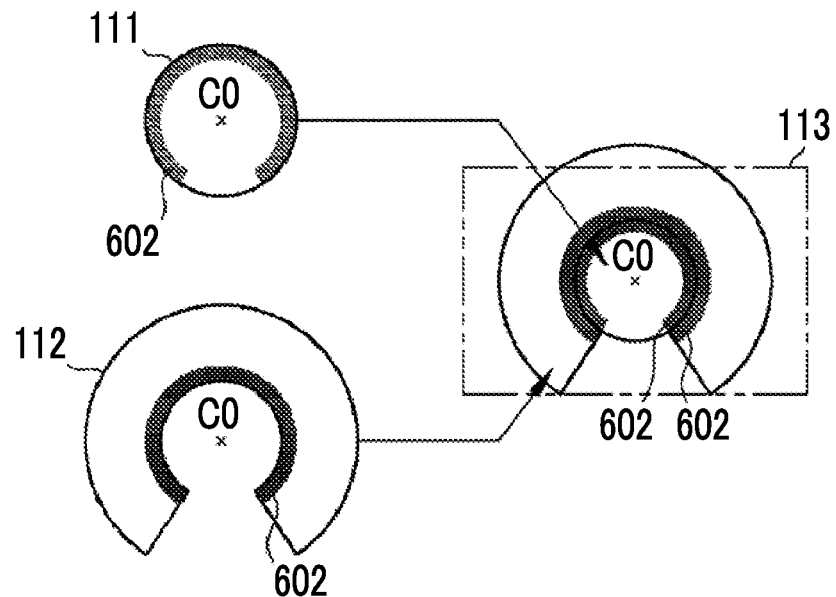
FIG. 34 is a diagram illustrating the overlapping display caused by the overlap between the fields of view.

On the contrary to the fifth embodiment, there is a case where the field 501 of view of the direct-viewing observation unit 41 and the fields 502 of view of the side-viewing observation unit 42 overlap each other in the endoscopes 12 of the first embodiment and the like due to the performance of the image pickup lens 61 as shown in FIG. 33. Hereinafter, portions in which the field of view of the direct-viewing observation unit 41 and the field of view of the side-viewing observation unit 42 overlap each other will be referred to as overlapping fields 601 of view. In a case in which the direct-viewing observation unit 41 and the side-viewing observation unit 42 have the overlapping fields 601 of view as described above, the same portion of the same object 205 to be observed is shown up in regions (hereinafter, referred to as overlapping regions) 602 corresponding to the overlapping fields 601 of view in the direct-viewing observation image 111 and the side-viewing observation image 112 as shown in FIG. 34. Accordingly, in a case in which the direct-viewing observation image 111 and the side-viewing observation image 112 are connected to each other as in the first embodiment and the like, the same portion of the object to be observed is displayed at two portions (hereinafter, referred to as double display) near the boundary between the direct-viewing observation image 111 and the side-viewing observation image 112 in the generated display image 113 and the like. Therefore, it is preferable that the display control section 98 generates a display image in which there is no double display even in a case in which the direct-viewing observation unit 41 and the side-viewing observation unit 42 have the overlapping fields 601 of view.

Figure 35:
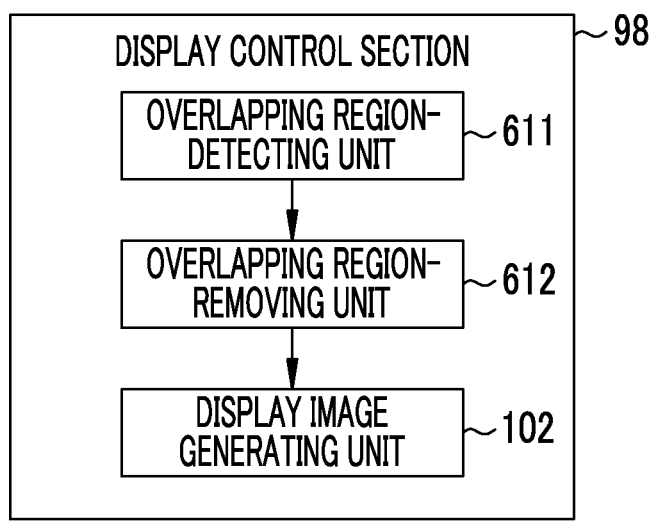
FIG. 35 is a block diagram of a display control section of a sixth embodiment.
Figure 36:
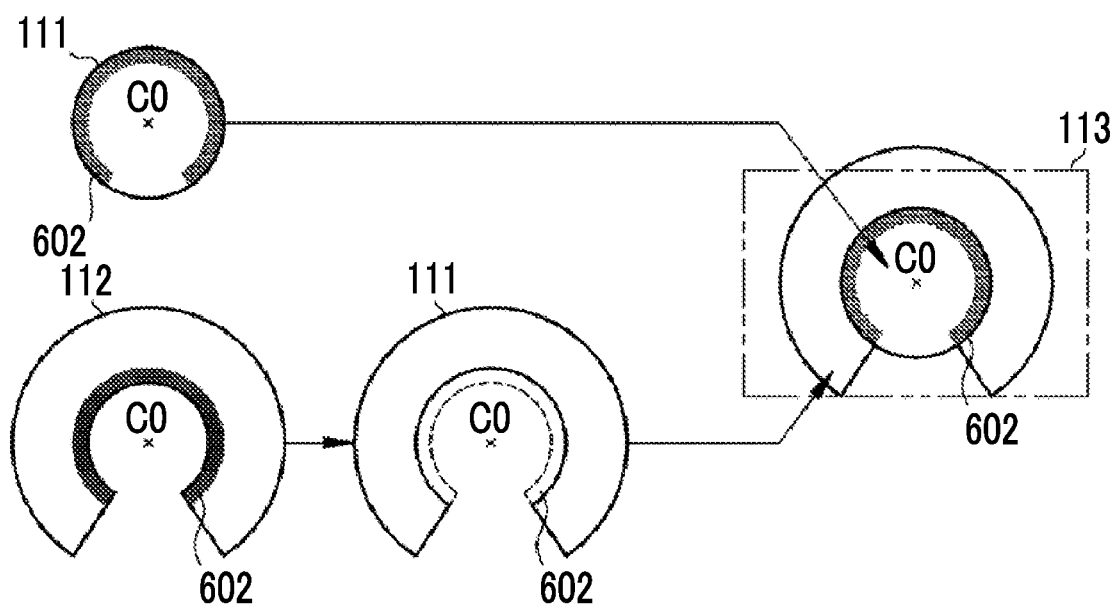
FIG. 36 is a diagram illustrating the action of an overlapping region-detecting unit and the action of an overlapping region-removing unit.
Figure 37:
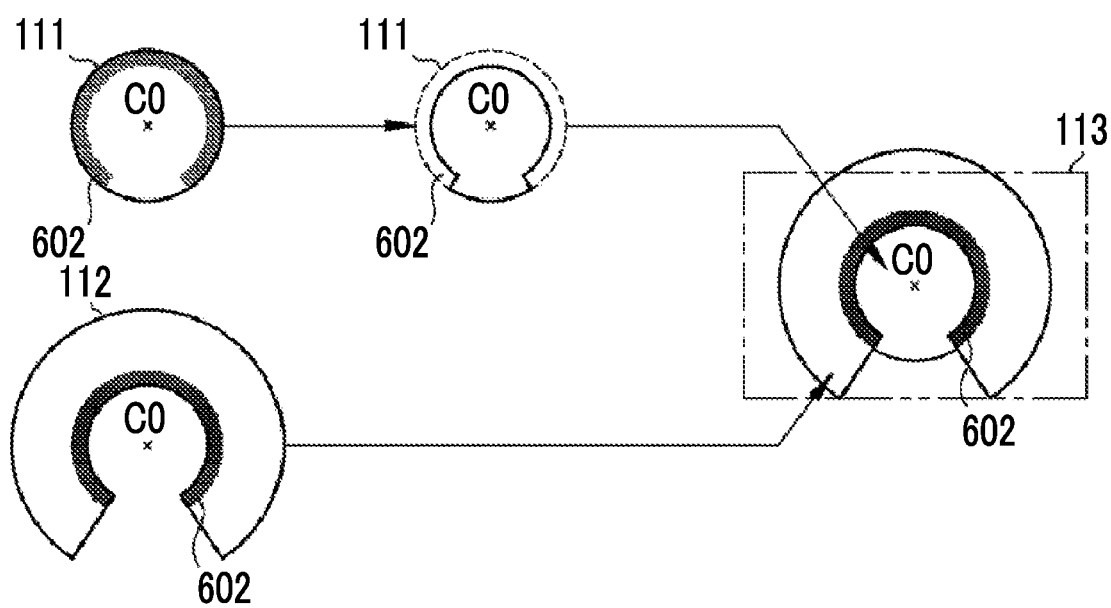
FIG. 37 is a diagram illustrating the action of an overlapping region-detecting unit and the action of an overlapping region-removing unit.

For this purpose, it is preferable that the display control section 98 is provided with, for example, an overlapping region-detecting unit 611 and an overlapping region-removing unit 612 as shown in FIG. 35. The overlapping region-detecting unit 611 detects an overlapping region 602 of the direct-viewing observation image 111 in which the same object to be observed as an object to be observed shown up in the side-viewing observation image 112 is shown up or an overlapping region 602 of the side-viewing observation image 112 in which the same object to be observed as an object to be observed shown up in the direct-viewing observation image 111 is shown up by comparing the object to be observed, which is shown up in the direct-viewing observation image 111, with the object to be observed that is shown up in the side-viewing observation image 112. Then, the overlapping region-removing unit 612 removes the overlapping region 602 from the direct-viewing observation image 111 or the side-viewing observation image 112 as shown in FIGS. 36 and 37. After that, the display image generating unit 102 generates the display image 113 and the like by connecting the direct-viewing observation image 111 to the side-viewing observation image 112 (the overlapping region 602 has been removed from any one of the direct-viewing observation image 111 and the side-viewing observation image 112). Accordingly, even though the direct-viewing observation unit 41 and the side-viewing observation unit 42 have the overlapping fields 601 of view, there is no double display of the display image 113 and the like. Therefore, an object to be observed can be displayed so as to be easily observed.

Figure 38:
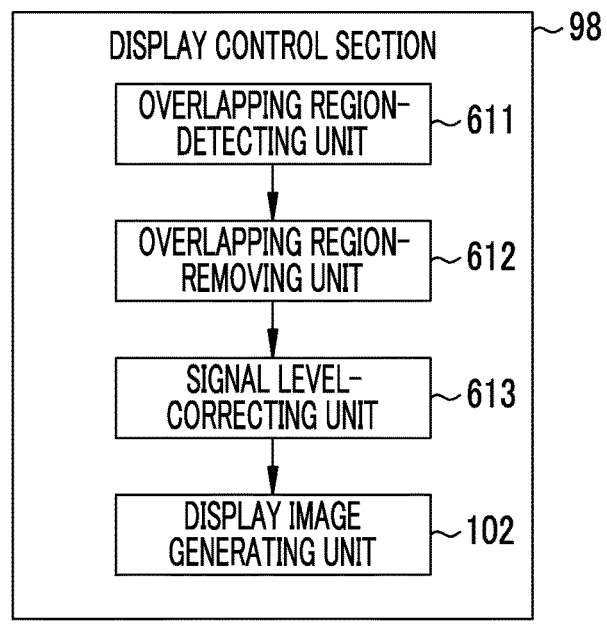
FIG. 38 is a block diagram of a display control section of a modification example of the sixth embodiment.

In a case in which the display control section 98 is provided with the overlapping region-detecting unit 611 as in the sixth embodiment, it is good that the display control section 98 is further provided with a signal level-correcting unit 613 as shown in FIG. 38. The signal level-correcting unit 613 corrects the signal level of at least one of the direct-viewing observation image 111 and the side-viewing observation image 112 by using the overlapping region 602 that is detected by the overlapping region-detecting unit 611. As a result, since the direct-viewing observation image 111 and the side-viewing observation image 112 can be set to the same brightness even though the brightness of an object to be observed in the field 501 of view of the direct-viewing observation unit 41 is different from the brightness of an object to be observed in the fields 502 of view of the side-viewing observation unit 42, the display image 113 and the like having uniform brightness can be generated and displayed.

In a case in which the direct-viewing observation unit 41 and the side-viewing observation unit 42 have the overlapping fields 601 of view, the sixth embodiment and the modification example thereof can be arbitrarily combined with the direct-viewing enlargement mode, the side-viewing enlargement mode, or the standard mode of the first embodiment and the like.

Seventh Embodiment

In the first embodiment and the like, the display control section 98 connects the direct-viewing observation image 111 to the side-viewing observation image 112 by enlargement, reduction, or the like of the direct-viewing observation image 111 or the side-viewing observation image 112 in a case in which the display image 113 and the like are generated by the display image generating unit 102. However, there is a case where the state of aberration of the direct-viewing observation image 111 and the state of aberration of the side-viewing observation image 112 caused by the performance of the image pickup lens 61 are different from each other. If the direct-viewing observation image 111 and the side-viewing observation image 112 are connected to each other by only enlargement, reduction, or the like of the direct-viewing observation image 111 or the side-viewing observation image 112 in a case in which the state of aberration of the direct-viewing observation image 111 and the state of aberration of the side-viewing observation image 112 are different from each other, there is a case where an object to be observed is seen so as to be distorted in the display image 113 and the like due to a difference between the aberration of the direct-viewing observation image 111 and the aberration of the side-viewing observation image 112.

Figure 39:
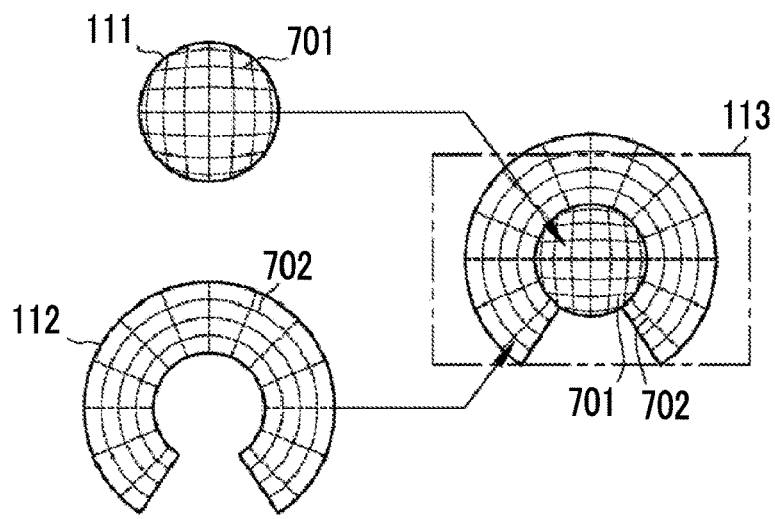
FIG. 39 is a diagram illustrating the distortion of a direct-viewing observation image and a side-viewing observation image.

For example, the distortion 701 of the direct-viewing observation image 111 and the distortion 702 of the side-viewing observation image 112 are different from each other as shown in FIG. 39. Specifically, the distortion 701 of the direct-viewing observation image 111 is so-called barrel-shaped distortion or bobbin-shaped distortion (barrel-shaped distortion in FIG. 39). On the other hand, the distortion 702 of the side-viewing observation image 112 is substantially radial distortion. For this reason, there is a case where the distortion 701 of the direct-viewing observation image 111 and the distortion 702 of the side-viewing observation image 112 cannot be successfully connected to each other by only enlargement, reduction, or the like of the direct-viewing observation image 111 or the side-viewing observation image 112. In this case, the distortion of an object to be observed is particularly easily recognized near the boundary between the direct-viewing observation image 111 and the side-viewing observation image 112 in the display image 113 and the like. Accordingly, in a case in which the display image 113 and the like are to be generated by the connection between the direct-viewing observation image 111 and the side-viewing observation image 112 and are to be displayed on the monitor 18, it is preferable that the display control section 98 generates the display image 113 and the like by connecting the direct-viewing observation image 111 to the side-viewing observation image 112 in consideration of the aberration of the direct-viewing observation image 111 and the aberration of the side-viewing observation image 112 that are caused by the performance of the image pickup lens 61.

Figure 40:
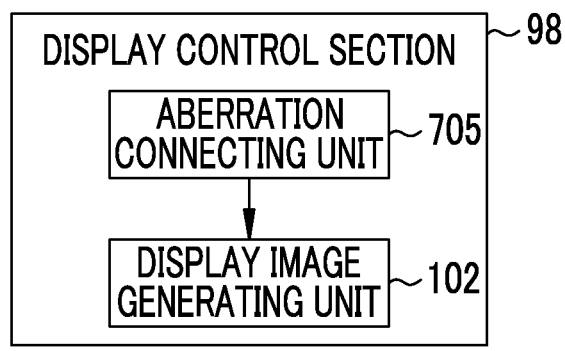
FIG. 40 is a block diagram of a display control section of a seventh embodiment.
Figure 41:
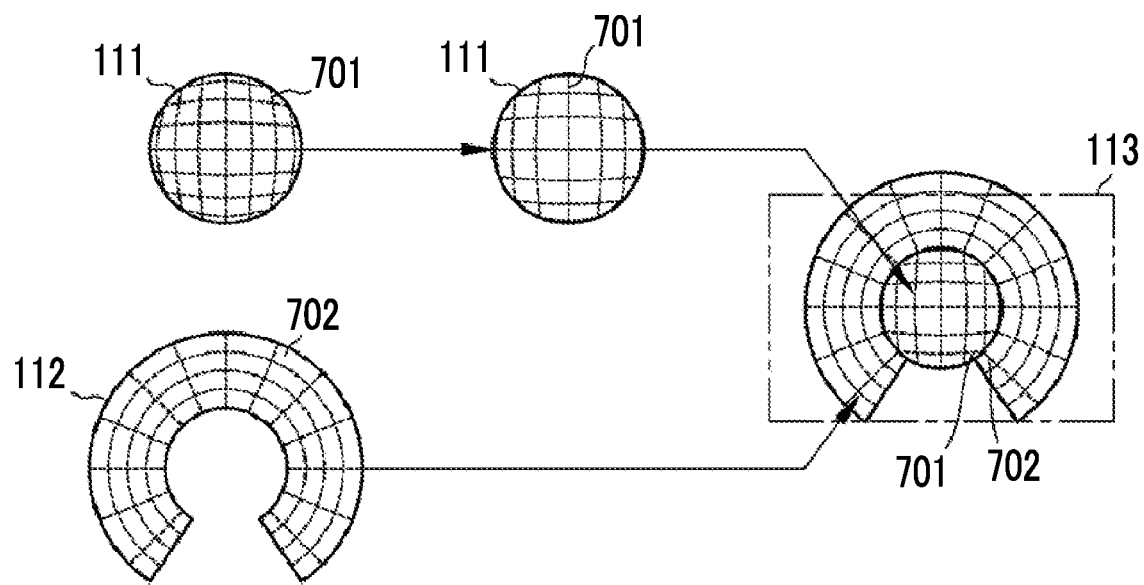
FIG. 41 is a diagram illustrating the action of an aberration connecting unit.

The display control section 98 is provided with an aberration connecting unit 705 as shown in FIG. 40 to connect the direct-viewing observation image 111 to the side-viewing observation image 112 in consideration of the aberration of the direct-viewing observation image 111 and the aberration of the side-viewing observation image 112 that are caused by the performance of the image pickup lens 61. The aberration connecting unit 705 performs transformation processing, such as affine transformation, on at least one of the direct-viewing observation image 111 and the side-viewing observation image 112 to transform the aberration of the direct-viewing observation image 111 and the aberration of the side-viewing observation image 112 into images that can be successfully connected to each other. For example, the aberration connecting unit 705 performs affine transformation on the direct-viewing observation image 111 in accordance with the distortion 702 of the side-viewing observation image 112 as shown in FIG. 41. As a result, the distortion 701 of the direct-viewing observation image 111 is successfully connected to the distortion 702 of the side-viewing observation image 112. The display image generating unit 102 generates the display image 113 and the like by using the direct-viewing observation image 111 and the side-viewing observation image 112 of which aberrations can be successfully connected to each other by the transformation processing of the aberration connecting unit 705 as described above, and generates the display image 113 and the like on the monitor 18. In a case in which the direct-viewing observation image 111 and the side-viewing observation image 112 are connected to each other in consideration of the aberration of the direct-viewing observation image 111 and the aberration of the side-viewing observation image 112 as described above, the direct-viewing observation image 111 and the side-viewing observation image 112 can be more successfully connected to each other. As a result, since the distortion of an object to be observed is not easily recognized in the display image 113 and the like, the object to be observed is easily observed.

Figure 42:
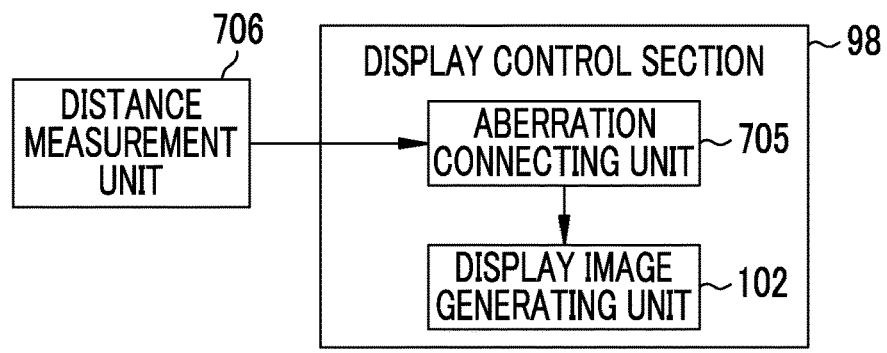
FIG. 42 is a block diagram of a modification example of the seventh embodiment.
Figure 43:
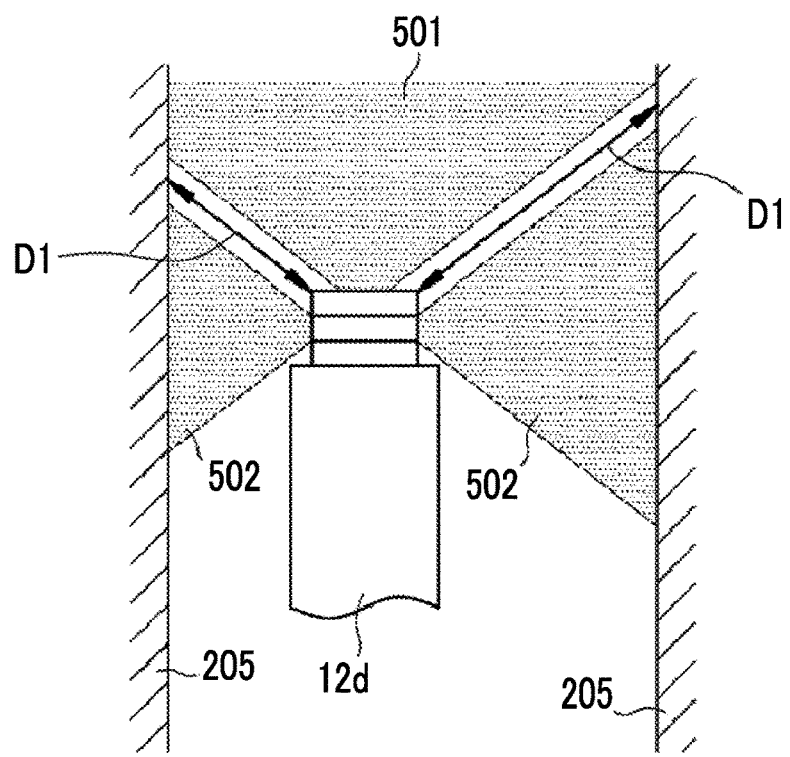
FIG. 43 is a diagram illustrating a position at which distances are measured.

Since the performance of the image pickup lens 61 is already known at the time of the manufacture of the endoscope 12, transformation processing to be performed on the direct-viewing observation image 111 or the side-viewing observation image 112 has been determined in advance in the seventh embodiment. For this reason, the aberration connecting unit 705 has stored parameters for transformation processing, which is to be performed on the direct-viewing observation image 111 or the side-viewing observation image 112, in advance. However, more precisely, in a case in which a distance between the tip part 12d of the endoscope 12 and an object to be observed is changed during observation, the state of aberration of the distortion 701 of the direct-viewing observation image 111 and the state of aberration of the distortion 702 of the side-viewing observation image 112 are changed according to the distance between the tip part 12d and the object to be observed. Accordingly, in a case in which the display control section 98 is provided with the aberration connecting unit 705, it is preferable that the endoscope 12 or the processor device 16 is provided with a distance measurement unit 706 as shown in FIG. 42. As shown in FIG. 43, the distance measurement unit 706 measures a distance D1 between the tip part 12d and the object to be observed near boundaries between the field 501 of view of the direct-viewing observation unit 41 and the fields 502 of view of the side-viewing observation unit 42. Further, the aberration connecting unit 705 adjusts or changes the parameters for transformation processing, which are stored therein in advance, by using the distance D1 between the tip part 12d and the object to be observed that is measured by the distance measurement unit 706. As a result, the aberration of the direct-viewing observation image 111 and the aberration of the side-viewing observation image 112 can be successfully connected to each other. Since the distance D1 between the tip part 12d and the object to be observed varies depending on the position (see FIG. 43), the aberration connecting unit 705 adjusts or changes the parameters for transformation processing in accordance with an average value of the distances D1 and the like or for every position at which the direct-viewing observation image 111 and the side-viewing observation image 112 are connected to each other. Furthermore, in a case in which a relative angle between the tip part 12d of the endoscope 12 and the object to be observed is changed during observation, the state of aberration of the distortion 701 of the direct-viewing observation image 111 and the state of aberration of the distortion 702 of the side-viewing observation image 112 are changed according to the relative angle between the tip part 12d and the object to be observed. For this reason, the aberration connecting unit 705 can adjust or change the parameters for transformation processing, which are stored therein in advance, by using the relative angle between the tip part 12d and the object to be observed. The relative angle between the tip part 12d and the object to be observed can be obtained by, for example, the use of the distribution of the distance D1. Since the relative angle between the tip part 12d and the object to be observed varies depending on the position, the aberration connecting unit 705 adjusts or changes the parameters for transformation processing in accordance with an average value of the relative angles between the tip part 12d and the object to be observed or for every position at which the direct-viewing observation image 111 and the side-viewing observation image 112 are connected to each other, which is the same as described above.

In a case in which blind spots 503 are present between the field 501 of view of the direct-viewing observation unit 41 and the fields 502 of view of the side-viewing observation unit 42, portions near boundaries between the field 501 of view of the direct-viewing observation unit 41 and the fields 502 of view of the side-viewing observation unit 42 are portions near boundaries between the field 501 of view of the direct-viewing observation unit 41 and the blind spots 503, portions near boundaries between the fields 502 of view of the side-viewing observation unit 42 and the blind spots 503, or arbitrary portions in the ranges of the blind spots 503. In a case in which the overlapping fields 601 of view are present in the field 501 of view of the direct-viewing observation unit 41 and the fields 502 of view of the side-viewing observation unit 42, portions near boundaries between the field 501 of view of the direct-viewing observation unit 41 and the fields 502 of view of the side-viewing observation unit 42 are portions near boundaries between the field 501 of view of the direct-viewing observation unit 41 and the overlapping fields 601 of view, portions near boundaries between the fields 502 of view of the side-viewing observation unit 42 and the overlapping fields 601 of view, or arbitrary portions in the ranges of the overlapping fields 601 of view. In a case in which blind spots 503 are not present between the field 501 of view of the direct-viewing observation unit 41 and the fields 502 of view of the side-viewing observation unit 42 and overlapping fields 601 of view are also not present, portions near boundaries between the field 501 of view of the direct-viewing observation unit 41 and the fields 502 of view of the side-viewing observation unit 42 are boundaries between the field 501 of view of the direct-viewing observation unit 41 and the fields 502 of view of the side-viewing observation unit 42 or portions near the boundaries.

Eighth Embodiment

Figure 44:
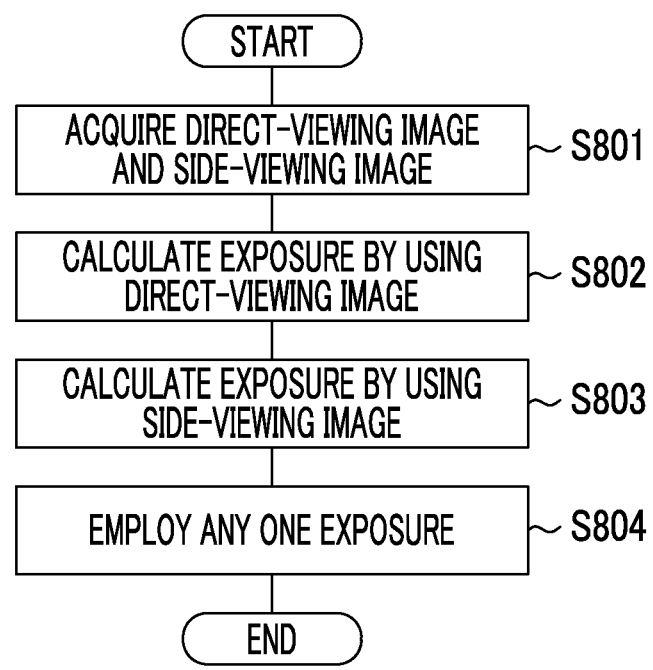
FIG. 44 is a flow chart illustrating the action of automatic exposure control.

In the first embodiment and the like, the control unit 96 performs AE control but there is a case where the brightness of the direct-viewing observation image 111 and the brightness of the side-viewing observation image 112 are different from each other depending on the distance between the tip part 12d and an object to be observed or the performance of the direct-viewing illumination units 54 and 81 and the side-viewing illumination unit 43. In a case in which the brightness of the direct-viewing observation image 111 and the brightness of the side-viewing observation image 112 are different from each other, it is difficult for the control unit 96 to perform AE control for allowing both the direct-viewing observation image 111 and the side-viewing observation image 112 to always have common constant brightness. For this reason, as shown in FIG. 44, in a case in which the control unit 96 acquires the direct-viewing observation image 111 and the side-viewing observation image 112 for the purpose of AE control (S801), the control unit 96 calculates an appropriate exposure by using the direct-viewing observation image 111 (S802). Further, the control unit 96 calculates an appropriate exposure by using the side-viewing observation image 112 (S803). Then, the control unit 96 determines any one of the exposures calculated using the direct-viewing observation image 111 and the exposure calculated using the side-viewing observation image 112 as an exposure to be used for AE control (S804), and performs actual AE control in accordance with the determined exposure. As a result, even though the brightness of the direct-viewing observation image 111 and the brightness of the side-viewing observation image 112 are different from each other, at least one of the direct-viewing observation image 111 and the side-viewing observation image 112 can always be picked up with appropriate brightness. For example, in a case in which the control unit 96 always performs AE control in accordance with the exposure calculated using the direct-viewing observation image 111, at least the direct-viewing observation image 111 always has appropriate brightness. As a result, the ease of observation of the direct-viewing observation image 111 can be ensured.

In the eighth embodiment, the control unit 96 determines any one of the exposures calculated using the direct-viewing observation image 111 and the exposure calculated using the side-viewing observation image 112 as an exposure for AE control to be actually performed. However, instead, the control unit 96 can determine an average value of the exposure calculated using the direct-viewing observation image 111 and the exposure calculated using the side-viewing observation image 112 as an exposure for AE control to be actually performed. Further, an exposure for AE control, which is to be actually performed, may be calculated, by setting, using the exposure calculated using the direct-viewing observation image 111 and the exposure calculated using the side-viewing observation image 112. For example, the exposure calculated using the direct-viewing observation image 111 and the exposure calculated using the side-viewing observation image 112 are weighted and averaged, and the result of the weighting and averaging can be employed as an exposure for AE control to be actually performed.

In a case in which a direct-viewing observation image 111 and a side-viewing observation image 112 are to be obtained at respective different timings, an exposure to be used to obtain the direct-viewing observation image 111 can be calculated using the direct-viewing observation image 111 and an exposure to be used to obtain the side-viewing observation image 112 can be calculated using the side-viewing observation image 112.

Figure 45:
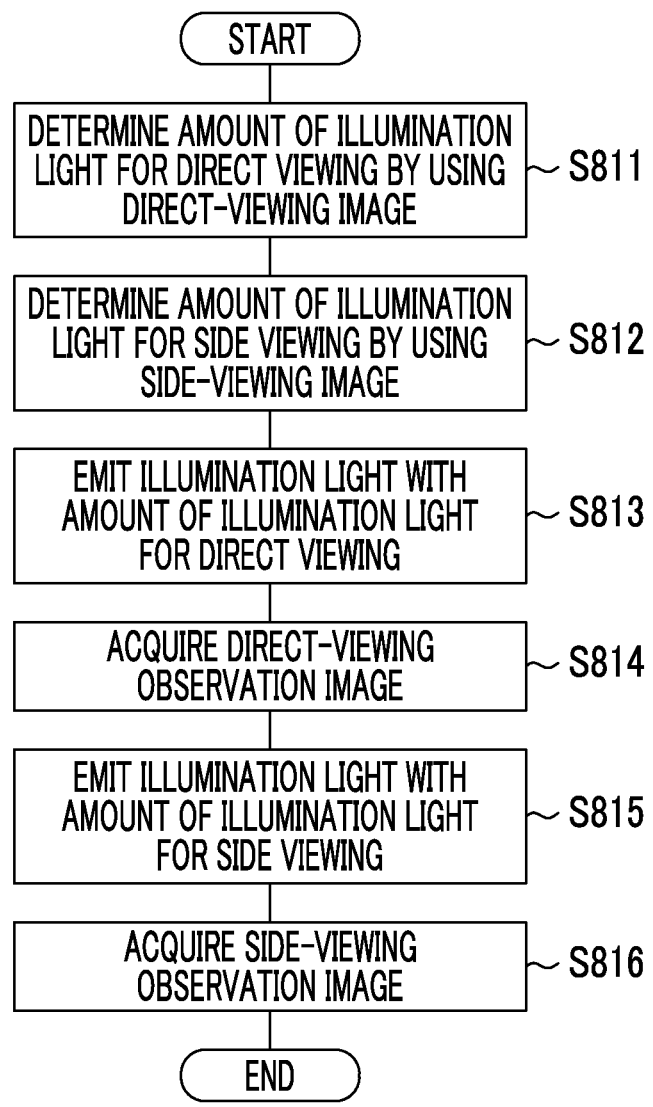
FIG. 45 is a flow chart illustrating the action of automatic exposure control of a modification example.

For example, in a case in which the control unit 96 performs AE control by adjusting the amount of illumination light, as shown in FIG. 45, the control unit 96 determines the amount of illumination light that is used when a direct-viewing observation image 111 is acquired and the next direct-viewing observation image 111 is picked up (hereinafter, referred to as the amount of illumination light for direct viewing) (S811). Further, the control unit 96 determines the amount of illumination light that is used when a side-viewing observation image 112 is acquired and the next side-viewing observation image 112 is picked up (hereinafter, referred to as the amount of illumination light for side viewing) (S812). Then, the control unit 96 emits illumination light with the amount of illumination light for direct viewing and picks up an image of an object to be observed by the direct-viewing observation unit 41. Accordingly, the image acquisition unit 97 acquires the direct-viewing observation image 111 (S813). Furthermore, the control unit 96 emits illumination light with the amount of illumination light for side viewing and picks up an image of an object to be observed by the side-viewing observation unit 42. Accordingly, the image acquisition unit 97 acquires the side-viewing observation image 112 (S814).

Since an exposure to be used to obtain a direct-viewing observation image 111 is calculated using the direct-viewing observation image 111 and an exposure to be used to obtain a side-viewing observation image 112 is calculated using the side-viewing observation image 112 in a case in which the direct-viewing observation image 111 and the side-viewing observation image 112 are to be obtained at respective different timings as described above, both the direct-viewing observation image 111 and the side-viewing observation image 112 can be acquired with appropriate exposure.

The AE control of the eighth embodiment and the modification example thereof can be arbitrarily combined with the first embodiment and the like.

Ninth Embodiment

In a case and the like in which a direct-viewing observation image 111 and a side-viewing observation image 112 are to be obtained at respective different timings, a direct-viewing observation image 111 and a side-viewing observation image 112 having properties different from each other can be obtained. For example, one of the direct-viewing observation image 111 and the side-viewing observation image 112 can be converted into a normal image, which is obtained when an image of an object to be observed is picked up with the use of white light as illumination light and expresses the object to be observed with natural color tones, and the other of the direct-viewing observation image 111 and the side-viewing observation image 112 can be converted into an image (hereinafter, referred to as a special image) that has been subjected to processing and the like so as to have an aspect different from the normal image. Examples of the special image include: an image in which a specific tissue or structure, such as a blood vessel, is enhanced by frequency enhancement processing, contour enhancement processing, marking processing (processing for displaying the position of a lesion or the like by applying a frame or the like to the lesion or the like), or the like; an image in which a specific tissue or structure, such as a blood vessel, is more easily shown up than in a normal image with the use of illumination light having a very narrow wavelength band or the selection of the wavelength or the wavelength band of illumination light or the combinations of illumination light (for example, a so-called narrow-band light observation image); an image in which a specific lesion and the like can be distinguished from peripheral tissues and the like through color differences by color tone conversion processing or the like (for example, color tone conversion using a tone curve, color tone conversion using remapping in a specific color space, or the like); an image that is obtained by calculating biological information about an object to be observed and coloring a normal image with the use of the calculated biological information (for example, an oxygen saturation image expressing a value of oxygen saturation by a color); and the like.

Figure 46:
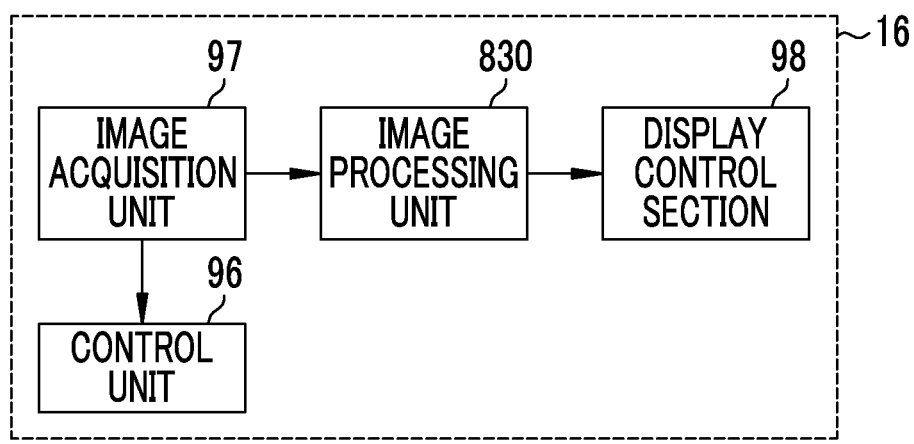
FIG. 46 is a block diagram of a processor device 16 of a ninth embodiment.

In a case in which one of the direct-viewing observation image 111 and the side-viewing observation image 112 is converted into a normal image and the other of the direct-viewing observation image 111 and the side-viewing observation image 112 is converted into a special image as described above, the processor device 16 is provided with an image processing unit 830 as shown in FIG. 46. The image processing unit 830 performs various kinds of processing, such as frequency enhancement processing, contour enhancement processing, marking processing, color tone conversion processing, oxygen saturation calculating processing, and processing for coloring a normal image by using calculated oxygen saturation on the direct-viewing observation image 111 or the side-viewing observation image 112, which is acquired from the image acquisition unit 97, as necessary. Further, the display control section 98 generates the display image 113 and the like by using the direct-viewing observation image 111 and the side-viewing observation image 112 that have been subjected to necessary processing by the image processing unit 830, and displays the display image 113 and the like on the monitor 18.

In a case in which at least one of the direct-viewing observation image 111 and the side-viewing observation image 112 is converted into a special image, the discovery of a lesion and the like can be supported in comparison with a case in which each of both the direct-viewing observation image 111 and the side-viewing observation image 112 is converted into a normal image. Further, there is also an advantage of providing information, such as biological information, in a case in which an image representing biological information is to be generated.

In a case in which only one of the direct-viewing observation image 111 and the side-viewing observation image 112 is converted into a special image, it is preferable that the direct-viewing observation image 111 is converted into a normal image and the side-viewing observation image 112 is converted into a special image. The side-viewing observation image 112 is often used for screening for discovering a lesion and the like, and is likely to be an image allowing a lesion and the like to not be better identified than the direct-viewing observation image 111. Accordingly, in a case in which the side-viewing observation image 112 is converted into a special image, screening can be supported and the accuracy of the screening can be improved.

In the ninth embodiment, the direct-viewing observation image 111 and the side-viewing observation image 112 are acquired (picked up) at respective different timings. However, the direct-viewing observation image 111 and the side-viewing observation image 112 can be simultaneously acquired and at least one of the direct-viewing observation image 111 and the side-viewing observation image 112 can be converted into a special image. For example, an image of an object to be observed is picked up with the use of white light as illumination light, and the direct-viewing observation image 111 and the side-viewing observation image 112 are simultaneously acquired. Then, normal image processing (image processing for transforming an image into a normal image) is performed on the direct-viewing observation image 111 to convert the direct-viewing observation image 111 into a normal image. On the other hand, color conversion processing for enhancing a lesion is performed on the side-viewing observation image 112, which is obtained simultaneously with the direct-viewing observation image 111, to convert the side-viewing observation image 112 into a special image. In a case in which a special image is to be generated by image processing without requiring switching illumination light as described above, at least one of the direct-viewing observation image 111 and the side-viewing observation image 112 can be converted into a special image even though the direct-viewing observation image 111 and the side-viewing observation image 112 are simultaneously acquired.

Further, in a case in which the direct-viewing illumination units 54 and 81 and the side-viewing illumination unit 43 are adapted to be independent of each other, different kinds of illumination light can be simultaneously applied to the field 501 of view of the direct-viewing observation unit 41 and the fields 502 of view of the side-viewing observation unit 42. In this case, even though the switching of illumination light is required for the generation of a special image, the direct-viewing observation image 111 and the side-viewing observation image 112 are simultaneously acquired and at least one of the direct-viewing observation image 111 and the side-viewing observation image 112 can be converted into a special image.

In the ninth embodiment, at least one of the direct-viewing observation image 111 and the side-viewing observation image 112 is converted into a special image. However, instead, the brightness of one of the direct-viewing observation image 111 and the side-viewing observation image 112 may be made higher or lower than the brightness of the other thereof. For example, the side-viewing observation image 112 can be made brighter than the direct-viewing observation image 111. A method of allowing the side-viewing observation image 112 to be brighter than the direct-viewing observation image 111 and a method of allowing the direct-viewing observation image 111 to be darker than the side-viewing observation image 112 are employed as a method of allowing the side-viewing observation image 112 to be brighter than the direct-viewing observation image 111. The control unit 96 adjusts a relative balance between the amount of illumination light for direct viewing and the amount of illumination light for side viewing in the modification example (see FIG. 45) of the eighth embodiment, so that these methods can be realized. The ninth embodiment can be arbitrarily combined with the first embodiment and the like.

Tenth Embodiment

In the first embodiment and the like, the display regions and the display positions of the direct-viewing observation image 111 and the side-viewing observation image 112 of the display image 113 and the like are determined in advance. Particularly, in the fourth embodiment and the modification example thereof, the display position of the direct-viewing observation image 111 or the side-viewing observation image 112 has been adjusted in accordance with the orientation of the tip part 12d, or the like but the display regions of the direct-viewing observation image 111 and the side-viewing observation image 112 of the display image 113 and the like are determined in advance. However, the display regions of the direct-viewing observation image 111 and the side-viewing observation image 112 can be arbitrarily determined.

The display regions of the direct-viewing observation image 111 and the side-viewing observation image 112 are the ranges of the direct-viewing observation image 111 and the side-viewing observation image 112 that are displayed on the monitor 18 by the display image 113 and the like. For example, since the centers C0 of the direct-viewing observation image 111 and the side-viewing observation image 112 are disposed at the center of the display image 113 in the display image 113, a part of the side-viewing observation image 112 originally having an annular shape protrudes to the outside of the display image 113 and is not displayed in the display image 113. In contrast, the range of the side-viewing observation image 112, which is used in the display image 113, is the display region of the side-viewing observation image 112.

Figure 47:
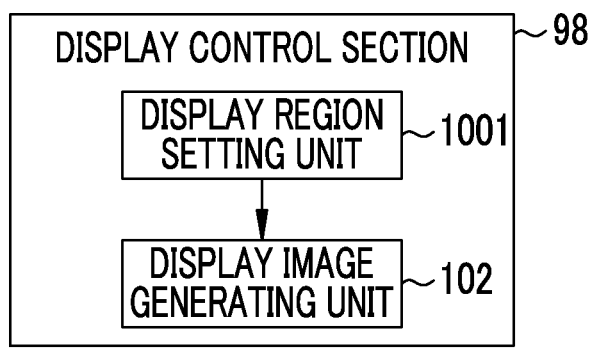
FIG. 47 is a block diagram of a display control section 98 of a tenth embodiment.
Figure 48:
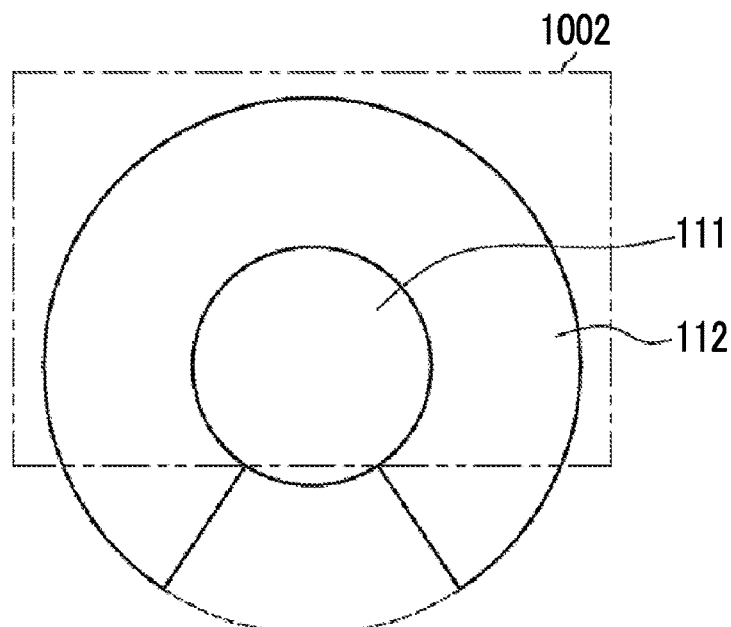
FIG. 48 is a diagram illustrating an interrelationship between a display region of a monitor and a direct-viewing observation image and a side-viewing observation image.

In a case in which the display ranges of the direct-viewing observation image 111 and the side-viewing observation image 112 are to be adjusted in the display image 113 and the like, the display control section 98 is provided with a display region setting unit 1001 as shown in FIG. 47. As shown in FIG. 48, the display region setting unit 1001 adjusts the position of the display region 1002 on the monitor 18 relative to the positions of the direct-viewing observation image 111 and the side-viewing observation image 112, and the size of the display region 1002 on the monitor 18. As a result, since the display region setting unit 1001 allows the direct-viewing observation image 111 and the side-viewing observation image 112 to be within the display image 113 and the like, the display region setting unit 1001 sets a region displayed on the monitor 18 (that is, the display region). The size and shape of the display region 1002 are the size and shape of the display image 113 and the like, and are determined in advance by setting or the like in this embodiment.

Figure 49:
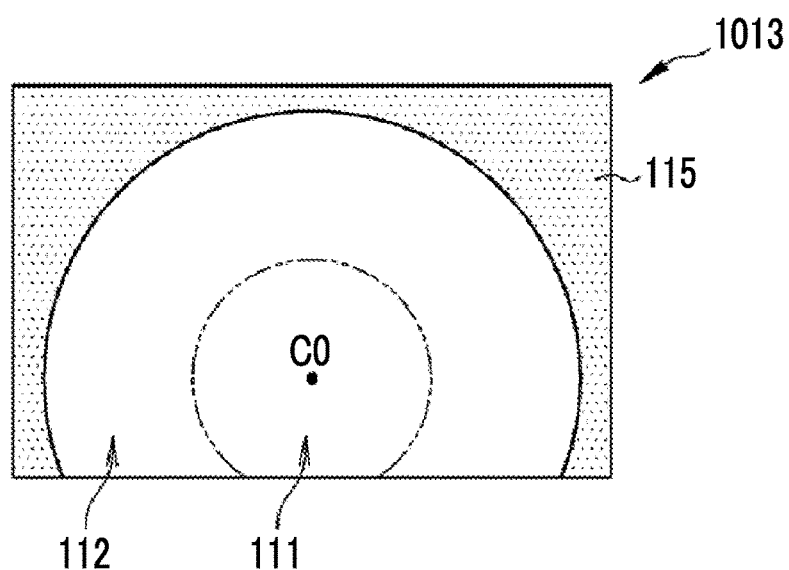
FIG. 49 shows a display image in which the direct-viewing observation image and the side-viewing observation image are offset so that a first blind spot portion is not displayed.

For example, in a case in which the display region setting unit 1001 sets an interrelationship between the direct-viewing observation image 111 and the side-viewing observation image 112 and the display region 1002 as shown in FIG. 48, the display image generating unit 102 generates a display image 1013 shown in FIG. 49 in accordance with the interrelationship between the direct-viewing observation image 111 and the side-viewing observation image 112 and the display region 1002 set by the display region setting unit 1001 and displays the display image 1013 on the monitor 18.

In the tenth embodiment, the display control section 98 allows the entire first blind spot portion 114, which corresponds to a blind spot in which the second protruding portion 32 is shown up, not to be displayed by offsetting the display positions of the direct-viewing observation image 111 and the side-viewing observation image 112 with respect to the display region 1002 on the monitor 18 serving as the display unit. For this reason, since the first blind spot portion 114 can be excluded from the display on the monitor 18, a display focusing on the observation of an object to be observed can be made without concern about the presence of the first blind spot portion 114 in the display on the monitor 18.

Figure 50:
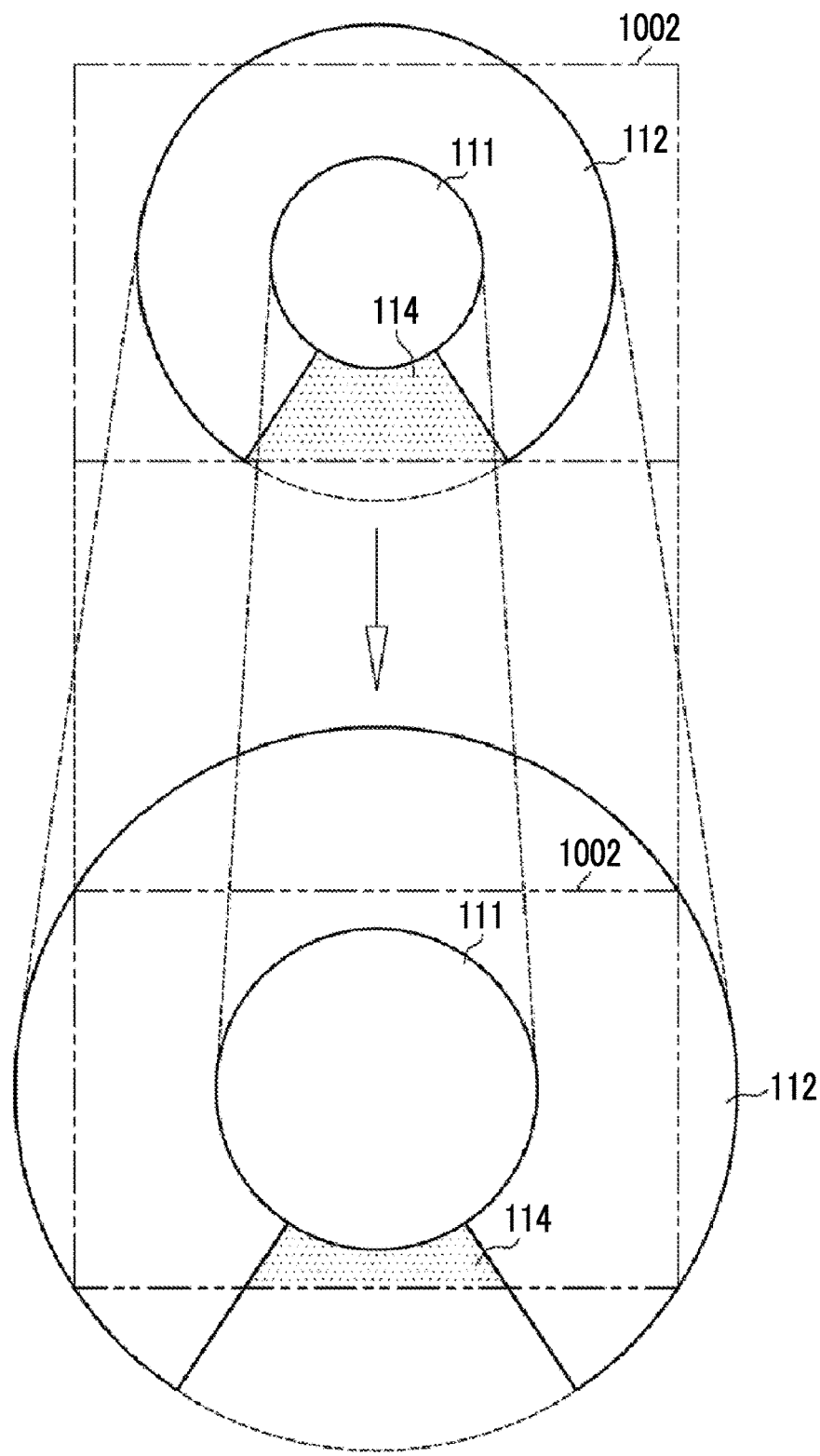
FIG. 50 is a diagram illustrating a method of allowing at least a part of the first blind spot portion not to be displayed.

The entire first blind spot portion 114 is not displayed in the tenth embodiment. However, in a case in which the display control section 98 is provided with the display region setting unit 1001, it is preferable that the display control section 98 allows at least a part of a blind spot not to be displayed by offsetting the display positions of the direct-viewing observation image 111 and the side-viewing observation image 112 with respect to the display region 1002 on the monitor 18 serving as the display unit. The display control section 98 can allow at least a part of the first blind spot portion 114, which corresponds to a blind spot in which the second protruding portion 32 is shown up, not to be displayed by enlarging the direct-viewing observation image 111 and the side-viewing observation image 112 with respect to the display region 1002 on the monitor 18 serving as the display unit after offsetting the display positions of the direct-viewing observation image 111 and the side-viewing observation image 112 with respect to the display region 1002, instead of offsetting the display positions of the direct-viewing observation image 111 and the side-viewing observation image 112 with respect to the display region 1002 as described above. The reason for this is that a user focuses more on the observation of an object to be observed than in a case in which the entire first blind spot portion 114 of the display image 113 and the like is made to be within the display region 1002 in a case in which at least a part of the first blind spot portion 114 is not displayed. For example, in a case in which the display control section 98 enlarges the direct-viewing observation image 111 and the side-viewing observation image 112 with respect to the display region 1002 as shown in FIG. 50, the display control section 98 can allow a part of the first blind spot portion 114 not to be displayed.

Figure 51:
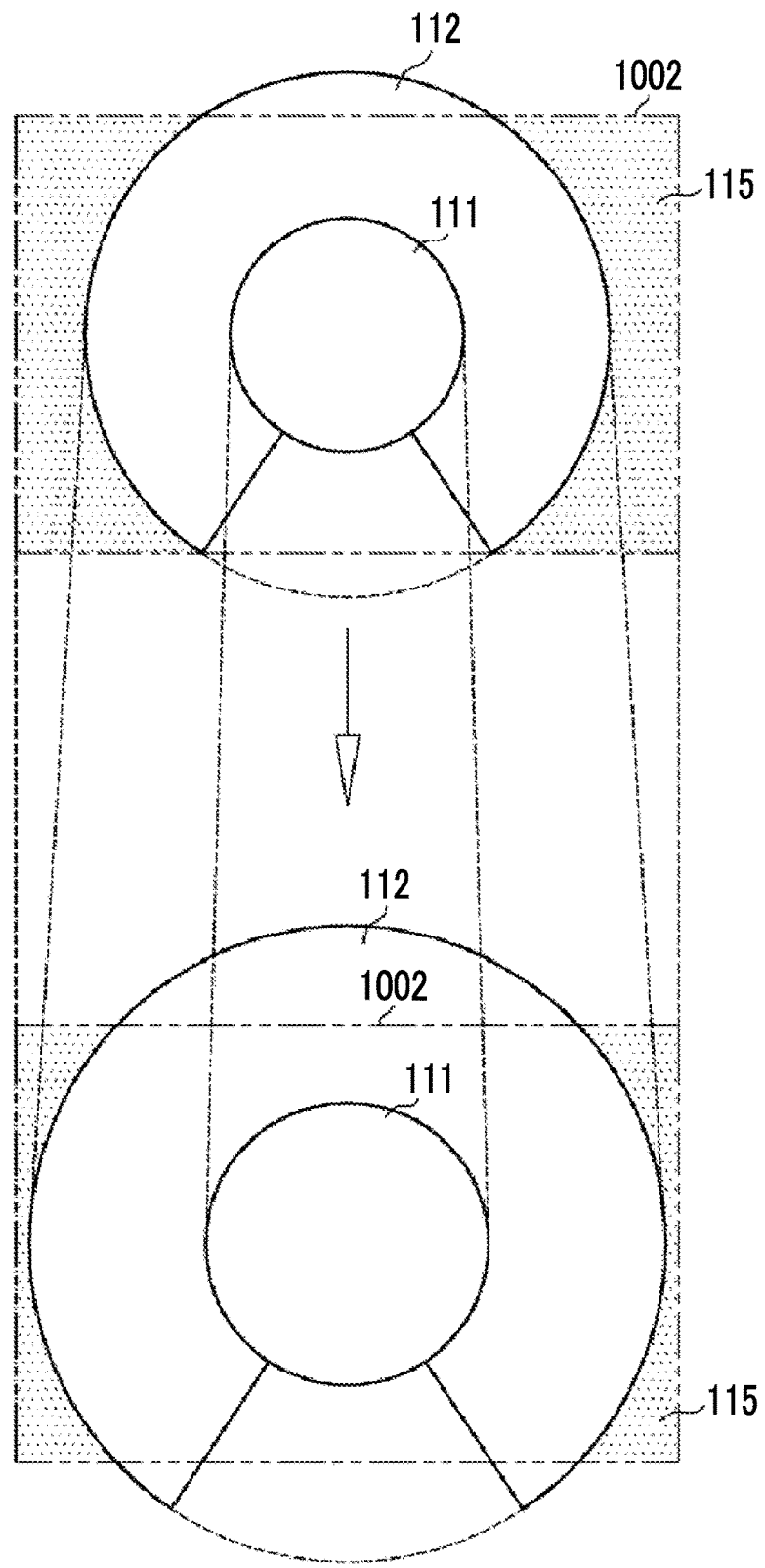
FIG. 51 is a diagram illustrating a method of allowing at least a part of the second blind spot portion not to be displayed.

Further, in a case in which the display control section 98 enlarges the direct-viewing observation image 111 and the side-viewing observation image 112 with respect to the display region 1002 as shown in FIG. 51, the display control section 98 can allow at least a part of the second blind spot portion 115 not to be displayed. For this reason, a user can focus more on the observation of an object to be observed than the display image 113 and the like.

It is preferable that the non-display of the first blind spot portion 114 and the second blind spot portion 115, which is achieved by the offsetting or enlargement, can be selected as a display mode. That is, it is preferable that the display control section 98 includes a blind spot-non-display mode in addition to the standard mode, the direct-viewing enlargement mode, or the side-viewing enlargement mode of the first embodiment and the like or instead of the standard mode, the direct-viewing enlargement mode, or the side-viewing enlargement mode of the first embodiment and the like. In a case in which a display mode is set to the blind spot-non-display mode, the display control section 98 allows at least a part of the first blind spot portion 114 and the second blind spot portion 115, which corresponds to a blind spot in which the second protruding portion 32 is shown up, not to be displayed and displays the direct-viewing observation image 111 and the side-viewing observation image on the monitor 18 serving as the display unit.

Figure 52:
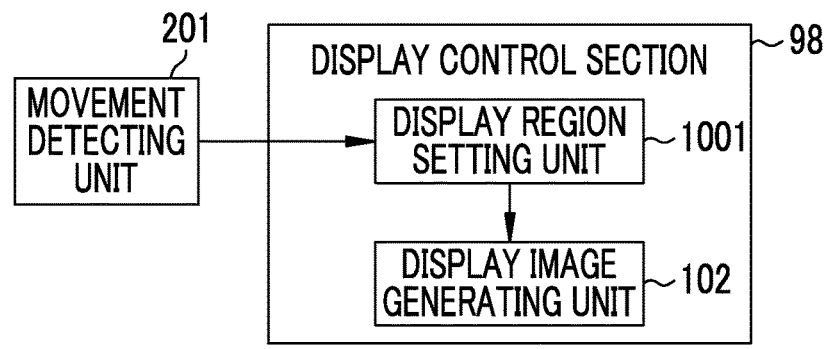
FIG. 52 is a block diagram of a display control section in a case in which the first blind spot portion or the second blind spot portion is not displayed in accordance with the movement of the insertion part (the tip part).

The display control section 98 can change the ratio of a portion, which is not to be displayed, of the first blind spot portion 114 that corresponds to a blind spot in which the second protruding portion 32 is shown up. For example, in a case in which the processor device 16 is provided with the movement detecting unit 201 as shown in FIG. 52, it is good that the display region setting unit 1001 changes the ratio of a portion, which is not to be displayed, of the first blind spot portion 114 or the second blind spot portion 115 in accordance with the movement of the tip part 12d (that is, the movement of the insertion part 12a).

Figure 53:
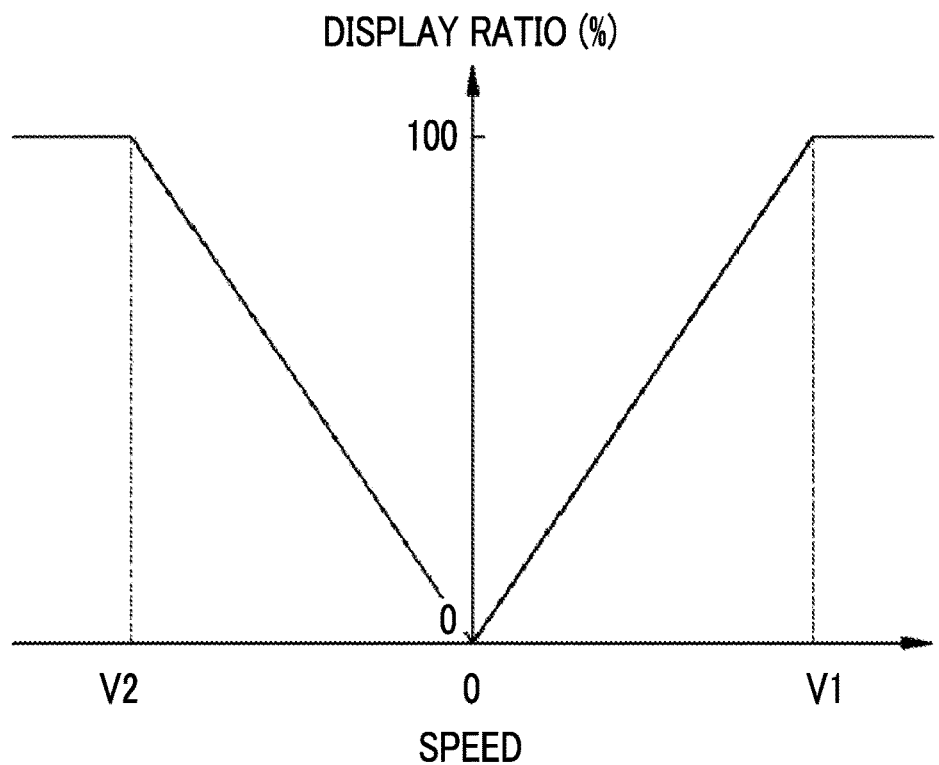
FIG. 53 is a graph showing a relationship between the speed of insertion/extraction of the insertion part and the ratio of a portion, which is not to be displayed, of the first blind spot portion or the second blind spot portion.

More specifically, in a case in which the movement detecting unit 201 is to detect the insertion/extraction of the insertion part 12a, the display region setting unit 1001 can set the ratio of a portion, which is not to be displayed, of the first blind spot portion 114 or the second blind spot portion 115 in accordance with the speed (or acceleration) of insertion/extraction of the insertion part 12a as shown in FIG. 53. That is, as the insertion/extraction of the insertion part 12a becomes quick, the ratio of a portion, which is not to be displayed, of the first blind spot portion 114 or the second blind spot portion 115 is set to be increased. In this case, as the insertion/extraction of the insertion part 12a becomes quick and the obstruction of observation of the first blind spot portion 114 or the second blind spot portion 115 becomes easy, the display area of the first blind spot portion 114 or the second blind spot portion 115 is reduced. Accordingly, the insertion/extraction of the insertion part 12a can be supported.

Figure 54:
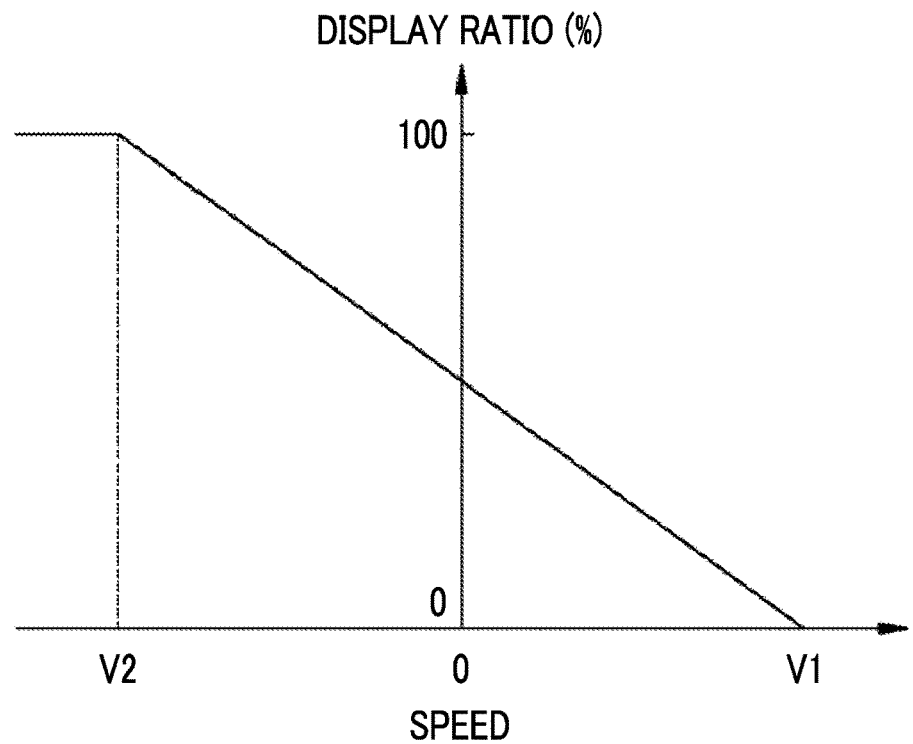
FIG. 54 is a graph showing a relationship between the speed of insertion/extraction of the insertion part and the ratio of a portion, which is not to be displayed, of the first blind spot portion or the second blind spot portion.

In FIG. 53, the ratio of a portion, which is not to be displayed, of the first blind spot portion 114 or the second blind spot portion 115 is changed due to the velocity of insertion/extraction of the insertion part 12a regardless of the direction of insertion/extraction of the insertion part 12a. However, as shown in, for example, FIG. 54, the display control section 98 can change the ratio of a portion, which is not to be displayed, of the first blind spot portion 114 or the second blind spot portion in a case in which the insertion part 12a is to be inserted into an object to be observed and a case in which the insertion part 12a is to be extracted from the object to be observed. In addition, the display control section 98 can change the ratio of a portion, which is not to be displayed, of the first blind spot portion 114 or the second blind spot portion in accordance with the orientation of the tip part 12d or the velocity, speed, or acceleration of change of the orientation of the tip part 12d.

The tenth embodiment can be arbitrarily combined with the first embodiment and the like. For example, the display control section 98 can adjust the display ratios of the side-viewing observation image 112 and the direct-viewing observation image 111 in the same manner as the first embodiment and the like, and can change the ratio of a portion, which is not to be displayed, of the first blind spot portion 114 or the second blind spot portion 115 in accordance with the display ratios of the side-viewing observation image 112 and the direct-viewing observation image 111. This is the same as a case in which the first blind spot portion 114 is reduced in accordance with the display ratios of the side-viewing observation image 112 and the direct-viewing observation image 111 in the third embodiment.

In a case in which the display control section 98 allows the first blind spot portion 114 or the second blind spot portion 115 not to be displayed as in the tenth embodiment (particularly, in a case in which the display control section 98 includes the blind spot-non-display mode), it is preferable that the nozzles 51 and 52, which eject washing liquid to the side-viewing observation unit 42 to wash the side-viewing observation unit 42, are provided in a non-display region (a region outside the display region 1002) that is not to be displayed in a case in which the display control section 98 displays the side-viewing observation image 112 on the monitor 18 serving as the display unit. In this case, since the nozzles 51 and 52 do not need to be necessarily provided at the second protruding portion 32, there is a case where the washability of the side-viewing observation unit 42 is improved depending on the arrangement of the nozzles 51 and 52.

Figure 55:
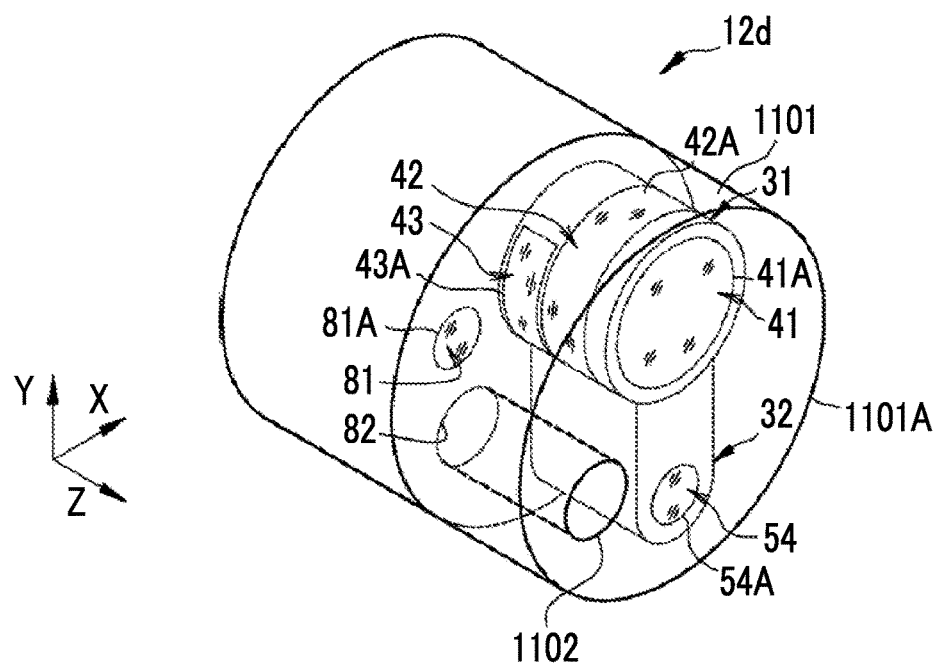
FIG. 55 is a perspective view of the tip part on which a tip cap is mounted.

The endoscopes 12 of the first embodiment and the like are inserted into an object to be observed in a state in which a complicated shape in which the first and second protruding portions 31 and 32 protrude from the tip surface 21 of the tip part 12d is exposed to the outside. However, the endoscope 12, which can perform direct-viewing observation and side-viewing observation, can be used in a state in which the tip part 12d (particularly, a portion corresponding to the first and second protruding portions 31 and 32) is covered with a tip cap 1101 as shown in, for example, FIG. 55. The shape of a portion, which is to be exposed in a case in which the tip cap 1101 is used, is simpler than the shape of a portion, which is to be exposed, of the tip part 12d that includes the first and second protruding portions 31 and 32. Accordingly, in a case in which the tip cap 1101 is used, dirt rarely remains on the portion that is to be exposed and dirt is easily removed even though dirt adheres to the portion to be exposed. Further, since a through hole 1102 is formed in the tip cap 1101 at the position of the forceps port 82, a treatment tool or the like can protrude to the outside of the tip cap 1101 from the through hole 1102.

Figure 56:
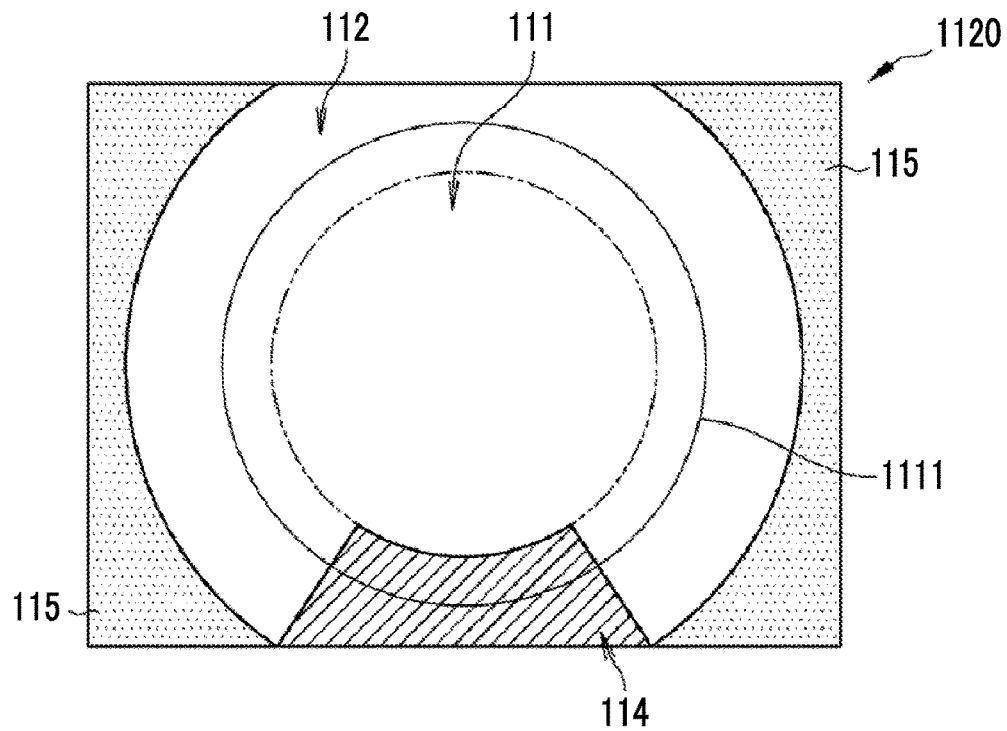
FIG. 56 shows a display image in which the outline of the tip cap is displayed.

Since the tip cap 1101 is transparent, the tip cap 1101 basically does not hinder the direct-viewing observation using the direct-viewing illumination unit 54, the direct-viewing illumination unit 81, and the direct-viewing observation unit 41 and the side-viewing observation using the side-viewing illumination unit 43 and the side-viewing observation unit 42. However, although the tip cap 1101 is transparent, there is a case where the image of an object to be observed is distorted, for example, at an outline 1101A of the tip cap 1101 or near the outline 1101A. For this reason, it is preferable that the display control section 98 generates a display image 1120 in which a line 1111 (for example, a colored line or band) or the like representing the presence of the outline 1101A of the tip cap 1101 is displayed as shown in FIG. 56 at a portion where distortion is likely to be displayed in the image of the object to be observed at the outline 1101A of the tip cap 1101 or near the outline 1101A, and displays the display image 1120 on the monitor 18. Since a doctor or the like can recognize that distortion is present in the image near the line 1111 or the like in a case in which the presence of the outline 1101A of the tip cap 1101 is displayed in the display image 1120, false recognition or the like can be prevented.

Figure 57:
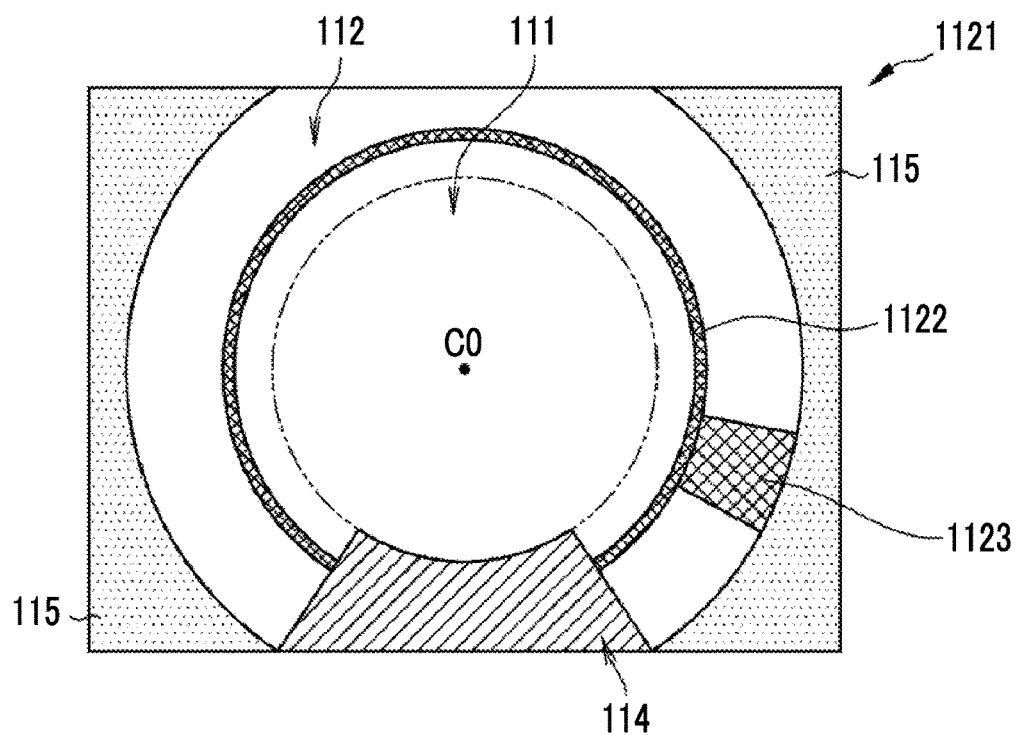
FIG. 57 shows a display image in which the outline of the tip cap and a portion of a through hole are masked.

The display control section 98 may generate a display image 1121 in which the outline 1101A of the tip cap 1101 or a portion 1122 of the tip cap 1101 near the outline 1101A, at which distortion is likely to be displayed in the image of the object to be observed, are masked as shown in FIG. 57 instead of the display of the line 1111 or the like representing the presence of the outline 1101A of the tip cap 1101 as described above; and may display the display image 1121 on the monitor 18. The image of the object to be observed is also likely to be distorted at a portion 1123 corresponding to the through hole 1102 as in the case of the outline 1101A of the tip cap 1101 or the portion 1122 near the outline 1101A. For this reason, the display control section 98 may also mask the portion 1123 corresponding to the through hole 1102 (see FIG. 57). Further, a line or the like informing a user of the presence of the through hole 1102 may be displayed as in FIG. 56 at the portion 1123 corresponding to the through hole 1102. The tip cap 1101 has a columnar shape, but an artillery shell-shaped (tapered) tip cap which gradually tapers toward the tip side thereof can also be used. The artillery shell-shaped tip cap also has the same structure as the tip cap 1101 except for an outer shape.

Figure 58:
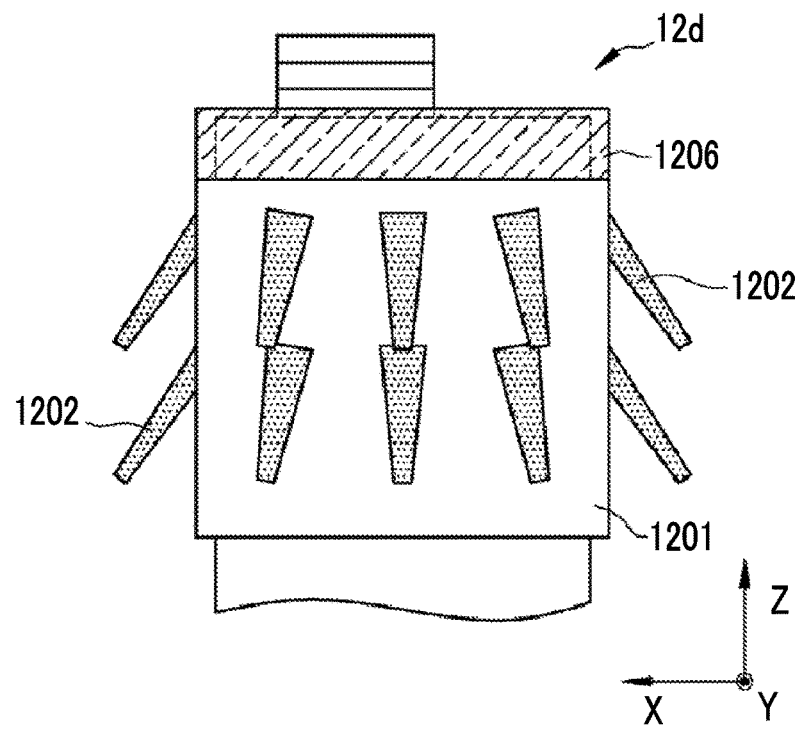
FIG. 58 is a top view of the tip part on which an auxiliary member is mounted.

The endoscope 12 is used in a state in which an auxiliary member 1201, which pushes and smoothes out the creases of a lumen (a large intestine or the like) serving as an object to be observed, is mounted on the tip part 12d in addition to the tip cap 1101 as shown in FIG. 58. The auxiliary member 1201 has a substantially cylindrical shape so as to be mounted on the tip part 12d, and includes a plurality of wing members 1202 that push and smooth out the creases of a lumen by the movement of the insertion part 12a in the extraction direction. Further, the auxiliary member 1201 includes a locking member 1206, which is provided on the tip side thereof and locks the auxiliary member 1201 to the tip part 12d, to prevent a positional deviation of the auxiliary member 1201 with respect to the insertion part 12a during observation or to prevent the auxiliary member 1201 from being separated from the insertion part 12a during observation. The locking member 1206 protrudes from the original tip part 12d to lock the auxiliary member 1201 to the tip part 12d. For this reason, the locking member 1206 may be in the fields 502 of view of the side-viewing observation unit 42 depending on the protruding distance of the locking member 1206. Accordingly, it is preferable that at least the locking member 1206 of the auxiliary member 1201 is made of a transparent material. The reason for this is that the presence of the locking member 1206 does not easily stand out even though the locking member 1206 is in the fields 502 of view of the side-viewing observation unit 42 in a case in which the locking member 1206 is made of a transparent material.

Figure 59:
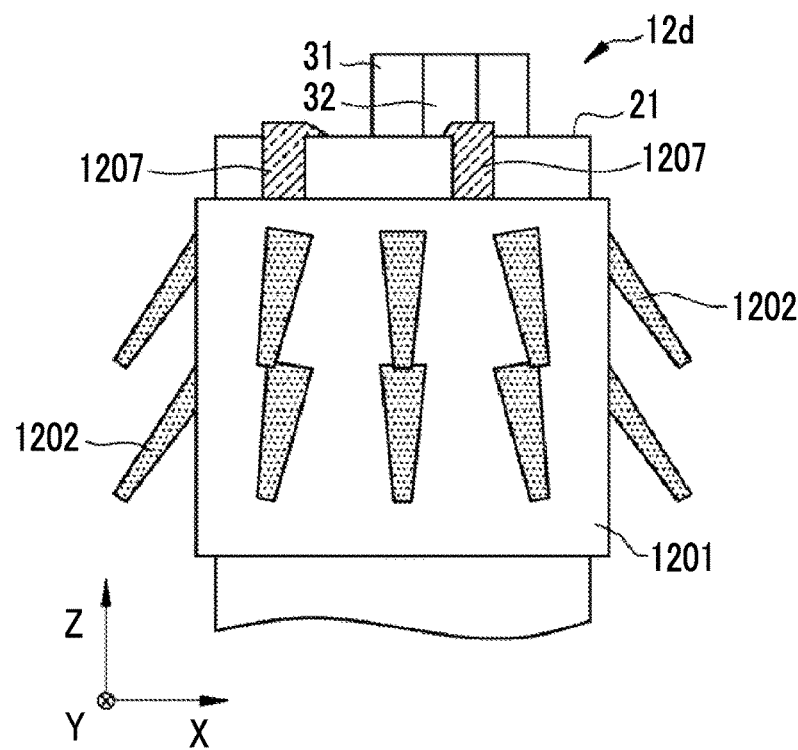
FIG. 59 is a bottom view of the tip part on which an auxiliary member to be locked by claw members is mounted.

Further, there is also a case where the auxiliary member 1201 includes claw-shaped members (hereinafter, referred to as claw members) 1207 locking the auxiliary member 1201 to the tip part 12d instead of the locking member 1206 as shown in FIG. 59. In this case, it is preferable that the claw members 1207 are made of a transparent material as described above. Furthermore, the claw members 1207 are partially provided unlike the locking member 1206. For this reason, it is preferable that the claw members 1207 are provided in a blind spot of the side-viewing observation unit 42 (at a position within the first blind spot portion 114). The reason for this is that the claw members 1207 are not shown up in the fields 502 of view of the side-viewing observation unit 42 in a case in which the claw members 1207 are provided in only the blind spot of the side-viewing observation unit 42. In this case, the claw members 1207 do not need to be made of a transparent material.

Figure 60:
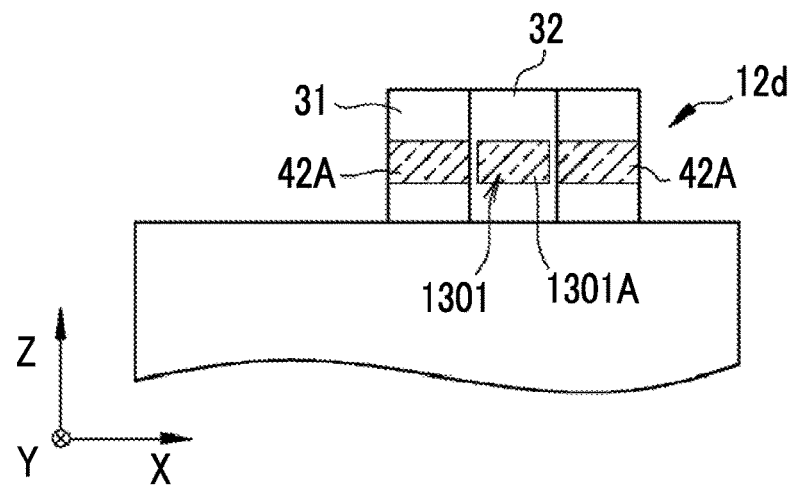
FIG. 60 is a bottom view of the tip part including a lower surface observation unit.

In the first embodiment and the like, the second protruding portion 32 forms a blind spot in the side-viewing observation unit 42. However, as shown in FIG. 60, an observation unit (hereinafter, referred to as a lower surface observation unit) 1301, which compensates the blind spot of the side-viewing observation unit 42, may be provided on the lower surface of the second protruding portion 32. The lower surface observation unit 1301 has the same structure as the side-viewing observation unit 42. A portion of the lower surface observation unit 1301, which is exposed to the lower surface of the second protruding portion 32, is a lower surface observation window 1301A.

Figure 61:
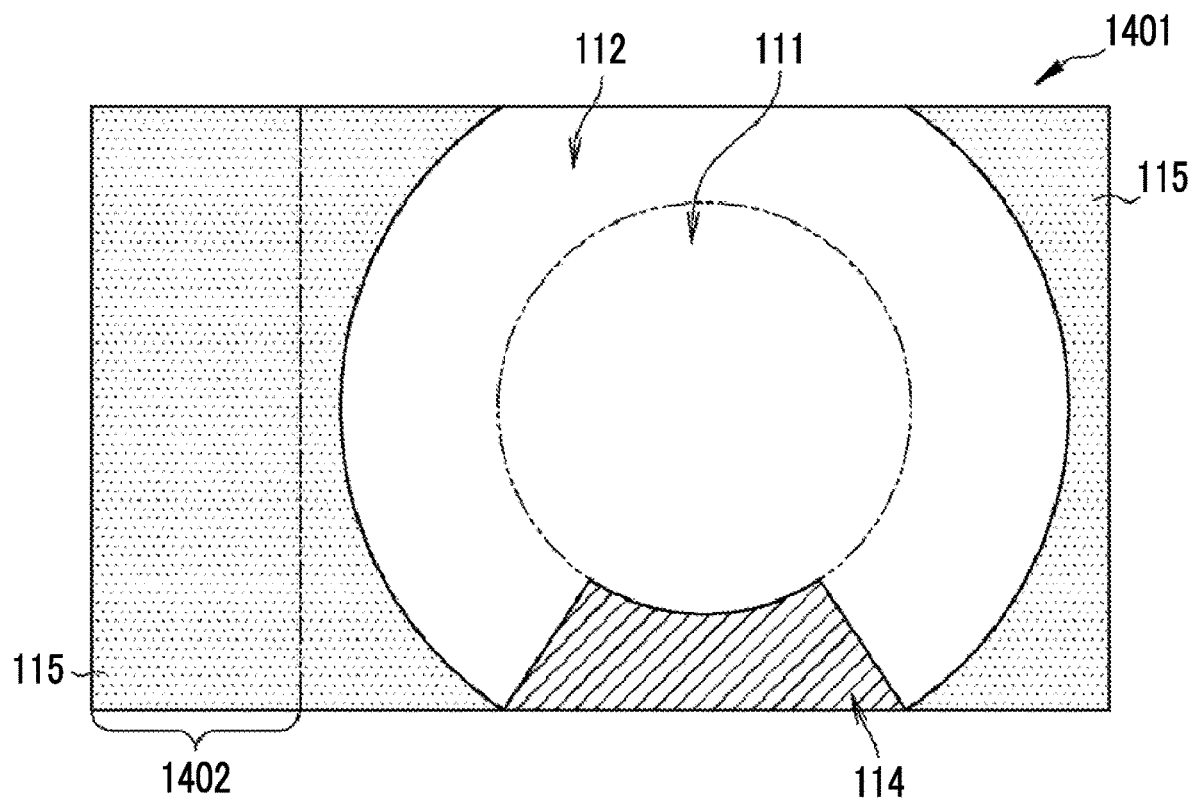
FIG. 61 shows a display image including a marginal region.

In the first embodiment and the like, an object to be observed is substantially fully displayed in the display image 113 and the like. However, there have also been many cases where the display screen of a monitor 18 in recent years is laterally long or vertically long. Even though the direct-viewing observation image 111 and the side-viewing observation image 112 are appropriately displayed in a laterally long display region as in a display image 1401 shown in FIG. 61 in a case in which the laterally long monitor 18 (the same applies to a vertically long monitor, the same shall apply hereinafter), only the second blind spot portion 115 is present and a surplus region (hereinafter, referred to as a marginal region) 1402 in which no useful information is displayed is formed. An appropriate display is, for example, a display in which a portion except for a display region is as small as possible and the second blind spot portion 115 is as small as possible.

Figure 62:
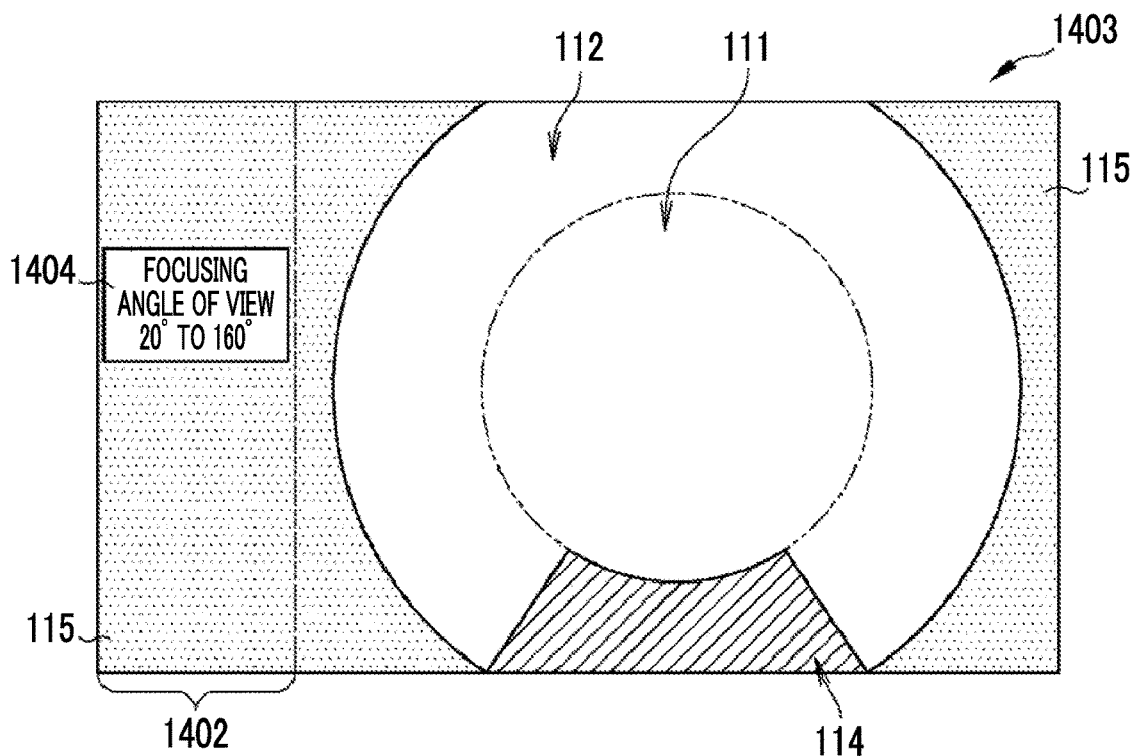
FIG. 62 shows a display image that includes an information display region in a marginal region thereof.
Figure 63:
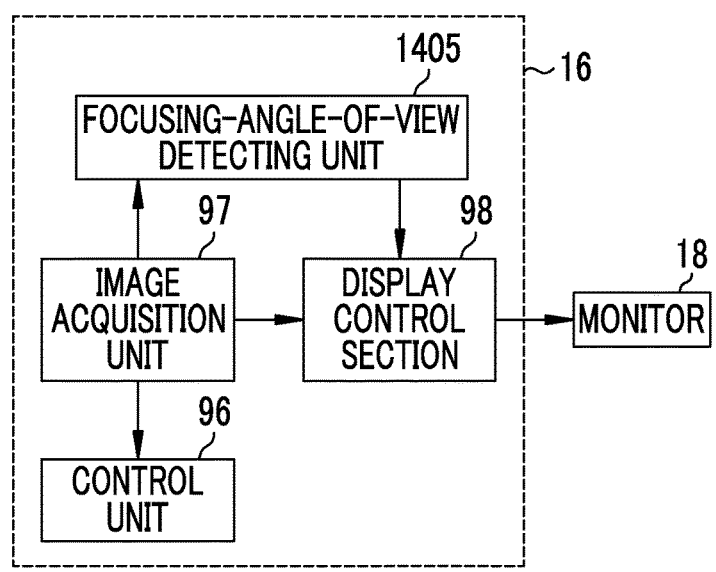
FIG. 63 is a block diagram of a processor device that is provided with a focusing-angle-of-view detecting unit.

In a case in which the marginal region 1402 is formed in a display screen due to an aspect ratio of the display screen of the monitor 18 or the like as described above, it is preferable that the display control section 98 provides an information display region 1404 in the marginal region 1402 as in a display image 1403 shown in FIG. 62. Further, for example, information, such as the range of a focusing angle of view, is displayed in the information display region 1404. The processor device 16 is provided with a focusing-angle-of-view detecting unit 1405 as shown in FIG. 63 to display the range of a focusing angle of view. For example, the focusing-angle-of-view detecting unit 1405 acquires the direct-viewing observation image 111 and the side-viewing observation image 112 from the image acquisition unit 97, detects a region focused (being in focus) in the direct-viewing observation image 111 or the side-viewing observation image 112 by using the acquired direct-viewing observation image 111 and the acquired side-viewing observation image 112, and converts the detection result into an angle of view. The display control section 98 displays the focusing angle of view, which is calculated by the focusing-angle-of-view detecting unit 1405, in the information display region 1404. The detection of a focused region using the direct-viewing observation image 111 and the side-viewing observation image 112 can be performed by a contrast method, a phase-contrast method, or the like in the same manner as a principle for detecting a focus in an auto-focus function of a digital camera or the like.

Figure 64:
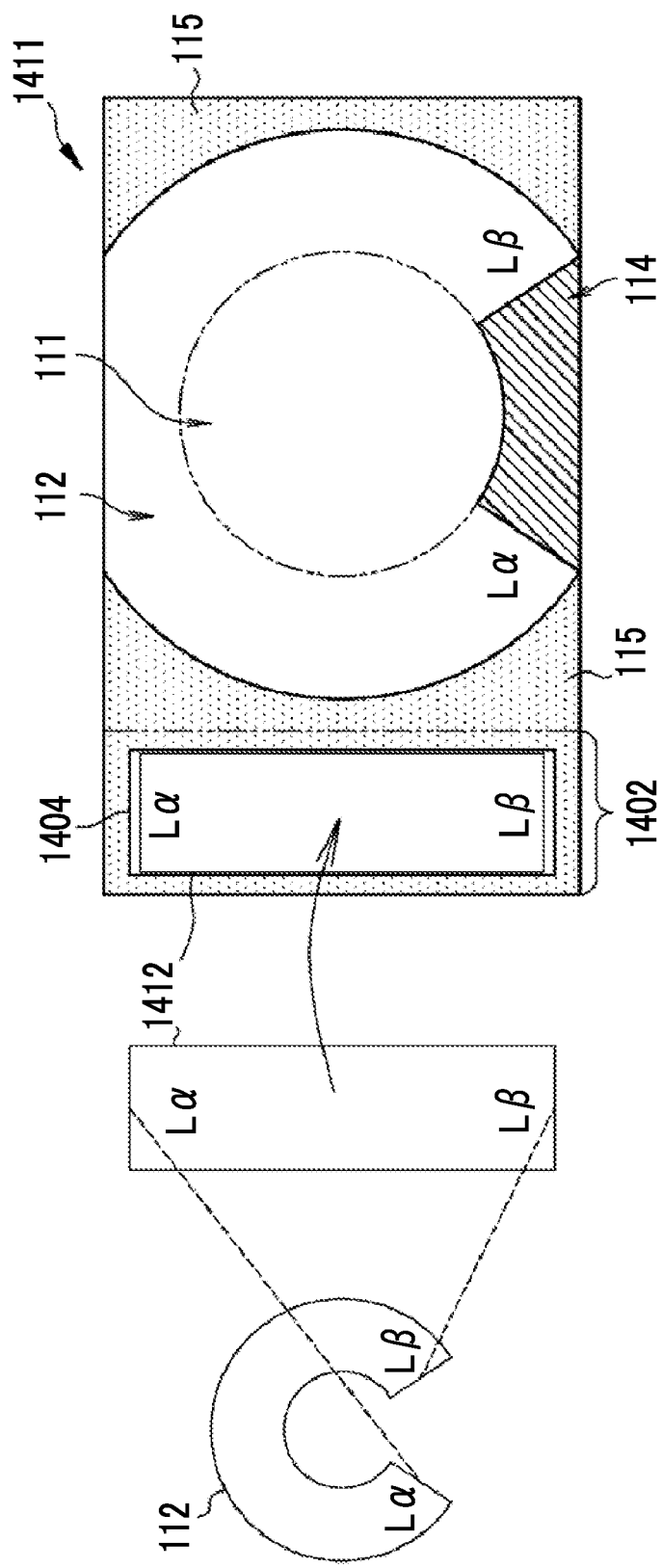
FIG. 64 shows a display image in which a modified side-viewing observation image is displayed in a marginal region.
Figure 65:
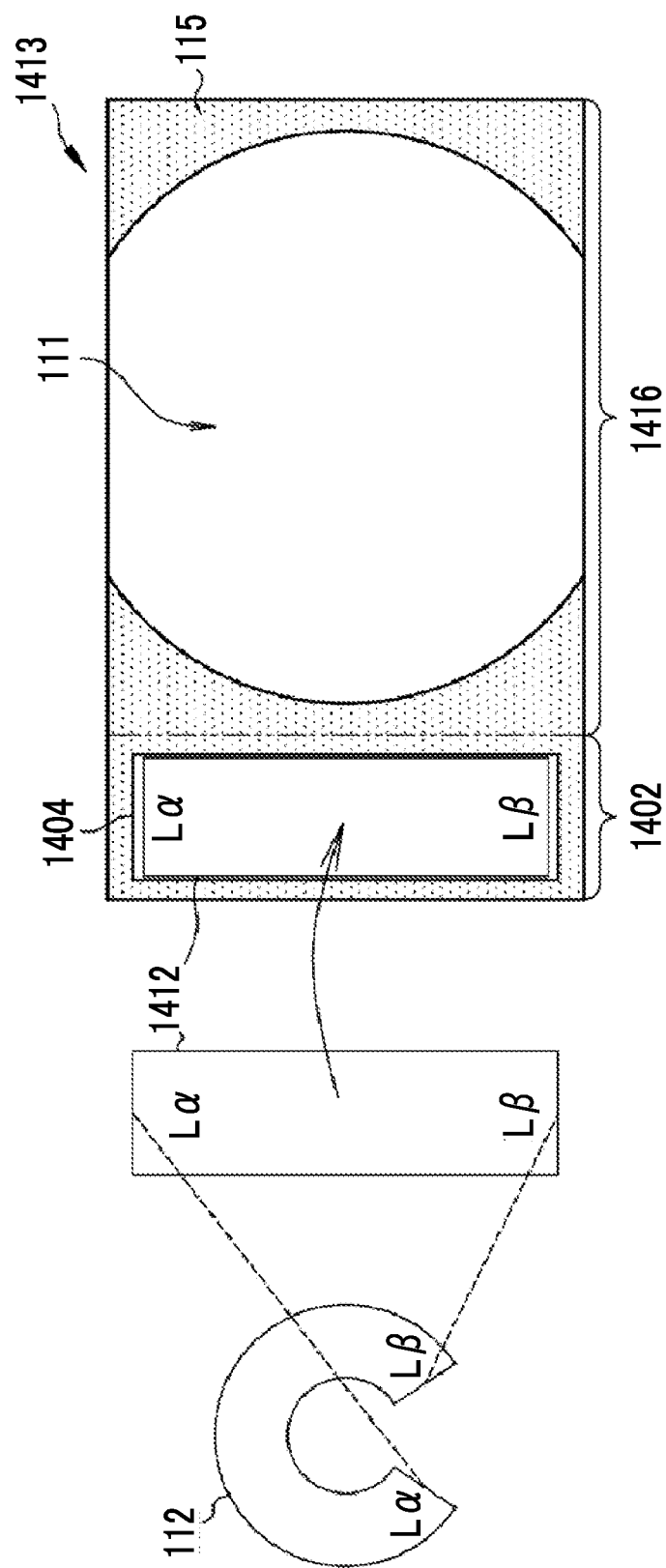
FIG. 65 shows a display image in which a modified side-viewing observation image is displayed in a marginal region.

A focusing angle of view has been displayed above in the information display region 1404 by way of example, but other information may be displayed in the information display region 1404. That is, as long as the marginal region 1402 is provided with the information display region 1404 and some sort of information is displayed in the information display region 1404 so that at least a part of the marginal region 1402 can be effectively used, the contents of information to be displayed is arbitrary. For example, as in a display image 1411 shown in FIG. 64, a modified side-viewing observation image 1412 of which a portion of the side-viewing observation image 112 in which an object to be observed is shown up is modified into a rectangular shape may be displayed in the information display region 1404 of the marginal region 1402. Reference characters $L\alpha$ and $L\beta$ shown in the side-viewing observation image 112 and the modified side-viewing observation image 1412 show a correspondence relationship between the side-viewing observation image 112 and the modified side-viewing observation image 1412. In a case in which the modified side-viewing observation image 1412 is displayed in the information display region 1404 as described above, only the direct-viewing observation image 111 may be displayed in a main region 1416 for displaying an object to be observed as in a display image 1413 shown in FIG. 65.

Figure 66:
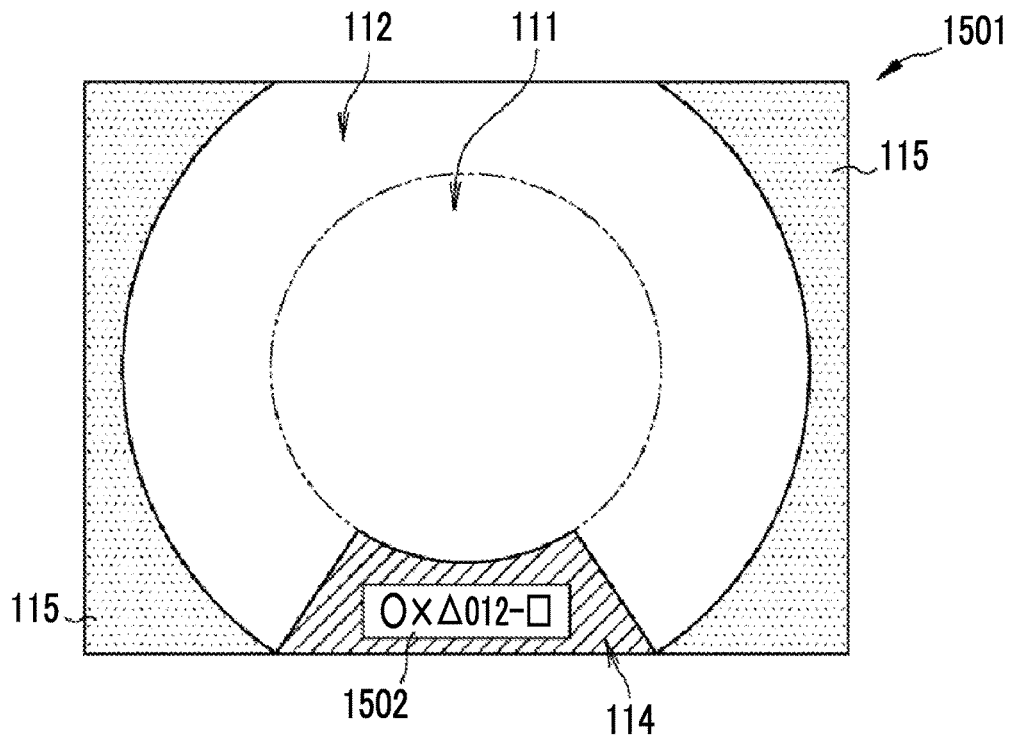
FIG. 66 shows a display image in which an information display region is provided on a mask of a first blind spot portion.

In addition, in a case in which the first blind spot portion 114 is present even though the marginal region 1402 is not present, an information display region 1502 is provided in the first blind spot portion 114 and information, such as the model name of the endoscope 12, is displayed in the information display region 1502 as in a display image 1501 shown in FIG. 66. Accordingly, the first blind spot portion 114 can be effectively used.

Figure 67:
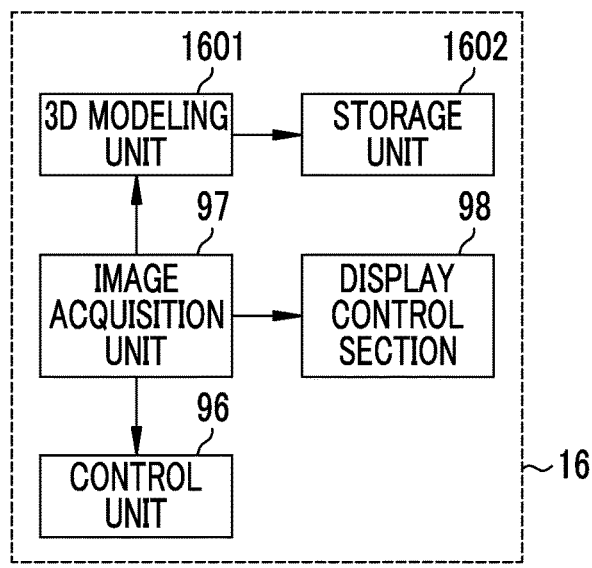
FIG. 67 is a block diagram of a processor device including a 3D modeling unit.
Figure 68:
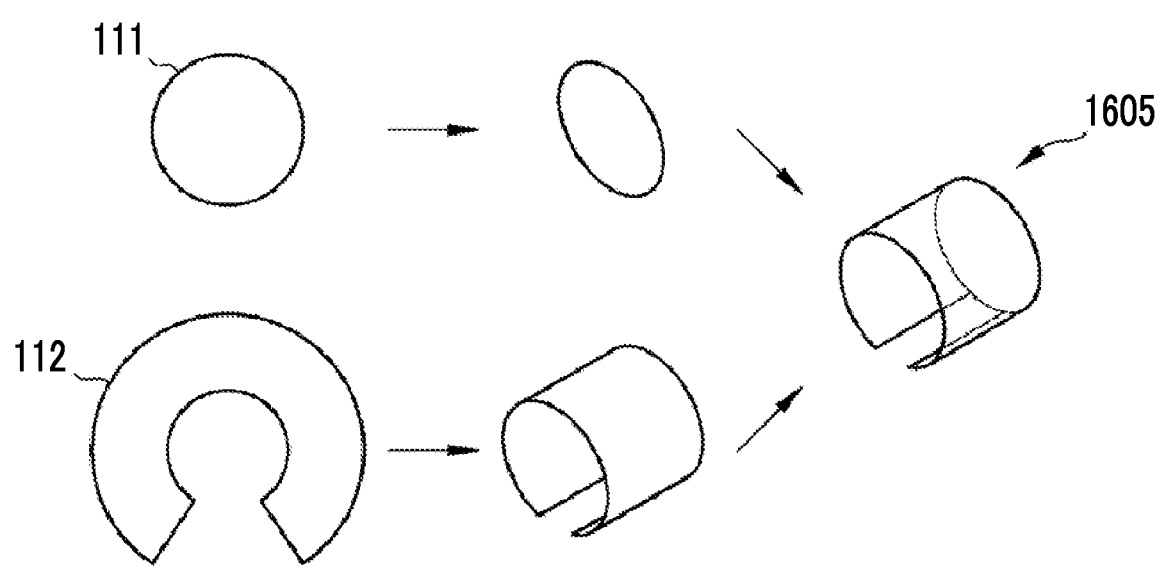
FIG. 68 is a diagram illustrating the action of the 3D modeling unit.

In the first embodiment and the like, the display image 113 and the like are generated using the direct-viewing observation image 111 and the side-viewing observation image 112, and are displayed on the monitor 18. However, a three-dimensional model (3D model) 1605 can be generated using the direct-viewing observation image 111 or the side-viewing observation image 112. In this case, for example, the processor device 16 may be provided with a 3D modeling unit 1601 and a storage unit 1602 as shown in FIG. 67. As shown in FIG. 68, the 3D modeling unit 1601 generates the 3D model 1605 of an object to be observed by using the direct-viewing observation image 111 and the side-viewing observation image 112. The 3D model 1605, which is modeled by the 3D modeling unit 1601, is generated. Then, the storage unit 1602 stores the 3D model 1605 that is modeled by the 3D modeling unit 1601. The 3D model 1605, which is stored in the storage unit 1602 in this way, can be used for the support of the next diagnosis or the like, the re-examination using a simulation, or the like. The processor device 16 has been provided with the 3D modeling unit 1601 and the storage unit 1602 above, but a computer or the like connected to the endoscope system 10 may be provided with the 3D modeling unit 1601 and the storage unit 1602.

The endoscope system 10, which is used in a state in which the insertion part 12*a* is inserted into a subject, has been described in the first embodiment and the like by way of example, but the first embodiment and the like can also be used for a capsule endoscope that is used in a state in which an examinee swallows the capsule endoscope.

The direct-viewing observation unit 41 and the side-viewing observation unit 42 share the image pickup lens 61 and the image sensor 66 in the first embodiment and the like, but the image pickup lens 61 and the image sensor 66 of the direct-viewing observation unit 41 may be separate from the image pickup lens 61 and the image sensor 66 of the side-viewing observation unit 42.

EXPLANATION OF REFERENCES

10, 200: endoscope system
11: universal cord
12: endoscope
12*a*: insertion part
12*b*: operation unit
12*c*: bendable part
12*d*: tip part
12*e*: angle knob
13: washing switch
14: light source device
16: processor device
17: tank
18: monitor
19: console
21: tip surface
31: first protruding portion
32: second protruding portion
41: direct-viewing observation unit
41A: direct-viewing observation window
42: side-viewing observation unit
42A: side-viewing observation window
43: side-viewing illumination unit
43A: first side-viewing illumination window
43B: second side-viewing illumination window
51, 52, 53: nozzle
54: direct-viewing illumination unit
54A: direct-viewing illumination window
59: conversion unit
61: image pickup lens
62: front group lens
63: mirror lens
64: rear group lens
66: image sensor
67: cover glass
71, 77, 84, 93: light guide
72: reflective member
73: filling member
76: air/liquid supply channel
78: illumination lens
81: direct-viewing illumination unit
81A: direct-viewing illumination window
82: forceps port
91: light source
92: light source control unit
96: control unit
97: image acquisition unit
98: display control section
101: display ratio setting unit
102: display image generating unit
111: direct-viewing observation image
111A, 112A: graph
112: side-viewing observation image
113: display image
114: first blind spot portion
115: second blind spot portion
123, 126, 128, 129, 302, 304, 410, 411, 523, 1120, 1121, 1401, 1403, 1411, 1413, 1501: display image
201: movement detecting unit
202: movement sensor
205: object to be observed
301: mask display ratio setting unit
401: display position setting unit
421: head mount display
501, 502: field of view
503: blind spot
513: third blind spot portion
601: overlapping field of view
602: overlapping region
611: overlapping region-detecting unit
612: overlapping region-removing unit
613: signal level-correcting unit
701, 702: distortion
705: aberration connecting unit
706: distance measurement unit
830: image processing unit
1001: display region setting unit
1002: display region
1013: display image
1101: tip cap
1101A: outline
1102: through hole
1111: line
1122: portion of tip cap near outline
1123: portion corresponding to through hole
1201: auxiliary member
1202: wing member
1206: locking member
1207: claw member
1301: lower surface observation unit
1301A: lower surface observation window
1402: marginal region
1404, 1502: information display region
1405: focusing-angle-of-view detecting unit
1412: modified side-viewing observation image
1416: main region
1601: 3D modeling unit
1602: storage unit
1605: 3D model
C0: center
D1: distance
Lα, Lβ: reference character
V1, V2, V3: movement speed

What is claimed is:

1. An endoscope system comprising:
an endoscope including a side-viewing observation unit that includes a field of view in a lateral direction of an insertion part to be inserted into an object to be observed and a protruding portion that protrudes from the insertion part and forms a blind spot in the field of view of the side-viewing observation unit;
a processor configured to function as an image acquisition unit and a display control section; and
a monitor, wherein
the image acquisition unit acquires a side-viewing observation image by using the side-viewing observation unit;
the display control section generates a display image including the side-viewing observation image; and
the monitor displays the display image; wherein
the display control section allows at least a part of the blind spot of the side-viewing observation image, in which the protruding portion is appeared, not to be displayed, and displays the side-viewing observation image on the monitor, and
the display control section masks a portion of the display image that is outside the side-viewing observation image,
wherein the display control section changes a ratio of a portion, which is not to be displayed, of the blind spot in accordance with a change of an orientation of the insertion part or a change of a velocity or an acceleration of insertion/extraction of the insertion part.

2. The endoscope system according to claim 1, wherein the display control section allows at least a part of the blind spot not to be displayed by offsetting a display position of the side-viewing observation image with respect to a display region on the monitor.

3. The endoscope system according to claim 2, wherein the display control section allows at least a part of the blind spot not to be displayed by enlarging the side-viewing observation image with respect to the display region on the monitor.

4. The endoscope system according to claim 3, wherein the display control section includes a blind spot-non-display mode as a display mode for the side-viewing observation image, and allows at least a part of the blind spot not to be displayed and displays the side-viewing observation image on the monitor in a case in which the display mode is set to the blind spot-non-display mode.

5. The endoscope system according to claim 3, wherein the display control section allows the entire blind spot not to be displayed.

6. The endoscope system according to claim 2, wherein the display control section includes a blind spot-non-display mode as a display mode for the side-viewing observation image, and allows at least a part of the blind spot not to be displayed and displays the side-viewing observation image on the monitor in a case in which the display mode is set to the blind spot-non-display mode.

7. The endoscope system according to claim 6, wherein the display control section allows the entire blind spot not to be displayed.

8. The endoscope system according to claim 2, wherein the display control section allows the entire blind spot not to be displayed.

9. The endoscope system according to claim 1, wherein the display control section allows at least a part of the blind spot not to be displayed by enlarging the side-viewing observation image with respect to a display region on the monitor.

10. The endoscope system according to claim 9, wherein the display control section includes a blind spot-non-display mode as a display mode for the side-viewing observation image, and allows at least a part of the blind spot not to be displayed and displays the side-viewing observation image on the monitor in a case in which the display mode is set to the blind spot-non-display mode.

11. The endoscope system according to claim 9, wherein the display control section allows the entire blind spot not to be displayed.

12. The endoscope system according to claim 1, wherein the display control section includes a blind spot-non-display mode as a display mode for the side-viewing observation image, and allows at least a part of the blind spot not to be displayed and displays the side-viewing observation image on the monitor in a case in which the display mode is set to the blind spot-non-display mode.

13. The endoscope system according to claim 12, wherein the display control section allows the entire blind spot not to be displayed.

14. The endoscope system according to claim 1, wherein the display control section allows the entire blind spot not to be displayed.

15. The endoscope system according to claim 1, wherein the display control section changes the ratio of the portion, which is not to be displayed, of the blind spot in a case in which the insertion part is to be inserted into the object to be observed and a case in which the insertion part is to be extracted from the object to be observed.

16. The endoscope system according to claim 1, wherein the endoscope includes a direct-viewing observation unit that includes a field of view in a tip direction of the insertion part,
the image acquisition unit acquires a direct-viewing observation image by using the direct-viewing observation unit, and
the display control section adjusts display ratios of the side-viewing observation image and the direct-viewing observation image, and changes the ratio of the portion, which is not to be displayed, of the blind spot in accordance with the display ratios of the side-viewing observation image and the direct-viewing observation image.

17. The endoscope system according to claim 1, further comprising:
a nozzle that ejects a washing substance to the side-viewing observation unit to wash the side-viewing observation unit and is provided in a non-display region not to be displayed in a case in which the display control section displays the side-viewing observation image on the monitor.

18. A method of driving an endoscope system, the endoscope system including an endoscope including a side-viewing observation unit that includes a field of view in a lateral direction of an insertion part to be inserted into an object to be observed and a protruding portion that protrudes from the insertion part and forms a blind spot in the field of view of the side-viewing observation unit, a processor configured to function as an image acquisition unit and a display control section, and a monitor,
wherein the image acquisition unit acquires a side-viewing observation image by using the side-viewing observation unit, the display control section generates a display image including the side-viewing observation image, and the monitor displays the display image, the method comprising:
a step of allowing at least a part of the blind spot of the side-viewing observation image, in which the protruding portion is appeared, not to be displayed, and displaying the side-viewing observation image on the monitor by the display control section, and masking a portion of the display image that is outside the side-viewing observation image by the display control section,
wherein the display control section changes a ratio of a portion, which is not to be displayed, of the blind spot in accordance with a change of an orientation of the insertion part or a change of a velocity or an acceleration of insertion/extraction of the insertion part.

* * * * *